US008569472B2

(12) United States Patent
Gottwein et al.

(10) Patent No.: US 8,569,472 B2
(45) Date of Patent: Oct. 29, 2013

(54) EFFICIENT CELL CULTURE SYSTEM FOR HEPATITIS C VIRUS GENOTYPE 6A

(75) Inventors: Judith M. Gottwein, Frederiksberg C (DK); Troels Kasper Hoyer Scheel, Kobenhavn NV (DK); Tanja Bertelsen Jensen, Frederiksberg C (DK); Jens Bukh, Praesto (DK)

(73) Assignee: Hvidovre Hospital, Hvidovre (DK)

( * ) Notice: Subject to any disclaimer, the term of this patent is extended or adjusted under 35 U.S.C. 154(b) by 390 days.

(21) Appl. No.: 12/808,565

(22) PCT Filed: Dec. 19, 2008

(86) PCT No.: PCT/DK2008/050332
§ 371 (c)(1),
(2), (4) Date: Nov. 22, 2010

(87) PCT Pub. No.: WO2009/080052
PCT Pub. Date: Jul. 2, 2009

(65) Prior Publication Data
US 2011/0059512 A1 Mar. 10, 2011

(30) Foreign Application Priority Data

Dec. 20, 2007 (EP) .................... 07123825
Dec. 20, 2007 (EP) .................... 07123851
Aug. 15, 2008 (EP) .................... 08162466

(51) Int. Cl.
*C07H 21/00* (2006.01)
*A61K 39/12* (2006.01)
*A61K 39/29* (2006.01)
*A61K 39/295* (2006.01)
*C12N 7/00* (2006.01)

(52) U.S. Cl.
USPC ............... 536/23.72; 424/199.1; 424/202.1; 424/228.1; 435/235.1; 435/69.1

(58) Field of Classification Search
None
See application file for complete search history.

(56) References Cited

U.S. PATENT DOCUMENTS

| 5,428,145 | A  | 6/1995  | Okamoto et al. |
| 6,638,714 | B1 | 10/2003 | Linnen et al. |
| 7,674,612 | B2 | 3/2010  | Rice et al. |
| 7,935,676 | B2 | 5/2011  | Wakita et al. |
| 2007/0073039 | A1 | 3/2007 | Chisari |
| 2010/0093841 | A1 | 4/2010 | Gottwein et al. |
| 2010/0158948 | A1 | 6/2010 | Scheel et al. |
| 2010/0278865 | A1 | 11/2010 | Wakita et al. |
| 2010/0291545 | A1 | 11/2010 | Wakita et al. |
| 2011/0021611 | A1 | 1/2011 | Jensen et al. |
| 2011/0045020 | A1 | 2/2011 | Akazawa et al. |
| 2011/0059512 | A1 | 3/2011 | Gottwein et al. |
| 2011/0059513 | A1 | 3/2011 | Scheel et al. |
| 2011/0092688 | A1 | 4/2011 | Wakita et al. |
| 2011/0294195 | A1 | 12/2011 | Gottwein et al. |
| 2012/0003714 | A1 | 1/2012 | Hoelke et al. |
| 2012/0003719 | A1 | 1/2012 | Prento et al. |

FOREIGN PATENT DOCUMENTS

| EP | 1801209 A1 | 6/2007 |
| EP | 1930416 A1 | 6/2008 |
| WO | 9904008 A2 | 1/1999 |
| WO | 0121807 A1 | 3/2001 |
| WO | 02052015 A2 | 7/2002 |
| WO | 02059321 A2 | 8/2002 |
| WO | 2005047463 A2 | 5/2005 |
| WO | 2005053516 A2 | 6/2005 |
| WO | 2006096459 A2 | 9/2006 |
| WO | 2007037429 A1 | 4/2007 |
| WO | 2007041487 A2 | 4/2007 |
| WO | 2007073039 A1 | 6/2007 |
| WO | 2008125117 A1 | 10/2008 |
| WO | 2008125119 A1 | 10/2008 |
| WO | 2008141651 A1 | 11/2008 |
| WO | 2009080052 A1 | 7/2009 |
| WO | 2009080053 A1 | 7/2009 |
| WO | 2011/118743 A1 | 9/2011 |

OTHER PUBLICATIONS

GenBank Accession No: AB047639.1, HCV JFH1 complete genomic RNA, Nov. 12, 2005.*
GenBank Accession No: Y12083.1, HCV genotype 6a RNA for HCV polyprotein, Nov. 10, 2005.*
Gottwein et al., "Cutting the Gordian Knot-Development and Biological Relevance of Hepatitis C Virus Cell Culture Systems", Advances in Virus Research, 2008, pp. 51-133, vol. 71.
Gottwein et al., "Development and Characterization of Hepatitis C Virus Genotype 1-7 Cell Culture Systems: Role of CD91 and Scavenger Receptor Class B Type I and Effect of Antiviral Drugs", Hepatology, Oct. 9, 2008, pp. 364-377, vol. 49, No. 2.
Gottwein et al., "Novel Chimeric Cell Culture System for Hepatitis C Genotypes 1A, 1B, 3A and 4A", Annual Meeting of the European Association for the Study of the Liver, Apr. 2007, pp. S30, vol. 46, No. Suppl.
Gottwein et al., "Robust Hepatitis C Genotype 3a Cell Culture Releasing Adapted Intergenotypic 3a/2a (S52/JFH1) Viruses", Gastroenterology, Nov. 2007, pp. 1614-1626, vol. 133, No. 5, Elsevier, Philadelphia, Pa.
Graham et al., "A Genotype 2b NS5B Polymerase with Novel Substitutions Supports Replication of a Chimeric HCV 1b: 2b Replicon Containing a Genotype 1b NS3-5A Background", Antiviral Research, Jan. 2006, pp. 24-30, vol. 69, No. 1, Elsevier Science BV., Amsterdam, NL.
International Preliminary Report on Patentability for PCT/DK2008/050333 dated Mar. 29, 2010.

(Continued)

*Primary Examiner* — Stacy B. Chen
(74) *Attorney, Agent, or Firm* — Thompson Coburn LLP; Charles P. Romano

(57) ABSTRACT

The present inventors developed hepatitis C virus 6a/2a intergenotypic recombinants in which the JFH1 structural genes (Core, E1 and E2), p7 and the complete NS2 were replaced by the corresponding genes of the genotype 6a reference strain HK6a. Sequence analysis of recovered 6a/2a recombinants from 2 transfection experiments and subsequent reverse genetic studies revealed adaptive mutations in E1 and E2. Conclusion: The developed 6a/2a viruses provide a robust in vitro tool for research in HCV genotype 6, including vaccine studies and functional analysis.

18 Claims, 10 Drawing Sheets

(56) References Cited

OTHER PUBLICATIONS

Figure 4:
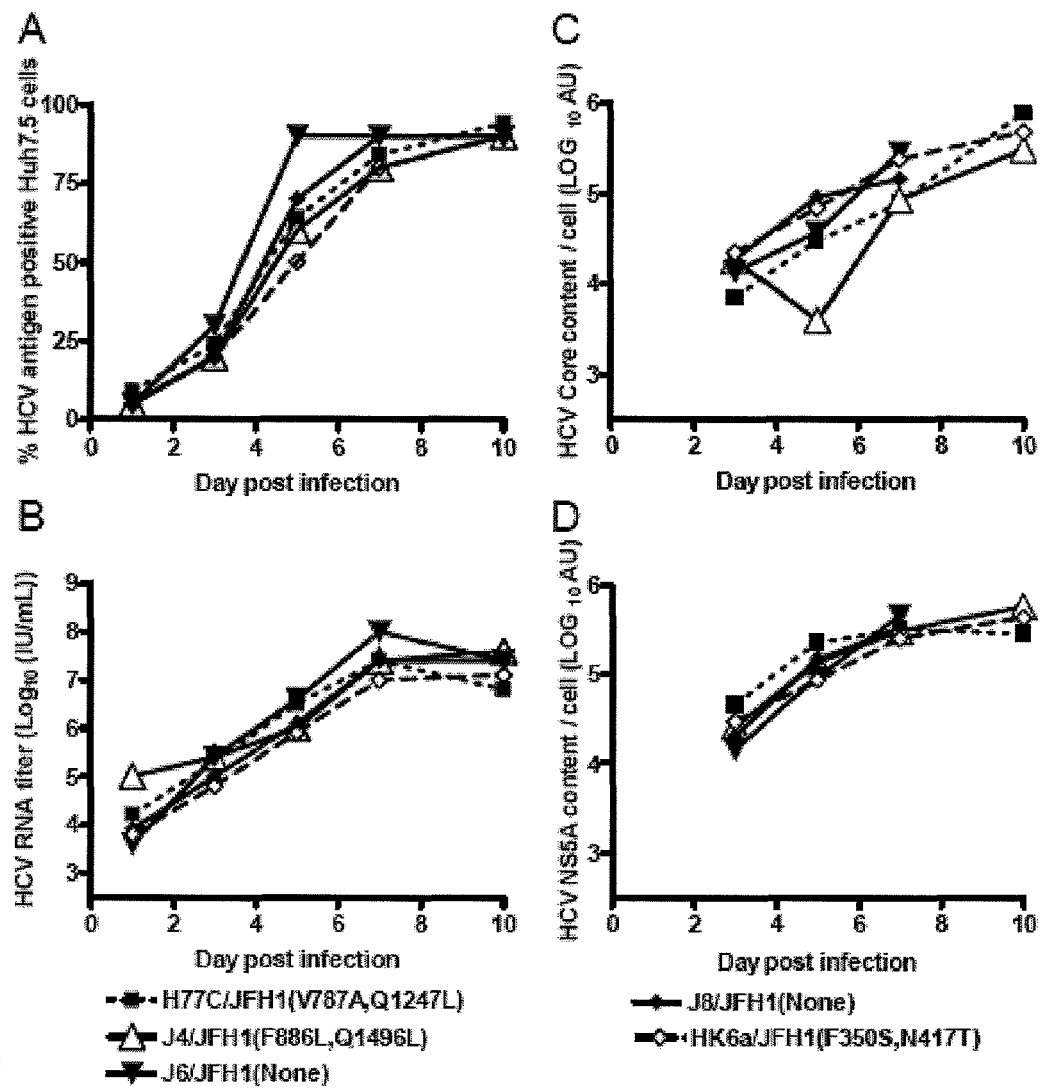

Kato et al., "Efficient Replication of the Genotype 2a Hepatitis C Virus Subgenomic Replicon", Gastroenterology, Dec. 2003, pp. 1808-1817, vol. 125, No. 6, Elsevier, Philadelphia, Pa.
Kaul et al., "Cell Culture Adaption of Hepatitis C Virus and in vivo Viability of an Adapted Varient", Journal of Virology, Dec. 2007, pp. 13168-13179, vol. 81, No. 23, The American Society for Microbiology, US.
Krieger et al., "Enhancement of Hepatitis C Virus RNA Replication by Cell Culture-Adaptive Mutations", Journal of Virology, May 2001, pp. 4614-4624, vol. 75, No. 10, The American Society for Microbiology, US.
Lindenbach et al., "Complete Replication of Hepatitis C Virus in Cell Culture", Science, Jul. 22, 2005, pp. 623-626, vol. 309, No. 5734.
Lohmann et al., "Mutations in Hepatitis C Virus RNAs Conferring Cell Culture Adaptation", Journal of Virology, Feb. 2001, pp. 1437-1449, vol. 75, No. 3, The American Society for Microbiology, US.
Pietschmann et al., "Construction and Characterization of Infectious Intragenotypic and Intergenotypic Hepatitis C Virus Chimeras", Proceedings of the National Academy of Science of USA, May 9, 2006, pp. 7408-7413, vol. 103, No. 19, National Academy of Science, Washington D.C.
Sakai et al, "In Vivo Study of the HC-TN Strain of Hepatitis C Virus Recovered from a Patient with Fulminant Hepatitis: TNA Transcripts of a Molecular Clone (pHC-TN) are Infectious in Chimpanzees But Not in Huh7.5 Cells", Journal of Virology, Jul. 2007, pp. 7208-7219, vol. 81, No. 13, American Society for Microbiology.
Scheel et al., "Development of JFH1-based Cell Culture Systems for Hepatitis C Virus Genotype 4a and Evidence for Cross-Genotype Neutralization", Proceedings of the National Academy of Science of USA, Jan. 22, 2008, pp. 997-1002, vol. 105, No. 3, National Academy of Science, Washington D.C., US.
Wakita et al., "Production of Infectious Hepatitis C Virus in Tissue Culture from a Cloned Viral Genome", Nature Medicine, Jul. 2005, pp. 791-796, vol. 11, No. 7, Nature Publishing Group, New York, NY.
Yanagi et al., "Transcripts of a Chimeric cDNA Clone of Hepatitis C Virus Genotype 1b are Infectious in vivo", Virology, Jan. 1, 1998, pp. 161-172, vol. 244, No. 1.
Yi et al., "Compensatory Mutations in E1, p7, NS2, and NS3 Enhance Yields of Cell Culture-Infectious Intergenotypic Chimeric Hepatitis C Virus", Journal of Virology, Jan. 2007, pp. 629-638, vol. 81, No. 2, American Society for Microbiology, US.
International Search Report and Written Opinion of the International Searching Authority dated Nov. 3, 2009 for PCT Application No. PCT/DK2008/050332.
Hui et al., "Interferon and Ribavirin Therapy for Chronic Hepatitis C Virus Genotype 6: A Comparison with Genotype 1", Article, Apr. 1, 2003, pp. 1071-1074, vol. 187.
Kato et al., "Sequence Analysis of Hepatitis C Virus Isolated From a Fulminant Hepatitis Patient", Journal of Medical Virology, 2001, pp. 334-339, vol. 64.
Murphy et al, "A New Genotype of Hepatitis C Virus Originating From Central Africa", Hepatology, Oct. 2007, p. 623A, vol. 64, No. 4.
"Written Description Training Materials", United States Patent and Trademark Office, Department of Commerce, Mar. 2008, pp. 1-84, Revision 1 (part 2).
Gottwein et al., "Development and Characterization of Hepatitis C Virus Genotype 1-7 Cell Culture Systems: Role of CD81 and Scavenger Receptor Class B Type I and Effect of Antiviral Drugs", Hepatology, Oct. 2008, pp. 364-377, vol. 49, No. 2.
Murphy, "Hepatitis C Virus Isolate QC69 Polyprotein Gene, Complete CDs", Database EMBL E.B.I. Hinxton U.K., Nov. 2007, XP002520134 Database Accession No. EF108306.

Zhong et al., "Robust Hepatitis C Virus Infection in vitro", Proceedings of the National Academy of Sciences, 2005, pp. 9294-9299, vol. 102, No. 26.
Appel et al., "Mutational Analysis of Hepatitis C Virus Nonstructural Protein 5A: Potential Role of Differential Phosphorylation in RNA Replication and Identification of a Genetically Flexible Domain", Journal of Virology, Mar. 2005, pp. 3187-3194, vol. 79, No. 5.
Appel et al., "Essential Role of Domain III of Nonstructural Protein 5A for Hepatitis C Virus Infectious Particle Assembly", PLOS Pathogens, Mar. 2008, pp. 1-14, vol. 4, Issue 3.
Bukh et al., "Mutations That Permit Efficient Replication of Hepatitis C Virus RNA in Huh-7 Cells Prevent Productive Replication in Chimpanzees", Proc. Natl. Acad. Sci., Oct. 29, 2002, pp. 14416-14421, vol. 99, No. 22.
Chamberlain et al., "Complete Nucleotide Sequence of a Type 4 Hepatitis C Virus Variant, the Predominant Genotype in the Middle East", Journal of General Virology, 1997, pp. 1341-1347, vol. 78.
Forns et al., "Hepatitis C Virus Lacking the Hypervariable Region 1 of the Second Envelope Protein is Infectious and Causes Acute Resolving or Persistent Infection in Chimpanzees", Proceedings of the National Academy of Sciences of the United States of America, Nov. 21, 2000, pp. 13318-13323, vol. 97, No. 24.
Gottwein et al., "Monocistronic Hepatitis C Reporter Virus Recombinants of All Major Genotypes Expressing Enhanced Green Fluorescent Protein Tagged NS5A Protein", Journal of Hepatology, Apr. 2009, p. S33, vol. 50, No. sup1.
Hou et al., "A Recombinant Replication-Competent Hepatitis C Virus Expressing Azami-Green, a Bright Green-Emitting Fluorescent Protein, Suitable for Visualization of Infected Cells", Biochemical and Biophysical Research Communications, Sep. 9, 2008, pp. 7-11, vol. 377, No. 1.
Jensen et al., "Highly Efficient JFH1-Based Cell-Culture System for Hepatitis C Virus Genotype 5a: Failure of Homologous Neutralizing-Antibody Treatment to Control Infection", Journal of Infectious Diseases, Dec. 15, 2008, pp. 1756-1765, vol. 198.
Jensen, "Efficient Cell Culture System for Hepatitis C Virus Genotype 5a", Department of Infectious Diseases and Clinical Research Unit, Copenhagen University Hospital, Master Thesis, Mar. 2007, pp. 1-60.
Kim et al., "Monitoring the Antiviral Effect of Alpha Interferon on Individual Cells" Journal of Virology, Aug. 2007, pp. 8814-8820, vol. 81, No. 16.
Moradpour et al., "Insertion of Green Fluorescent Protein into Nonstructural Protein 5A Allows Direct Visualization of Functional Hepatitis C Virus Replication Complexes", Journal of Virology, Jul. 2004, pp. 7400-7409, vol. 78, No. 14.
Prentoe et al., "HCV Entry Related Studies", Booklet, 4th Smogen Summer Symposium on Virology, Aug. 2008, p. 23.
Schaller et al., "Analysis of Hepatitis C Virus Superinfection Exclusion by Using Novel Fluorochrome Gene-Tagged Viral Genomes", Journal of Virology, May 2007, pp. 4591-4603, vol. 81, No. 9.
Suzuki et al., "Novel Chimeric Hepatitis C Virus Genome Comprising Nucleic Acid Encoding Epitope Tag Peptide at Hypervariable Region 1 of E2 Protein, Useful as Vaccine for Preventing or Treating Hepatitis-C Viral Infection", Database WPI Week 200914, Thomson Scientific, AN 2009-E03534, Jan. 22, 2009.
International Preliminary Report on Patentability (Chapter II) for PCT/DK2008/050113 issued May 25, 2009.
"Written Description Training Materials", United States Patent and Trademark Office, Department of Commerce, Mar. 2008, pp. 1-84, Revision 1 (Part 1).
International Search Report and Written Opinion for PCT/DK2009/050193 dated Oct. 30, 2009.
Simmonds et al., "Consensus Proposals for a Unified System of Nomenclature of Hepatitis C Virus Genotypes", Hepatology, Oct. 2005, pp. 962-973, vol. 42, No. 4.

* cited by examiner

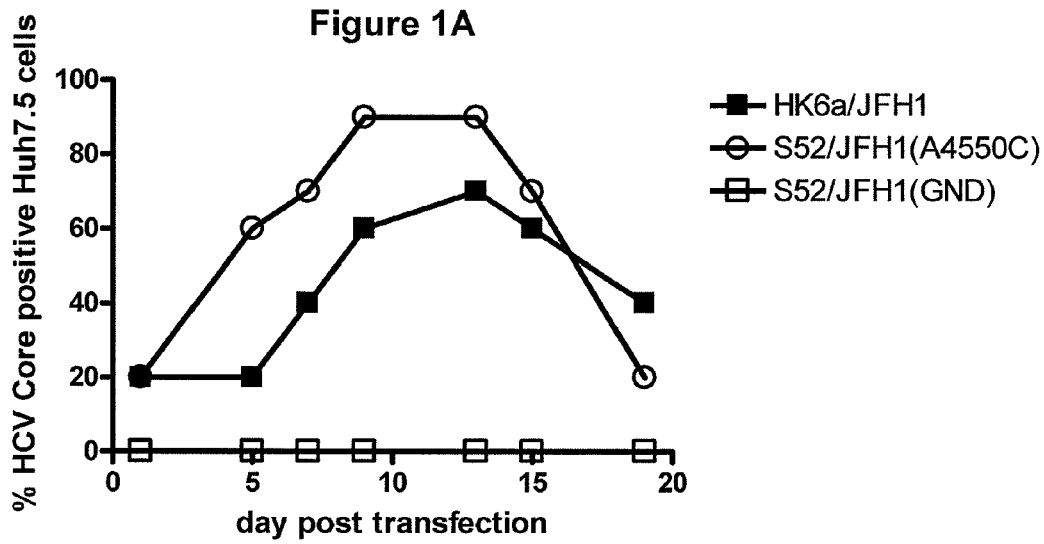
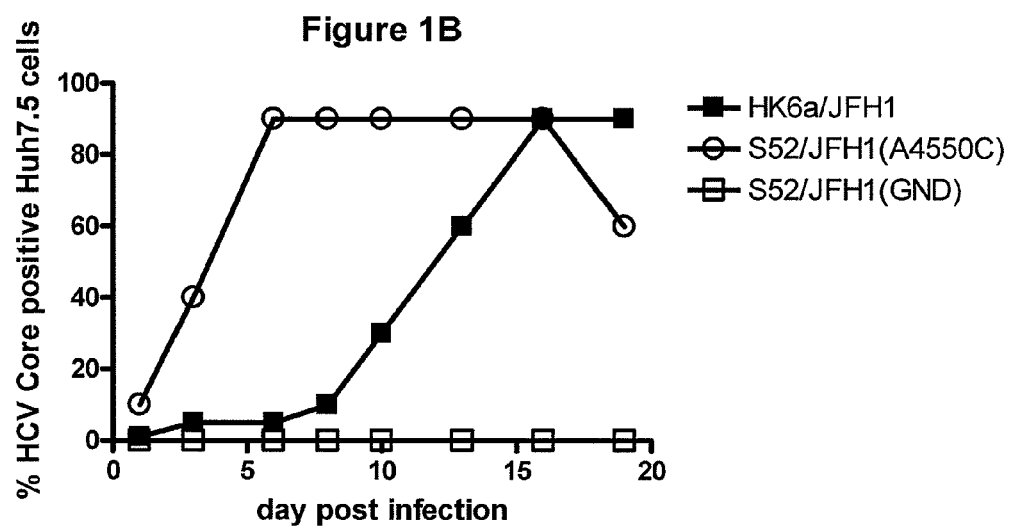

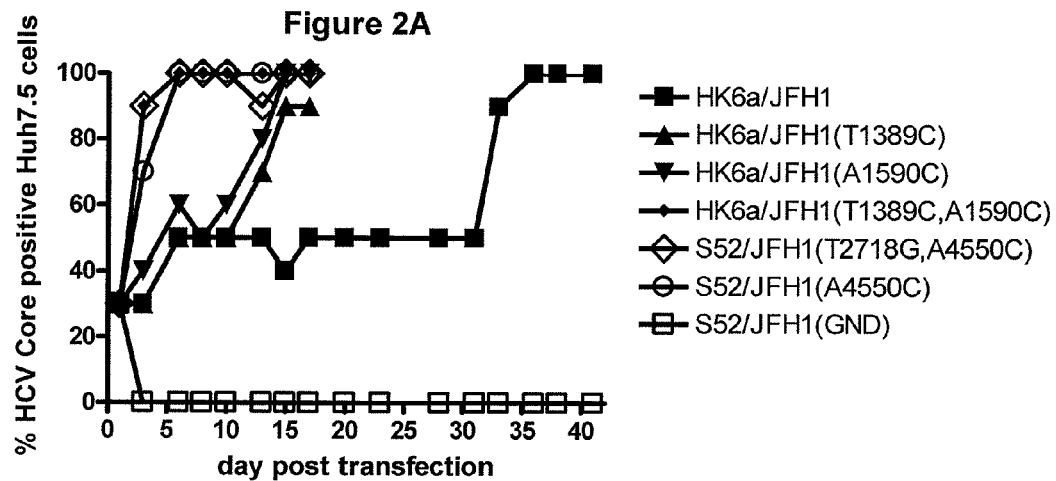
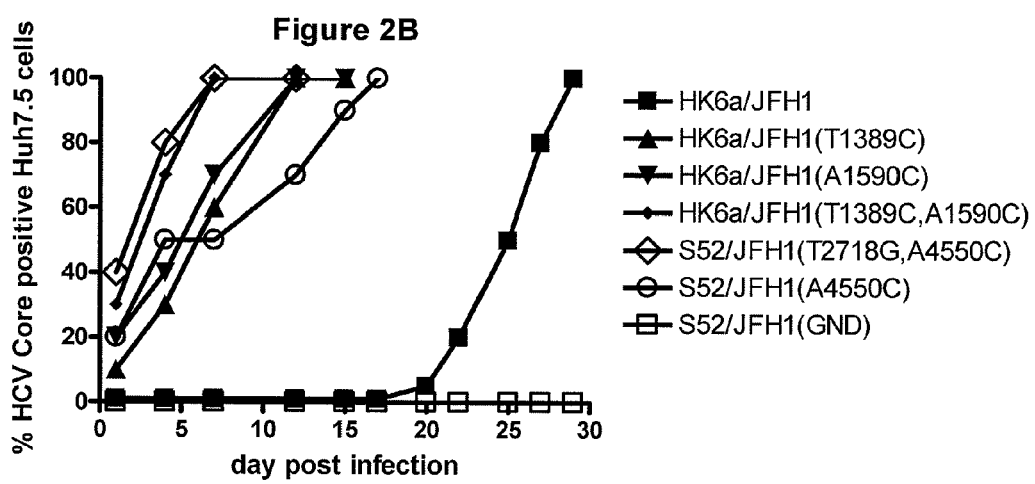

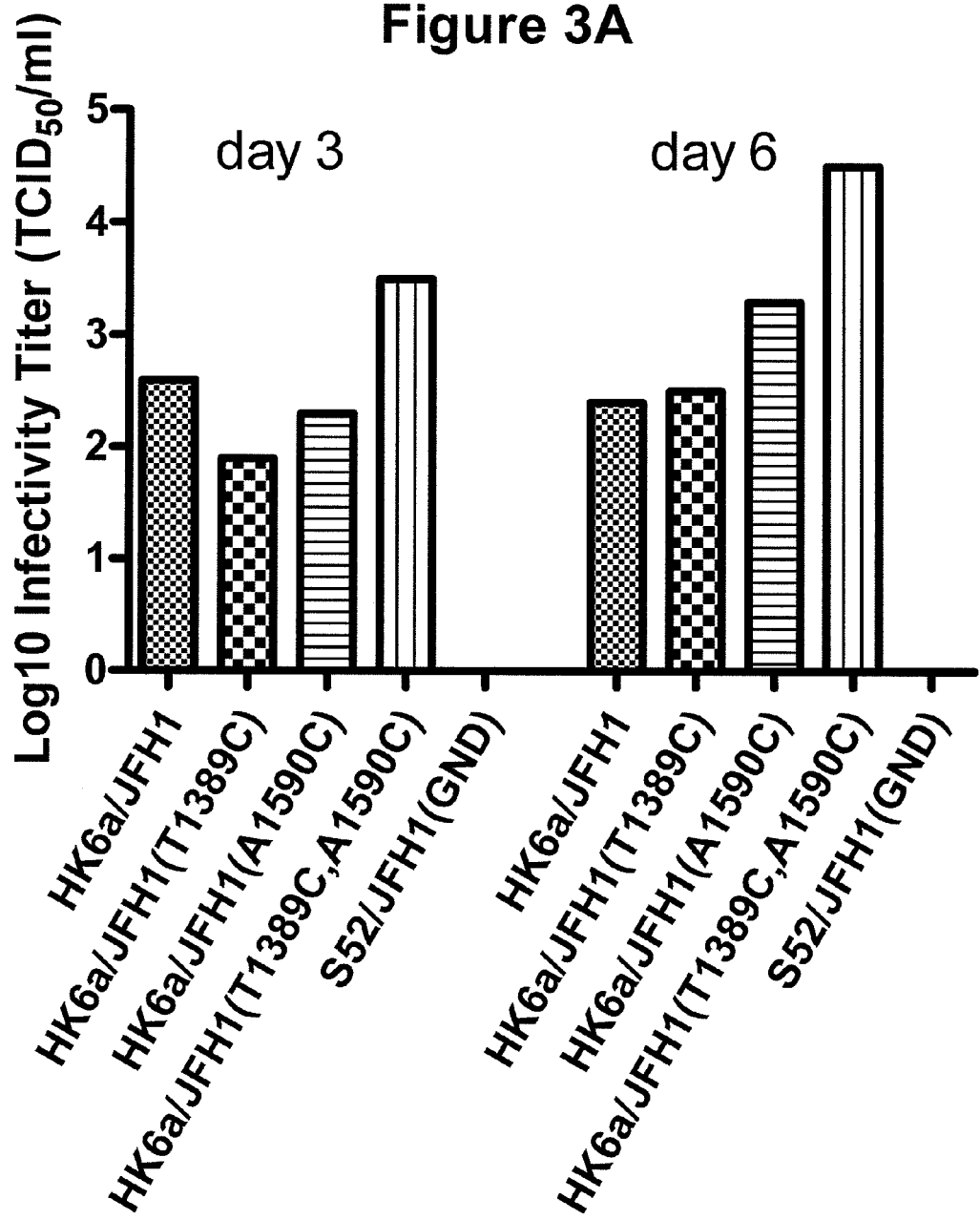

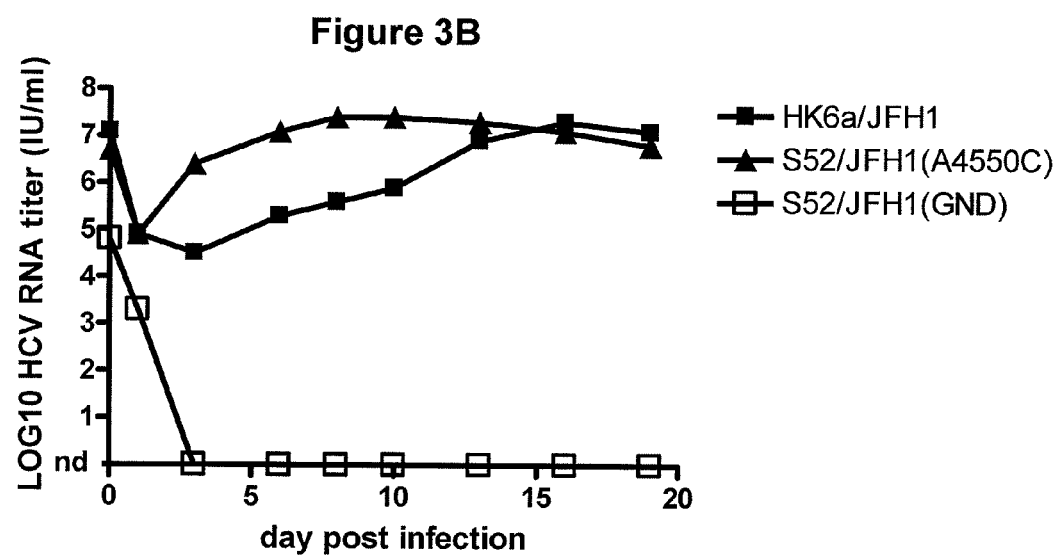

EFFICIENT CELL CULTURE SYSTEM FOR HEPATITIS C VIRUS GENOTYPE 6A

CROSS-REFERENCE TO RELATED APPLICATIONS

The present application is a National Stage application of International Patent Application No PCT/DK2008/050332, filed Dec. 19, 2008 and incorporated herein by reference in its entirety, which claims the benefit of European Application No. EP 07123851.3, filed Dec. 20, 2007; European Application No. EP 07123825.7, filed Dec. 20, 2007; and European Application No. EP 08162466.0, filed Aug. 15, 2008 each of which are incorporated herein by reference in their entireties.

INCORPORATION OF SEQUENCE LISTING

A computer readable form of the Sequence Listing named "66146_90586 SEQ LST.txt" and which is 123786 bytes in size, is electronically filed herewith and herein incorporated by reference in its entirety. This Sequence Listing consists of SEQ ID NOs: 1-32.

FIELD OF THE INVENTION

The present invention provides infectious recombinant hepatitis C genotype 6 viruses (HCV), and vectors, cells and animals comprising the same. The present invention provides methods of producing the infectious recombinant HCV genotype 6, and their use in identifying anti-HCV therapeutics including use in vaccines and diagnostics, as well as sequences of HCV associated with HCV pathogenesis.

BACKGROUND

Hepatitis C is one of the most widespread infectious diseases in the world. About 180 million people are infected with hepatitis C virus (HCV) worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 7 major HCV genotypes (genotypes 1-7) have been identified, which differ by 31-33% at the nucleotide level and deduced amino acid level. In addition, there are numerous subtypes (a, b, c, etc.) which differ by 20-25% on the nucleotide and deduced amino acid level.

While HCV genotypes 1-3 predominate in the Western World, genotypes 4-6 are more common in areas with high prevalence or even endemic levels of HCV infection. Genotype 6 is highly prevalent in Southeast Asia. A broad genetic heterogeneity of genotype 6 isolates in Southeast Asia indicates that genotype 6 has been spreading there for a long time and has been transmitted by various routes. Recently, a genotype 7a was discovered in Canadian and Belgian patients, who presumably were infected in Central Africa.

While the only approved treatment for chronic HCV infection, combination therapy with interferon-α and ribavirin, leads to a sustained virologic response in most of genotype 2 or 3 patients, viral clearance is only obtained for about half of patients with genotype 1 or 4; the few data that are available suggest an intermediate sensitivity of genotype 6 towards treatment (Hui et al., 2003). There is no vaccine against HCV.

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described, which yielded high RNA titers in the replicon system without adaptive mutations.

A major breakthrough occurred in 2005, when formation of infectious viral particles was reported after transfection of RNA transcripts from the JFH1 full-length consensus cDNA clone into Huh7 cells.

At the same time, Lindenbach et al. demonstrated that the intragenotypic 2a/2a recombinant genome (J6/JFH1), in which the structural genes (C, E1, E2), p7 and NS2 of JFH1 were replaced by the respective genes of clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo.

Despite the importance of the described cell culture systems they represent only a single subtype (genotype 2a) of HCV. It is important to develop cell culture systems for representative strains of other HCV genotypes, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as neutralizing antibodies, fusion inhibitors, ion-channel blockers and protease inhibitors, it would be sufficient to construct intergenotypic recombinant viruses in analogy to J6/JFH.

Pietschmann et al. 2006 disclose construction and characterization of infectious intra- and intergenotypic hepatitis C virus recombinants. The authors created a series of recombinant genomes allowing production of infectious genotype 1a, 1b, 2a and 3a particles by constructing intra- and intergenotypic recombinant genomes between the JFH1 isolate and the HCV isolates: H77 (genotype 1a), Con1 (genotype 1b), J6 (genotype 2a) and 452 (genotype 3a) respectively. Thus, disclosing genotypes completely different from the genotype disclosed in the present application.

The infectious titres of the 1a, 1b and 3a genotypes disclosed in Pietschmann et al. 2006 are not at a level sufficiently high for practical utilization in functional analysis, drug and vaccine development or other applications. For such applications, including screening of potential drugs and development of potential vaccine candidates, the skilled person will know that infectivity titers below $10^3$ TCID50/mL contain insufficient amounts of infectious virus.

Accordingly, the study does not attempt cell culture adaptation of the genotype recombinants, e.g. by serial passage of cell culture derived viruses to naïve cells and it is not investigated whether adaptive mutations develop after transfection in cell culture. In fact, Pietschmann et al does not even provide any sequence data of the virus produced in the cell culture.

Similarly, Sakai et al. 2007 disclose construction of a 1a/JFH1 construct based on the TN (1a) isolate. However, this study does not demonstrate any production of infectious viral particles in culture. Neither is adaptation of the construct to cell culture demonstrated.

SUMMARY OF THE INVENTION

In this study, the present inventors used the HK6a reference isolates (genotype 6a) to construct a viable, JFH1-based genome. The present inventors passaged HK6a/JFH1 virus in cell culture and obtained both high infectivity titers, high HCV RNA titers and identified adaptive mutations required for efficient growth.

The present inventors have developed robust cell culture systems for HCV genotype 6a. This is an important advance for the study of HCV, since it permits detailed molecular studies of HCV and enhances the potential for developing broadly reactive reagents against HCV, including but not limited to small molecule drugs, antibodies and vaccines. Accordingly, the present invention may be used for individualised treatment of patients infected with one of the seven major genotypes.

In one aspect the present invention relates to a replicating RNA comprising the structural genes (Core, E1, E2), p7 and the non-structural gene NS2 of genotype 6a and the non-structural genes NS3, NS4A, NS4B, NS5A and NS5B from the JFH1 strain.

In another aspect the present invention pertains to an isolated nucleic acid molecule which encodes human hepatitis C virus of genotype 6a/JFH1, wherein said molecule is capable of expressing said virus when transfected into cells.

In yet another aspect the present invention pertains to a composition comprising a nucleic acid molecule according to the present invention, a cassette vector for cloning viral genomes, methods for producing a cell which replicates HCV 6a/JFH1 RNA and cells obtainable there from.

In another aspect the present invention pertains to methods for producing a hepatitis C virus particle, methods for in vitro producing a hepatitis C virus-infected cell.

In a further aspect the present invention pertains to methods for screening an anti-hepatitis C virus substance, hepatitis C vaccines comprising a hepatitis C virus particle, methods for producing a hepatitis C virus vaccine and antibodies against hepatitis C virus.

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

Nucleic Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA (HK6a/JFH1) comprising the structural genes (Core, E1, E2), p7 and the non-structural gene NS2 of genotype 6a (e.g. strain HK6a) and the non-structural genes NS3, NS4A, NS4B, NS5A and NS5B from the JFH1 strain (genotype 2a, genbank accession number AB047639).

Thus in one embodiment, the present invention relates to a replicating RNA comprising the structural genes (Core, E1, E2), p7 and the non-structural gene NS2 of genotype 6a and the non-structural genes NS3, NS4A, NS4B, NS5A and NS5B from the JFH1 strain.

In another embodiment the genotype 6a is of the strain HK6a.

In a further embodiment, the 6a HCV strain is HK6a, EUHK2, 6a33, 6a35, 6a61, 6a62, 6a63, 6a64, 6a65, 6a66, 6a67, 6a69, 6a72, 6a73, 6a74 or 6a77. Also covered by the present invention are genotype 6a strains, for which a name has not yet been assigned.

The invention provides an isolated nucleic acid molecule encoding an infectious recombinant HCV genome, which nucleic acids comprise an intergenotypic HCV genome. In one embodiment, the intergenotypic HCV genome comprises sequences encoding structural genes (Core, E1, E2), p7 and nonstructural genes (NS2) from a first HCV strain, and sequences encoding the 5' untranslated region (UTR), non-structural genes NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain HK6a, and in another embodiment, the second HCV strain is strain JFH1.

In one embodiment, the HCV nucleic acid molecule of the present invention comprises the nucleic acid sequence (cDNA) of HK6a/JFH1, SEQ ID NO: 1. In another embodiment the nucleic acid molecule has at least a functional portion of a sequence as shown in SEQ ID NO: 1, which represents a specific embodiment of the present invention exemplified herein.

In yet an embodiment the nucleic acid molecule comprises the nucleic acid sequence of SEQ ID NO: 1.

In yet an embodiment the nucleic acid molecule comprises the nucleic acid sequence with a sequence identity of at least 90% to that of SEQ ID NO: 1.

In another embodiment, the nucleic acid comprises a sequence sharing of at least 90% identity with that set forth in SEQ ID NO: 1, such as 90% identity, 91% identity, 92% identity, 93% identity, 94% identity, 95% identity, 96% identity, 97% identity, 98% identity, or 99% identity.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO: 1 is a DNA sequence, the present invention contemplates the corresponding RNA sequence, and DNA and RNA complementary sequences as well.

In a further embodiment the present invention pertains to a an isolated nucleic acid molecule which encodes human hepatitis C virus of genotype 6a/JFH1, wherein said molecule is capable of expressing said virus when transfected into cells and wherein said molecule encodes the amino acid sequence with a sequence identity of at least 90% to that of SEQ ID NO: 1 and wherein the genotype 6a is strain Hk6a.

In a further embodiment, a region from an HCV isolate is substituted for a corresponding region, e.g., of an HCV nucleic acid having a sequence of SEQ ID NO: 1.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 1. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 1 or the said nucleic acid sequence with any mutation described in this document is obtained by any other means than what is described above.

In another embodiment, the complementary DNA (cDNA) provided by the present invention encodes human hepatitis C virus of genotype 6a/JFH1, wherein said molecule is capable of expressing said virus when transfected into cells and further capable of infectivity in vivo and wherein said molecule encodes the amino acid sequence of HK6a/JFH1, SEQ ID NO: 2.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the second or third base of a codon that encodes the same amino acid) are incorporated as markers of specific HCV clones.

Thus, one aspect of the present invention relates to any of the amino acid sequences disclosed herein, such as but not limited to SEQ ID NO: 2.

In yet an embodiment the isolated nucleic acid molecule encodes the amino acid sequence with a sequence identity of at least 90% to that of SEQ ID NO: 2.

In an embodiment the isolated nucleic acid encodes human hepatitis C virus of genotype 6a/JFH1, wherein said molecule is capable of expressing said virus when transfected into cells and wherein said molecule encodes the amino acid sequence with a sequence identity of at least 90% to that of SEQ ID NO: 2.

In another embodiment, the amino acid sequence comprises a sequence sharing at least 90% identity with that set forth in SEQ ID NO: 2, such as 91% identity, 92% identity, 93% identity, 94% identity, 95% identity, 96% identity, 97% identity, 98% identity, or 99% identity.

It is to be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

For efficient growth characteristics of HK6a/JFH1a combination of one mutation in E1 with another mutation in E2 has been shown to be of importance. In two independent transfection experiments (FIGS. 1A and 2A) T1389C in E1 was selected (Table 1). This mutation was either combined with A1590C or T1581C and A1586G in E2 (Table 1). Further evidence for the necessity of the combination of one mutation in E1 with another one in E2 comes from transfection experiments with mutated HK6a/JFH1 genomes. HK6a/JFH1 (T1389C) (SEQ ID NO: 3 and 4) $1^{st}$ passage viruses acquired A1590C (or T1581G) in a first transfection experiment and T1581C, A1586G and A1590C in a $2^{nd}$ transfection experiment (Table 1B). In two independent transfection experiments, HK6a/JFH1(A1590C) (SEQ ID NO: 5 and 6) $1^{st}$ passage viruses acquired T1389C. In contrast, HK6a/JFH1 (T1389C, A1590C) viruses did not acquire additional adaptive mutations in two $1^{st}$ passages following the $1^{st}$ transfection and one $1^{st}$ passage following the $2^{nd}$ transfection (Table 1B). Direct sequencing data derived from the $1^{st}$ passage experiment carried out after a $2^{nd}$ transfection with HK6a/JFH1 (FIG. 2B) indicate, that another set of mutations in E1 and E2 (A1408G; A1499G) might be able to substitute for the previously described combination (Table 1). HCV envelope proteins E1 and E2 are prime mediators of virus entry into the cell. Therefore, it seems very likely, that the described adaptive mutations facilitate entry of HK6a/JFH1. Because E1 and E2 interact during entry, one of the mutations might provide the main mechanism of cell culture adaptation, whereas the other one restores E1/E2 interaction.

One embodiment of the present invention relates to adaptive mutations, wherein the adaptive mutation is a mutation that can be observed by clonal or direct sequencing of recovered replicating genomes of SEQ ID NO: 1.

Thus in a further embodiment, the present invention relates to nucleic acid molecules according to the present invention, wherein said molecule comprises one or more adaptive mutations in E1, E2, NS2, NS3 or NS5A singly or in combination.

In the context of the present invention the term "adaptive mutation" is meant to cover mutations identified in passaged HK6a/JFH1 viruses that provide the original HK6a/JFH1 and any other HCV sequence the ability to grow efficiently in culture. Furthermore all introductions of mutations into the HK6a/JFH1 sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins. This also includes other HCV genomes with adaptive mutations, all of them, combinations of them or individual mutations that grow in culture. In this case the titers might be lower than those listed.

It should be understood that any feature and/or aspect discussed above in connection with the mutations according to the invention apply by analogy to both single mutations and any combination of the mutations.

One embodiment of the present invention relates to adaptive mutations, wherein said adaptive mutation is at least one of the replacements of the first said nucleotide at the said position of SEQ ID NO: 1 by the following said nucleotide selected from the group consisting of T1389C, G1394A, A1408G, A1499G, C1577G, T1581C, T1581G, A1586G, A1590C, A2865G, T3319C, G4555A, A7074G, G7085A, A7134G, T7188C, C7368T, A7384G and C7434T One embodiment of the present invention relates to adaptive mutations, wherein said adaptive mutation is at least one of the replacements of the first said nucleotide at the said position of SEQ ID NO: 1 by the following said nucleotide selected from the group consisting of T1389C, G1394A, A1408G, A1499G, C1577G, T1581C, T1581G, A1586G and A1590C.

One embodiment of the present invention relates to adaptive mutations, wherein said adaptive mutation is at least one of the replacements of the first said nucleotide at the said position of SEQ ID NO: 1 by the following said nucleotide selected from the group consisting of T1389C and A1590C.

One embodiment of the present invention relates to adaptive mutations, wherein said adaptive mutation is a replacement of T in position 1389 of SEQ ID NO: 1 with C (SEQ ID NO 3).

One embodiment of the present invention relates to adaptive mutations, wherein said adaptive mutation is a replacement of G in position 1394 of SEQ ID NO: 1 with A.

One embodiment of the present invention relates to adaptive mutations, wherein said adaptive mutation is a replacement of A in position 1408 of SEQ ID NO: 1 with G.

One embodiment of the present invention relates to adaptive mutations, wherein said adaptive mutation is a replacement of A in position 1499 of SEQ ID NO: 1 with G.

One embodiment of the present invention relates to adaptive mutations, wherein said adaptive mutation is a replacement of C in position 1577 of SEQ ID NO: 1 with G.

One embodiment of the present invention relates to adaptive mutations, wherein said adaptive mutation is a replacement of T in position 1581 of SEQ ID NO: 1 with C.

One embodiment of the present invention relates to adaptive mutations, wherein said adaptive mutation is a replacement of T in position 1581 of SEQ ID NO: 1 with G.

One embodiment of the present invention relates to adaptive mutations, wherein said adaptive mutation is a replacement of A in position 1586 of SEQ ID NO: 1 with G.

One embodiment of the present invention relates to adaptive mutations, wherein said adaptive mutation is a replacement of A in position 1590 of SEQ ID NO: 1 with C (SEQ ID NO 5).

One embodiment of the present invention relates to adaptive mutations, wherein said adaptive mutation is a replacement of A in position 2865 of SEQ ID NO: 1 with G.

One embodiment of the present invention relates to adaptive mutations, wherein said adaptive mutation is a replacement of T in position 3319 of SEQ ID NO: 1 with C.

One embodiment of the present invention relates to adaptive mutations, wherein said adaptive mutation is a replacement of G in position 4555 of SEQ ID NO: 1 with A.

One embodiment of the present invention relates to adaptive mutations, wherein said adaptive mutation is a replacement of A in position 7074 of SEQ ID NO: 1 with G.

One embodiment of the present invention relates to adaptive mutations, wherein said adaptive mutation is a replacement of G in position 7085 of SEQ ID NO: 1 with A.

One embodiment of the present invention relates to adaptive mutations, wherein said adaptive mutation is a replacement of A in position 7134 of SEQ ID NO: 1 with G.

One embodiment of the present invention relates to adaptive mutations, wherein said adaptive mutation is a replacement of T in position 7188 of SEQ ID NO: 1 with C.

One embodiment of the present invention relates to adaptive mutations, wherein said adaptive mutation is a replacement of C in position 7368 of SEQ ID NO: 1 with T.

One embodiment of the present invention relates to adaptive mutations, wherein said adaptive mutation is a replacement of A in position 7384 of SEQ ID NO: 1 with G.

One embodiment of the present invention relates to adaptive mutations, wherein said adaptive mutation is a replacement of C in position 7434 of SEQ ID NO: 1 with T.

In another embodiment all the amino acid changes observed herein are provided by the present application. The skilled addressee can easily obtain the same amino acid change by mutating another base of the codon and hence all means of obtaining the given amino acid sequence is intended.

One embodiment of the present invention relates to adaptive mutations, wherein said adaptive mutation is at least one of the replacements of the first said amino acid at the said position of SEQ ID NO: 2 by the following said amino acid selected from the group consisting of F350S, G352S, I356M, T387A, L413V, I414T, I414S, T416A, N417T, K842R, Q2245R, E2249K, E2265G, F2283S, S2343L, and S2365L.

One embodiment of the present invention relates to adaptive mutations, wherein said adaptive mutation is at least one of the replacements of the first said amino acid at the said position of SEQ ID NO: 2 by the following said amino acid selected from the group consisting of F350S, G352S, I356M, T387A, L413V, I414T, I414S, T416A, and N417T.

One embodiment of the present invention relates to adaptive mutations, wherein said adaptive mutation is at least one of the replacements of the first said amino acid at the said position of SEQ ID NO: 2 by the following said amino acid selected from the group consisting of F350S and N417T.

Another embodiment of the present invention relates said adaptive mutation is a replacement of F in position 350 of SEQ ID NO: 2 with S (SEQ ID NO 4).

Another embodiment of the present invention relates said adaptive mutation is a replacement of G in position 352 of SEQ ID NO: 2 with S.

Another embodiment of the present invention relates said adaptive mutation is a replacement of I in position 356 of SEQ ID NO: 2 with M.

Another embodiment of the present invention relates said adaptive mutation is a replacement of T in position 387 of SEQ ID NO: 2 with A.

Another embodiment of the present invention relates said adaptive mutation is a replacement of L in position 413 of SEQ ID NO: 2 with V.

Another embodiment of the present invention relates said adaptive mutation is a replacement of I in position 414 of SEQ ID NO: 2 with T.

Another embodiment of the present invention relates said adaptive mutation is a replacement of I in position 414 of SEQ ID NO: 2 with S.

Another embodiment of the present invention relates said adaptive mutation is a replacement of T in position 416 of SEQ ID NO: 2 with A.

Another embodiment of the present invention relates said adaptive mutation is a replacement of N in position 417 of SEQ ID NO: 2 with T (SEQ ID NO 6).

Another embodiment of the present invention relates said adaptive mutation is a replacement of K in position 842 of SEQ ID NO: 2 with R.

Another embodiment of the present invention relates said adaptive mutation is a replacement of Q in position 2245 of SEQ ID NO: 2 with R.

Another embodiment of the present invention relates said adaptive mutation is a replacement of E in position 2249 of SEQ ID NO: 2 with K.

Another embodiment of the present invention relates said adaptive mutation is a replacement of E in position 2265 of SEQ ID NO: 2 with G.

Another embodiment of the present invention relates said adaptive mutation is a replacement of F in position 2283 of SEQ ID NO: 2 with S.

Another embodiment of the present invention relates said adaptive mutation is a replacement of S in position 2343 of SEQ ID NO: 2 with L.

Another embodiment of the present invention relates said adaptive mutation is a replacement of S in position 2365 of SEQ ID NO: 2 with L.

Transfer of Adaptive Mutations Across Isolates, Subtypes and Genotypes.

In one embodiment the present invention relates to the transfer of adaptive mutations previously and presently identified for one isolate to another isolate of the same subtype.

In another embodiment the present invention relates to the transfer of adaptive mutations previously and presently identified for one subtype to another subtype of the same genotype.

In a further embodiment the present invention relates to the transfer of adaptive mutations previously and presently identified for one genotype to another genotype.

In the present context the term "genotype" is to be understood in accordance with Simmonds et al. 2005—i.e. the term "genotype" relate to the presently 7 identified major HCV genotypes. The terms "genotype" and "major genotype" are used herein interchangeably.

In the present context the term "subtype" is to be understood in accordance with Simmonds et al. 2005—in relation to genotype 6, this means, the presently identified subtypes indicated by lower-case letters; 6a, 6b, 6c etc (Simmonds et al. 2005).

In the present context the term "isolate" is to be understood in accordance with Simmonds et al. 2005—in relation to subtype 6a this means for example HK6a and EUHK2. Several different isolates/strains exist within the same subtype. The terms "isolate" and "strain" are used herein interchangeably.

In an embodiment the present invention pertains to a method to increase the infectivity titer, said method comprising the steps of:
 (i) identifying one or more adaptive mutation(s) in one isolate, subtype or genotype
 (ii) transferring said adaptive mutation(s) to an isolate, subtype or genotype different from the isolate, subtype or genotype in step (i)
 (iii) determining the infectivity titer in the isolate, subtype or genotype in step (ii)
 (iv) determining a reference level by determining the infectivity titer in the wild type construct without the given adaptive mutation(s)
 (v) comparing the determined infectivity titer with the reference level (vi) determining the infectivity titer as increased if the determined infectivity titer is at or above the reference level.

Titer

To determine the efficiency of the developed system, HCV RNA titers are determined in IU/ml (international units/ml) with Taq-Man Real-Time-PCR and infectious titers are determined with a 50% tissue culture infectious dose method. This titer shows the dilution of the examined viral stock, at which 50% of the replicate cell cultures used in the assay become infected and is given in $TCID_{50}$/ml. Alternatively the infectious titers are determined as FFU/ml (focus forming unites/ml); in this method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and $TCID_{50}$ or FFU per ml, respectively) or intracellularly, in lysates of pelleted cells (given as IU and $TCID_{50}$ or FFU related to a given cell number, which was lysed) (Table 5).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (Bacillus Calmette-Guerin) and *Corynebacterium parvum*. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 6a/JFH1 RNA and produces a virus particle comprising introducing the said RNA according to the invention into a cell.

In one embodiment the 6a strain is HK6a.

In another embodiment the 6a strain is selected from the group consisting of EUHK2, 6a33, 6a35, 6a61, 6a62, 6a63, 6a64, 6a65, 6a66, 6a67, 6a69, 6a72, 6a73, 6a74 and 6a77. Also covered by the present invention are genotype 6a strains, for which a name has not yet been assigned.

In a further embodiment the present invention pertains to a method for producing a cell, which replicates an RNA comprising the structural genes (Core, E1, E2), p7 and the non-structural gene NS2 of genotype 6a strain HK6a and the non-structural genes NS3, NS4A, NS4B, NS5A and NS5B from the JFH1 strain and produces a virus particle comprising introducing the said RNA into a cell wherein said RNA encodes an amino acid sequence comprising one or more adaptive mutations.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein. Such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, −4, −6 or −9 and the low-density lipoprotein receptor.

In treatment of genotype 1-6 recombinants with drugs currently used for HCV therapy, the present inventors found an antiviral effect for interferon-$\alpha$2b (FIGS. 5A, B), but not ribavirin (FIGS. 5C, D) and amantadine (FIGS. 5E, F). This is in line with previous studies, in which interferon decreased replication of J6/JFH, whereas ribavirin and amantadine did not decrease production of infectious virus in JFH1 cultures or cultures with genotype 1a (H77), 1b (Con1) or 2a (J6) JFH1-based recombinants. Genotype specific susceptibility to interferon-$\alpha$2 in patients was attributed different genome regions, especially in E2 and NS5A.

Figure 6:
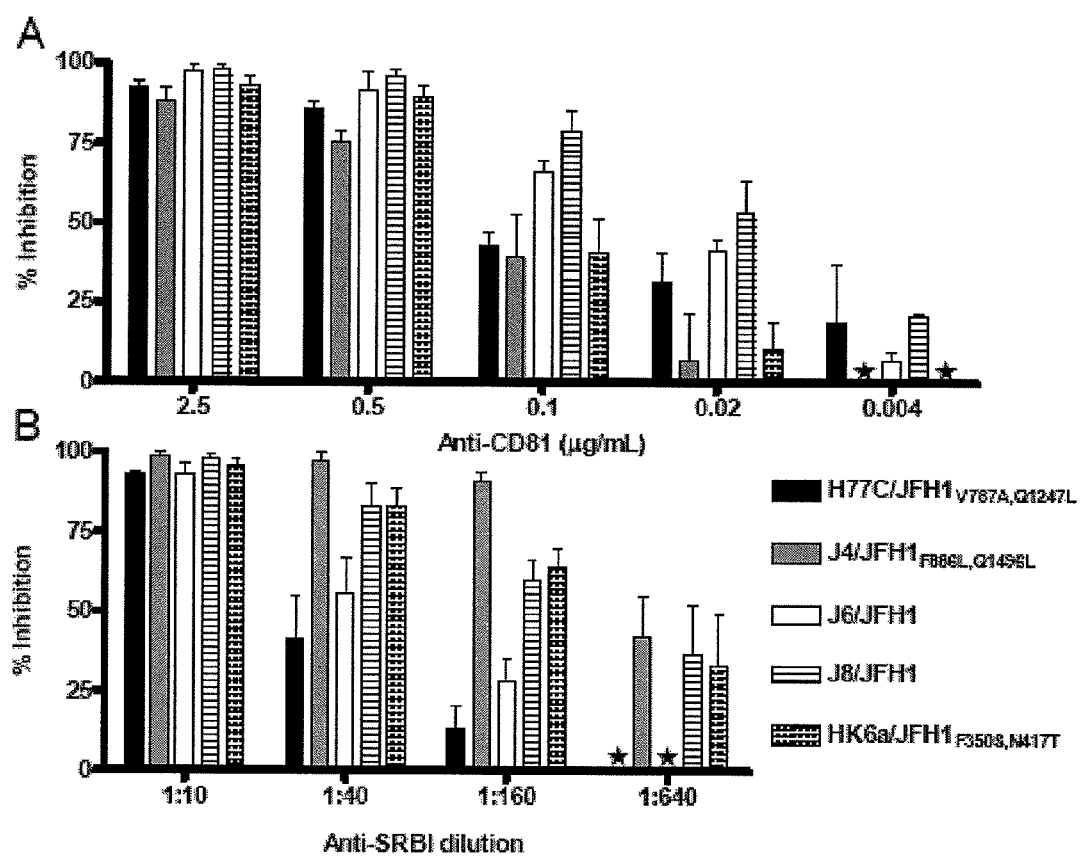

Importance of CD81 for HCV entry has in previous studies been shown for pseudoviral particles (HCVpp) of genotypes 1-6, and for cell culture derived HCV (HCVcc) of genotypes 1a (H77), 1b (Con-1), 3a (S52), 4a (ED43) and 5a (SA13). Blocking of SR-BI receptors was found to inhibit infection with HCVpp of genotypes 1-6. In the HCVcc system, genotypes 2a and 5a in previous studies depended on SR-BI. In comparative studies, the present investigators showed that entry of genotypes 1, 2 and 6 was efficiently inhibited when relative high doses of blocking antibodies against the respective HCV co-receptor were used (FIG. 6). Thus, CD81 and SR-BI play an important role for entry of prototype isolates of the six major genotypes and important subtypes 1b and 2b. Future studies will be required to determine if the different levels of inhibition seen at lower antibody doses are due to stochastical effects or indicate different modes of entry.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further it will be important to determine the viability of the developed viruses in vivo, either in SCID-uPA mice engrafted with human liver tissue or in chimpanzees.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics. Genomes with the original HK6a Core could be applied to examine genotype 6a specific features of Core.

The systems developed in this invention are ideal candidates for genotype 6a specific testing of therapeutics in general and therapeutics targeting viral entry, assembly and release. Genomes with the HK6a sequences are valuable for testing of neutralizing antibodies and other drugs acting on entry level, such as fusion inhibitors.

The present inventors conducted cross-genotype neutralization studies in HCV cell culture systems recapitulating the entire viral life cycle using JFH1-based viruses with envelope sequences of all 6 major genotypes, which has previously not been possible. HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments.

In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that JFH1-based viruses of genotype 1a, 1b, 2b, 4a, 5a and 6a, 7a were efficiently neutralized by chronic phase H06 genotype 1a serum derived from reference Patient H (Table 2). The results in the cell culture systems compare well to neutralization experiments using Patient H serum from year 26 (H03) carried out in HCVpp systems with envelope proteins of the same prototype isolates of all 6 HCV genotypes as used in the present application, and heterogeneity between the genotypes is thus as previously reported by Meunier et al. 2005.

In addition the present inventors found that cross-genotype neutralization extended to a chronic phase genotype 4a serum (AA), which efficiently neutralized genotype 2b, 4a, 5a and 6a and 7a and to a lesser extent 1a and 1b (Table 2). Also, the cross-genotype neutralization extended to a chronic phase genotype 5a serum (SA3), which efficiently neutralized genotype 2b, 4a, 5a, 6a and 7a (Table 2). Accordingly, the JFH1-based cell culture systems which have been developed for HCV genotype 1a/1b, 2a/2b, 3a, 4a, 5a, 6a and 7a provide a valuable tool for efficiently screening for and identifying new candidate HCV genotype 1a/1b, 2a/2b, 3a, 4a, 5a, 6a and 7a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the seven major genotypes enables the development of inactivated whole virus vaccines and comprehensive virus neutralization studies.

Accordingly, the JFH1-based cell culture systems which has been developed for HCV genotype 1a/1b, 2a/2b, 3a, 4a, 5a, 6a and 7a provides a valuable tool for efficiently screening for and identifying new candidate HCV genotype 1a/1b, 2a/2b, 3a, 4a, 5a, 6a and 7a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the seven major genotypes enables the development of inactivated whole virus vaccines and comprehensive virus neutralization studies.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 1a/1b, 2a/2b, 3a, 4a, 5a 6a and/or 7a inhibitors or neutralizing antibodies, comprising
　a) culturing at least one selected from the group consisting of a cell according to the present invention, a hepatitis C virus infected cell according to the present invention and a hepatitis C virus particle obtainable by the present invention together with a hepatitis C virus permissive cell, and
　b) subjecting said virus or virus infected cell culture to a blood sample or derivatives thereof from a HCV genotype 1a/1b, 2a/2b, 3a, 4a, 5a, 6a and/or 7a infected patient
　c) detecting the amount of replicating RNA and/or the virus particles.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Figure 5:
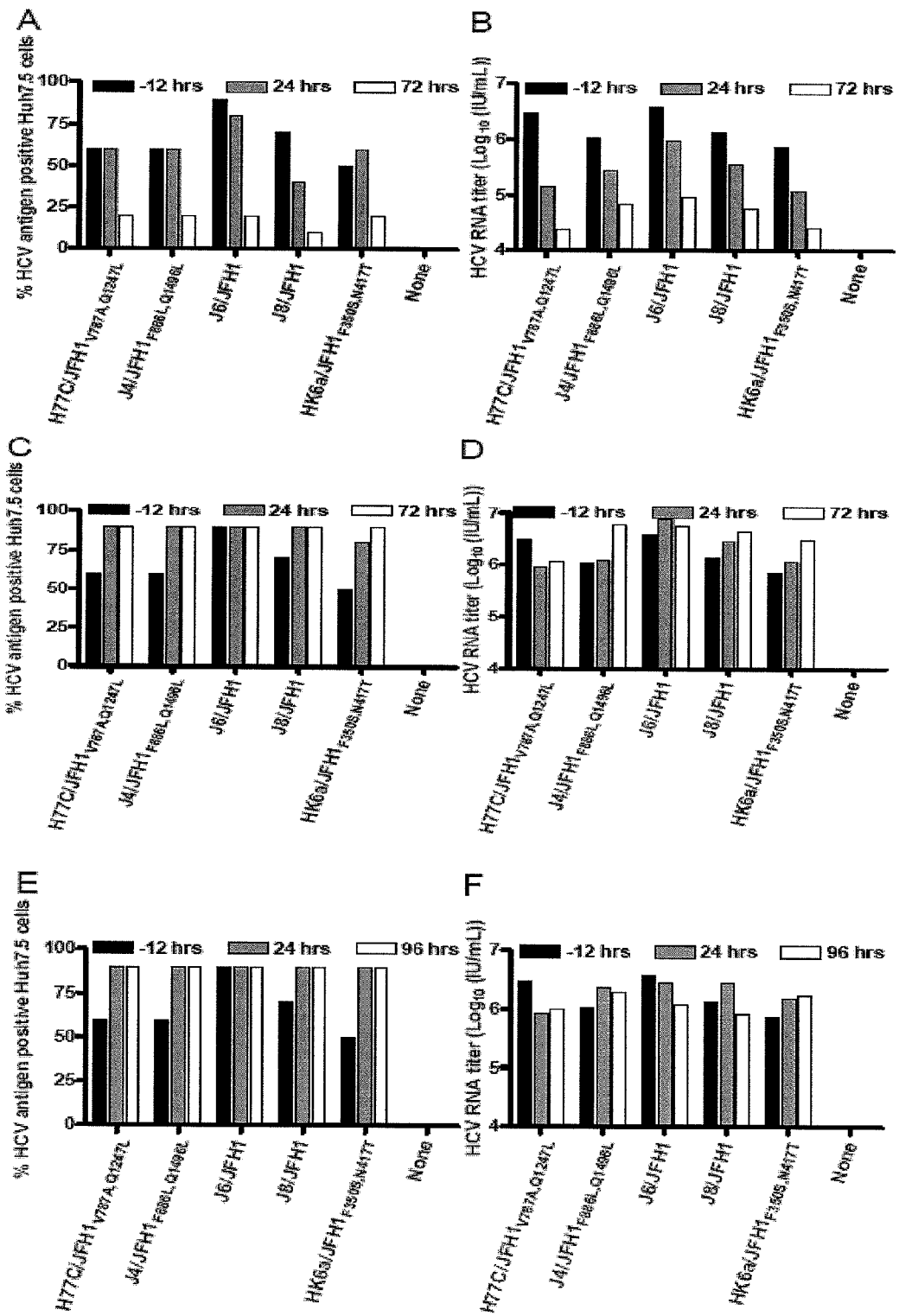

The inventors of the present invention showed that JFH1-based viruses can be used for testing putative anti-HCV antivirals. Huh7.5 cultures infected with JFH1-based recombinants of genotypes 1a, 1b, 2a, 2b, and 6a were treated with 500 IU/mL interferon-α2b (FIG. 5 A,B), 20 µM ribavirin (FIG. 5 C, D) or 50 µM amantadine (FIG. 5 E, F), respectively. A combination of interferon-α2b and ribavirin is the only currently licensed treatment of HCV infected patients. While sustained viral response (SVR) can be achieved in 80-90% of genotype 2 and 3 infected patients treated with this combination therapy, SVR is only seen in 40-50% of genotype 1 and 4 infected patients. Sequence differences of several genome regions, especially E2 and NS5A, are suggested to be responsible for this differential response. The ion-channel blocker amantadine is used in treatment of influenza and has been suggested to block HCV p7. At the tested concentrations, no significant cytotoxic effect was observed. After 72 hrs of interferon-α2b treatment, an >60% decrease in the number of infected cells and a ~2 log decrease in supernatant HCV RNA titers was observed (FIG. 5 A, B). Treatment with ribavirin and amantadine had no apparent effect (FIGS. 5 C-F). This is in line with previous studies, in which interferon decreased replication of J6/JFH, whereas ribavirin and amantadine did not decrease production of infectious virus in JFH1 cultures or cultures with genotype 1a (H77), 1b (Con1) or 2a (J6) JFH1-based recombinants. Genotype specific susceptibility to interferon-α2 in patients was attributed different genome regions, especially in E2 and NS5A. With the relatively high doses used for treatment of genotype 1-6 infected cultures, genotype specific effect was observed.

Thus, one embodiment of the present invention relates to a method for screening an anti-hepatitis C virus substance, comprising
　a) culturing at least one selected from the group consisting of a cell according to the present invention, a hepatitis C virus infected cell according to the present invention and a hepatitis C virus particle obtainable by the present invention together with a hepatitis C virus permissive cell, and
　b) detecting the replicating RNA and/or the virus particles in the resulting culture.

Thus, one embodiment of the present invention relates to a method for screening an anti-hepatitis C virus substance, comprising
　a) culturing at least one selected from the group consisting of a cell according to the present invention, a hepatitis C virus infected cell according to the present invention and a hepatitis C virus particle obtainable by the present invention together with a hepatitis C virus permissive cell,
　b) subjecting said virus or virus infected cell culture to the anti-hepatitis C virus substance, and
　c) detecting the replicating RNA and/or the virus particles in the resulting culture.

The skilled addressee may use the present invention to determine whether the identified sets of mutations can confer viability to other JFH1 based intergenotypic genotype 6a recombinants, which would allow in vitro studies of any patient genotype 6a isolate of interest.

Finally, it would be interesting to elucidate the mechanism of action of the identified mutations. In principle they might enable efficient intergenotypic protein interaction and/or lead to improvement of protein function independent of these intergenotypic interactions, for example by influencing interactions with host cell proteins.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modelling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew *Tupaia belangeri chinensis*. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The genotype 6a cell culture system developed of the present invention will be a valuable tool to address different research topics. It will allow the genotype specific study of functions of the structural proteins (Core, E1, E2) as well as p7 and NS2 using reverse genetics. While the replicon systems facilitated testing of drugs interfering with replication such as NS3/4A protease and polymerase inhibitors, the system developed in this study is ideal for the genotype 6 specific testing of new drugs, such as drugs interfering with viral entry, such as fusion inhibitors, as well as assembly and release.

Accordingly the genotype 1a/1b, 2a/2b, 3a, 4a, 5a 6a and 7a developed cell culture systems allows individual patient targeting. This means that when a new potential therapeutic candidate is discovered it is possible to test this particular candidate or combination of candidates on each of the individual genotypes. Knowing which specific genotype(s) the candidate is functioning towards, it allows an individual treatment of each patient dependent on which specific genotype the patient is infected with. Furthermore these cell culture systems allow the development of antibodies and vaccines targeting individual patients.

In addition, new therapeutics targeting the putative p7 ion-channel and protease inhibitors targeting NS2 can be tested specifically for genotype 6, thus allowing individual patient targeting.

HK6a/JFH1 recombinant viruses will be well suited for screenings for broadly reactive neutralizing antibodies, thus aiding vaccine development.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., 2000.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture. In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

The developed systems can be used to quantify HCV proteins as well as their influence on and interaction with host cell factors. In the present invention, the inventors used confocal microscopy based image analysis to quantify HCV Core and NS5A protein, the amount of intracellular lipids and interaction of Core and NS5A with intracellular lipids. The inventors evaluated spread of in vitro HCV infection by quantitative confocal microscopy based imaging. In a blinded study, increasing amounts of Core and NS5A relative to the number of total cells were detected during days 3-10 for genotype 1, 2 and 6 recombinants (FIG. 4 C, D), suggesting that this methodology could be an effective tool to evaluate HCV infection in vitro. The method also readily detected a nonspecific background staining with the anti-Core antibody, whereas the anti-NS5A gave no such signal. Thus, for optimization this quantification method requires attention to the selection of antibodies for immunostaining.

The HCV lifecycle depends on the lipid metabolism and Core has been suspected to induce hepatocellular steatosis in genotype 3 patients. In the present invention, big variation in the lipid content of non-infected Huh7.5 cells was found; during 10 days, infection with genotype 1, 2 and 6 recombinants did not induce intracellular lipid accumulation (FIG. 7), and no genotype specific differences in lipid content were found at peak infection (Table 5). A short-term infection in cell culture might not induce the changes in lipid metabolism leading to steatosis in chronically infected patients. Even though the inventors analyzed an average of 660 cells per culture for each time-point, it is evident that there was variation in the lipid content in infected as well as non-infected cells, which might mask possible subtle differences in lipid content induced by HCV. Furthermore, the inventors based their analysis on quantification of fluorescent intensity to quantify the total amount of lipids in the cell cytoplasm. Thus, morphological differences of lipid droplets between infected and non-infected cells were not analysed, which has been carried out in HCV infected cells by electron microscopy and in HCV Core expressing cells by confocal microscopy.

The present inventors found HCV Core to co-localize with lipid droplets for genotype 1, 2 and 6 recombinants (FIG. 8) as described by others for genotype 2a; further, co-localization of NS5A with lipid droplets was detected for genotype 1, 2 and 6 recombinants (FIG. 8), indicating either a direct or Core-mediated association. Interestingly, the interaction of NS5A with Core was found to play an important role in regulating the early phase of HCV particle formation.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 1a/1b, 2a/2b, 3a, 4a, 5a 6a, and 7a inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference does not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

The invention will hereinafter be described by way of the following non-limiting Figures and Examples.

Sequences

| SEQ ID NO: | DNA/AMINO ACID (AA) | NAME |
| --- | --- | --- |
| SEQ ID NO: 1 | DNA | HK6a/JFH1 |
| SEQ ID NO: 2 | AA | HK6a/JFH1 |
| SEQ ID NO: 3 | DNA | HK6a(T1389C)/JFH1 |
| SEQ ID NO: 4 | AA | HK6a(T1389C)/JFH1 |
| SEQ ID NO: 5 | DNA | HK6a(A1590C)/JFH1 |
| SEQ ID NO: 6 | AA | HK6a(A1590C)/JFH1 |
| SEQ ID NO: 7 | DNA | 9470R(24)_JFH1 |
| SEQ ID NO: 8 | DNA | -285S_HCV-MOD |
| SEQ ID NO: 9 | DNA | -84S_HCV-MOD |
| SEQ ID NO: 10 | DNA | 6aR1082 |
| SEQ ID NO: 11 | DNA | 6aF569 |
| SEQ ID NO: 12 | DNA | 6aRMut1850 |
| SEQ ID NO: 13 | DNA | 6aF1572 |
| SEQ ID NO: 14 | DNA | 6aR2680 |
| SEQ ID NO: 15 | DNA | 6aF2293 |
| SEQ ID NO: 16 | DNA | R6a3404FusJFH1 |
| SEQ ID NO: 17 | DNA | 6aF3102 |
| SEQ ID NO: 18 | DNA | 4118R_JFH1 |
| SEQ ID NO: 19 | DNA | 3880S_J6 |
| SEQ ID NO: 20 | DNA | 4796R_JFH1 |
| SEQ ID NO: 21 | DNA | 4528S_J6 |
| SEQ ID NO: 22 | DNA | 5446R_JFH1 |
| SEQ ID NO: 23 | DNA | 5272S_JFH1 |
| SEQ ID NO: 24 | DNA | 6460R_J6 |
| SEQ ID NO: 25 | DNA | 6186S_JFH1 |
| SEQ ID NO: 26 | DNA | 7234R_JFH1 |
| SEQ ID NO: 27 | DNA | 6862S_JFH1 |
| SEQ ID NO: 28 | DNA | 7848R_JFH1 |
| SEQ ID NO: 29 | DNA | 7741S_J6 |
| SEQ ID NO: 30 | DNA | 8703R_JFH1 |
| SEQ ID NO: 31 | DNA | 8137S_JFH1 |
| SEQ ID NO: 32 | DNA | 9464R(24)_JFH1 |

EXAMPLES

It should be noted that nucleotide or amino acid changes are used to describe the recombinant viruses with adaptive mutations. Thus, the following names are used herein interchangeably:

HK6a/JFH1(T1389C, A1590C) and HK6a/JFH1(F350S, N417T)
HK6a/JFH1(T1389C) and HK6a/JFH1(F350S)
HK6a/JFH1(A1590C) and HK6a/JFH1(N417T)

Materials and Methods

Source of HCV

Strain HK6a, genotype 6a was recovered from a challenge plasma pool collected from an experimentally infected chimpanzee.

Construction of HK6a/JFH1 and Adapted Genomes

For construction of pHK6a/JFH1, HK6a Core-NS2 was fused to JFH1 5' UTR and NS3 using fusion PCR with Pfu DNA polymerase (Stratagene) and standard cloning procedures with appropriate restriction sites. HK6a fragments were amplified from clones derived from the plasma pool. The two JFH1 fragments used for fusion of JFH1-5' UTR/HK6a-Core and HK6a-NS2/JFH1-NS3, were amplified from plasmid pFL-J6/JFH including the EcoRI (vector sequence upstream of JFH1 5' UTR) and SpeI (in NS3 of JFH1) sites, respectively. The EcoRI/SpeI fragment of the fusion PCR product was finally inserted into pFL-J6/JFH. For construction of adapted HK6a/JFH1 genomes mutations were introduced in HK6a/JFH1 by fusion PCR and standard cloning techniques. The HCV sequence of the described plasmids was verified by sequencing of the final DNA preparation (EndoFree Plasmid Maxi Kit, Qiagen). Sequencing reactions were carried out at Macrogen Inc. (Seoul, South Korea).

In Vitro Transcription

Plasmid DNA was linearized with XbaI (New England BioLabs), gel purified (Wizard SV Gel and PCR Clean-Up System, Promega), and in vitro transcribed with T7 RNA Polymerase (Promega) for 2 hours at 37° C. The amount of RNA transcripts was estimated by standard agarose gel electrophoresis.

Culture of Huh7.5 Cell

The human hepatoma cell line Huh7.5 is an INF-α cured clone of the Huh7 hepatoma cell line, with increased HCV replication abilities. The human hepatoma cell line Huh7.5 was cultured in D-MEM+4500 mg/L Glucose+GlutaMAX-I+Pyruvate (Gibco/Invitrogen Corporation) containing 10% heat inactivated fetal bovine serum (Sigma), penicillin at 100 units/ml and streptomycin at 100 mg/ml (Gibco/Invitrogen Corporation) at 5% $CO_2$ and 37° C. Cells were split every 2nd to 3rd day at a ratio of 1:2 to 1:3. Supernatants were sterile filtered to exclude cells and debris and stored at −80° C.

Transfection and Infection of Huh7.5 Cells

Cells were washed with PBS (Dulbecco's Phosphate Buffered Saline; Sigma) and trypsinized (Trypsin/EDTA, Invitrogen). $4 \times 10^5$ cells were plated per well of a 6 well plate in D-MEM (10% FBS; without antibiotics) and cultured for 24 hrs. For transfection cells were incubated with lipofection complexes (2.5 µg RNA transcripts and 5 µl Lipofectamine 2000 (Invitrogen) in serum free medium (Opti-MEM, Invitrogen) for ~12 hrs. For infection cells were incubated with filtrated cell culture supernatants. The incubation times for different experiments are given in the figure legends. Supernatants of virus infected cell cultures or controls were rescued every 2-3 days. Cell free supernatants were aliquoted and stored at −80° C.

Negative controls in transfections were RNA transcripts from replication deficient JFH1-based genomes (with the GND motif); in the kinetic experiment (FIG. 4), non-infected cells were used (data not shown).

Viral spread was monitored by HCV Core or NS5A immunostainings with mouse anti-HCV core protein monoclonal antibody (B2) (Anogen, Yes Biotech Laboratories) or anti-NS5A, 9E10, respectively, as described in the following section. Supernatant infectivity titers were determined as 50% tissue culture infectious dose ($TCID_{50}$)/mL or as focus forming units (FFU)/mL, as described in the following section. Supernatant HCV RNA titers were measured by a 5' UTR based Real Time RT-PCR as described below.

For generation of virus stocks, Huh7.5 cells were infected at a multiplicity of infection (MOI) of ~0.003. After viral spread to >80% of the culture (Core or NS5A immunostaining), supernatants were filtered, aliquoted and stored at −80° C. Size of each viral stock was ~100 mL.

Immunostainings for HCV antigens and lipids; titration of infectivity NS5A antigen staining was carried out as previously described using 1st antibody anti-NS5A, 9E10 at 1:200 in PBS/Tween, secondary antibody ECL anti-mouse immunoglobulin (Ig)G, horseradish-peroxidase-linked whole antibody (GE Healthcare Amersham) at 1:300 in PBS/Tween, and horseradish peroxidase substrate (DAB substrate kit, DAKO). For Core antigen staining we used the mouse anti-HCV core protein monoclonal antibody (B2) (Anogen, Yes Biotech Laboratories) at 1:200 in PBS containing 5% BSA, and the 2nd antibody Alexa Fluor 594 goat anti-mouse IgG (H+L) (Invitrogen) at 1:500 in PBS/Tween; cell nuclei were counterstained with Hoechst 33342 (Invitrogen). Lipids were stained with oil red O (Fisher scientific) as described previously. Finally, slides were washed with PBS, mounted with Fluoromount-G (Southern Biotech) and cover slipped. Staining was visualized using a Leica TCS SP5 confocal microscope. Percentage of HCV positive cells was evaluated by microscopy assigning values of 0% (no cells infected), 1%, 5%, 10-90% (in steps of 10%), 95% and 100% (all cells infected).

Determination of Infectivity Titers as 50% Tissue Culture Infectious Dose ($TCID_{50}$) of focus forming units (FFU)/ml in HCV cultures $6 \times 10^3$ Huh7.5 cells were plated per well of a poly-D-lysine coated 96-well plate (Nunc). After ~24 hrs cells were incubated with 10-fold serial dilutions of viral stock cell culture supernatant. For $TCID_{50}$ determinations, 6 replicates per dilution were incubated for 2-3 days. For FFU determinations, wells were incubated for 48 rs. After incubation, cells were permeabilized for 5' with cold methanol. After washing 1× with PBS and 1× with PBS/Tween-20, blocking was carried out for 20' with sterile filtered 1% BSA/0.2% skim milk in PBS followed by a 5' blocking of endogenous peroxidase activity using 3% $H_2O_2$. Cells were washed as above and incubated with a 1:200 dilution of 1° Ab α-NS5A (9E10) in PBS/0.1% tween-20 over night at 4° C. After washing, a 1:300 dilution of 2° Ab HRP-goat anti-mouse IgG (H+L) (Amersham Biosciences) in PBS/0.1% tween-20 was added and incubated for 30' at room temperature. Staining was developed using DAB substrate kit (DAKO) for 30' after washing. In $TCID_{50}$ determinations, wells were scored positive if one or more cells were infected, and the $TCID_{50}$ was calculated according to the Reed and Muench method. $TCID_{50}$ values are derived from single or multiple determinations as indicated. FFU determinations are based on counts of wells with 5-100 FFU and three independent virus dilutions with one replicate each. However, FFU calculations for virus stocks (Table 4) were based on two independent virus dilutions with 6 replicates each.

Neutralization of Virus by Patient Sera.

~100 $TCID_{50}$ virus were incubated for 1 hour at 37° C. with 2-fold dilutions of heat inactivated (56° C. for 30 min) patient sera or a mixture of sera from four healthy controls in final dilutions as indicated. The virus-serum mixture was incubated for 3 hours at 37° C. with $6 \times 10^3$ plated Huh7.5 cells in a poly-D-lysine coated 96-well plate. Cells were washed once, supplemented with fresh media and left for 2 days before staining as described for infectivity titration. FFUs were scored as above.

Direct Sequencing of the Complete ORF of Recovered Viruses.

RT-PCR was done using SuperScriptIII (Invitrogen) and RT-primer 9470R_JFH1. In $1^{st}$ round PCR the Advantage 2 PCR Enzyme System and primers—285S_HCV-MOD and 9470R_JFH1 were used. Cycle parameters were 35 s at 99° C., 30 s at 67° C. and 10 min (cycle 1-5), 11 min (cycle 6-15), 12 min (cycle 16-25) or 13 min (cycle 26-35) at 68° C. 12~1 kb products were synthesized in overlapping nested PCRs covering the entire ORF (nt 297-9427) using primer pairs 1-12 (Table 4). Cycle parameters were 35 s at 99° C. followed by 35 cycles with 35 s at 99° C., 30 s at 67° C. and 6 min at 68° C.

Treatment, Receptor Blocking and Neutralization

For treatment, interferon-α2b (Schering-Plough), ribavirin (Sigma) or amantadine (Sigma) was used; cell viability was monitored with CellTiter 96 AQueous One Solution Cell Proliferation Assay (Promega).

For blocking of CD81 and SR-BI and neutralization assays, Huh7.5 cells were plated 6×10³ per well of a poly-D-lysine-coated 96-well plate and incubated for 24 hrs. For blocking experiments, cells were incubated with anti-CD81 (JS-81; BD Biosciences Pharmingen, Franklin Lakes, N.J.) or isotypematched control antibody (anti-human immunodeficiency virus, p24, clone Kal-1; DAKO) and rabbit polyclonal anti-SR-BI (GeneTex) or rabbit polyclonal control antibody (anti-human Retinoblastoma (Rb) Ab-6, Thermo Scientific), respectively, for 1 hr. Subsequently, cells were infected with ~150 FFU of the respective virus for 3 hrs followed by washing with PBS. After 48 hrs of incubation with normal growth medium, cells were stained for HCV NS5A to determine the number of focus forming units (FFU) per well. Experiments were performed in triplicates unless stated otherwise. Percent inhibition by anti-CD81 and anti-SR-BI was calculated by comparison to the FFU mean of at least 3 replicate wells incubated with virus only.

For neutralization, heat inactivated sera were pre-incubated with ~30-150 FFU for 1 hr at 37° C., preceding 3 hrs incubation on 6×10³ Huh7.5 cells. After 48 hrs incubation with normal growth medium, cultures were immunostained for NS5A, and the number of FFU was determined. Neutralization experiments were performed in triplicates and percent inhibition by patient sera was calculated by comparison to the FFU mean of at least 3 replicate wells incubated with virus only. Sera used for neutralization were derived for from persistently infected Patient H (2006, year 29 after infection, genotype 1a), an Egyptian Patient (AA, 1994, genotype 4a), and a South African hepatocellular carcinoma patient (SA3, genotype 5a).

Real-Time PCR Assay for Determination of HCV RNA Titers

RNA was purified from 200 µL heat-inactivated (56° C. for 30 min) cell culture supernatant using the Total Nucleic Acid Isolation Kit (Roche Applied Science) with the Total NA Variable Elution Volume protocol on a MagNA Pure LC Instrument (Roche Applied Science). As an internal control, phocine distemper virus was added. In parallel to RNA purified from culture supernatants, a quantitative HCV standard panel covering concentrations of 0-5 10⁶ IU/mL in 1-log increments (OptiQuant HCV Panel; AcroMetrix) was analyzed. Real-time PCR analyses of HCV and phocine distemper virus RNA were performed in separate reactions using TaqMan EZ reverse-transcription PCR Kit (Applied Biosystems). For HCV, primers and a 6-carboxyfluorescein-labeled minor groove binder-probe were specific for the 5=UTR and were shown previously to perform similarly against a panel of the 6 HCV genotypes in a different TaqMan assay. For phocine distemper virus, a ready-to use primer/probe mix was used (Dr H. G. M. Niesters, Erasmus Medical Centre, Rotterdam, Netherlands). PCR analysis was performed on a 7500 real-time PCR System (Applied Biosystems) using the following cycle parameters: 2 minutes at 50° C., 30 minutes at 60° C., and 5 minutes at 95° C., followed by 45 cycles of 20 seconds at 94° C. and 1 minute at 62° C. HCV RNA titers (IU/mL) were calculated using a standard curve from the standard panel and corresponding cycle threshold (Ct) values (cycle number, at which the normalized fluorescence signal increases to greater than a fixed 0.2 threshold). The reproducible detection limit was 500 IU/mL. The Ct of the phocine distemper virus reaction was compared with the expected Ct (based on a mean of previous runs; n_9) using the MedLab QC freeware program. Results of samples with a Ct within _2 SD of the expected value were accepted.

Direct Sequencing of Cell Culture Derived HCV

RNA was extracted from supernatant using High Pure Viral Nucleic Acid Kit (Roche). For analysis of the ORF of recovered HK6a/JFH1 viruses, RT-PCR was performed with primer 9470R(24)_JFH1 (Table 3) and SuperScript III (Invitrogen) for one hour at 50° C. followed by 10 min at 70° C., and RNA templates were digested by incubation with RNAseH (4 U, Invitrogen) and RNAseT1 (1000 U, Ambion) for 20 min at 37° C. First round PCR was carried out with primers −285S—HCV-MOD and 9470R(24)_JFH1 (Table 3) using BD Advantage 2 Polymerase Mix and 35 cycles of 99° C. for 35 sec, 67° C. for 30 sec and 68° C. for 10 min (5 cycles), 11 min (10 cycles), 12 min (10 cycles) and 13 min (10 cycles). In a 2nd round PCR, 12 overlapping fragments spanning the complete ORF were generated with the primer combinations shown in Table 3 with cycling parameters as above but amplification of 6 min at 68° C. for 35 cycles.

Sequence Analysis Software and Databases

Sequencing reactions were carried out at Macrogen Inc. (Seoul, South Korea). Sequence analysis was performed using Sequencher 4.6, Gene Codes Corporation and freeware BioEdit v. 7.0.5. HCV sequences used for alignments were retrieved from The European HCV database website (euHCVdb; http://euhcvdb.ibcp.fr/euHCVdb/1) and the American HCV database website (LANL; http://hcv.lanl.gov/content/hcv-db/index2).

Example 1

Cell Culture Adaptation of Intergenotypic 6a/2a Recombinant (Hk6a/JFH1)

In order to develop a cell culture system for HCV genotype 6 the present inventors developed the intergenotypic 6a/2a recombinant pHK6a/JFH1, which contains (i) the 5' UTR of the JFH1 isolate (nts 1-340) differing from the sequence provided for JFH1 (accession number AB047639) at one position (C301T); (ii) Core through NS2 of HK6a (nts 341-3436); and (iii) NS3 through 3' UTR of JFH1 (nts 3437-9684).

After two independent transfections of Huh7.5 cells with RNA transcripts of pHK6a/JFH1, a delay of viral spread was observed (determined by the increase in the percentage of cells expressing HCV Core antigen) compared to the positive control virus S52/JFH1(A4550C) (FIGS. 1A, 2A). Thus, HK6a/JFH1 spread to >50% of Huh7.5 cells after 9 and 33 days, respectively (FIGS. 1A, 2A). After one cell free passage of virus derived from the 1$^{st}$ transfection experiment (FIG. 1A) in naïve Huh7.5 cells (FIG. 1B), viral genomes derived at the peak of infection (day 16) were directly sequenced. These first passage viruses had coding nucleotide changes in E1 (T1389C coding for F350S; nucleotide and amino acid positions refer to the HK6a/JFH1 sequence) and E2 (A1590C coding for N417T) (Table 1). Clonal sequence analysis of nts 1243-1619 of the envelope proteins showed that these mutations were combined in 4/4 clones. One of four clones had the additional mutation G1394A coding for G352S (data not shown).

Example 2

Reverse Genetics Analysis of Putative Adaptive Mutations

Figure 9:
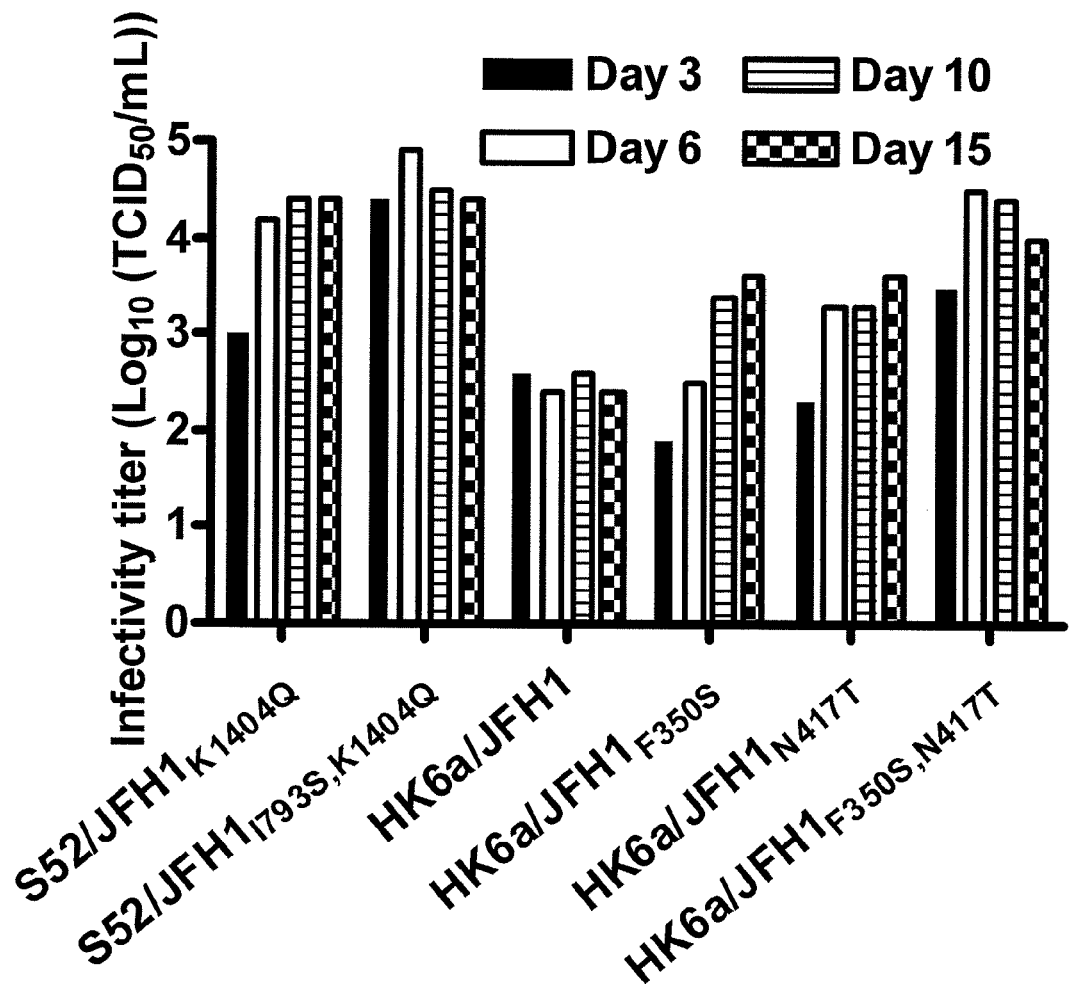

In order to prove that the identified mutations conferred cell culture adaptation, the present inventors constructed three HK6a/JFH1 recombinants containing either T1389C in E1, A1590C in E2 or a combination of both mutations. In a first transfection experiment, on day 6 after transfection, most cells in the HK6a/JFH1(T1389C, A1590C) and the positive control cultures had become HCV Core positive and showed infectivity titers of ~$10^{4+5}$ TCID50/ml. In contrast, HK6a/JFH1 viruses with the single mutations T1389C or A1590C first spread to infect most cells on day 15 when they showed infectivity titers of ~$10^{3.5}$ TCID50 (FIG. 2A and FIG. 9). Sequencing of first passage (FIG. 2B) viral genomes revealed that only HK6a/JFH1(T1389C, A1590C) was genetically stable, whereas HK6a/JFH1(A1590C) acquired T1389C and HK6a/JFH1(T1389C) acquired A1590C as a 50/50 quasispecies with the original sequence and T1581G (coding for I414S) as a minor quasispecies (Table 1).

Interestingly, in this transfection experiment, the original HK6a/JFH1 showed Core expression in ~50% of the cell culture for an extended period, before the entire culture became Core positive on day 36 after transfection (FIG. 2A). At this timepoint two coding nucleotide changes were present as a 50/50 quasispecies with the original sequence: T1389C in E1 (same change as in the 1st transfection experiment) and T1581C in E2 (coding for I414T) (Table 1). The same changes were also present in viruses derived from a first passage of this second transfection experiment (FIG. 2B, Table 1). However, apparently two other coding nucleotide changes in E1 (A1408G coding for I356M) and E2 (A1499G coding for T387A) were co-selected. Additionally, several coding and non coding nucleotide changes were observed in other genes (Table 1), which might have been selected due to the presumably low infectious dose contained in HK6a/JFH1 day 15 transfection inoculum.

Analysis of $1^{st}$ passage viral genomes derived from a second transfection experiment with HK6a/JFH1(T1389C, A1590C), HK6a/JFH1(T1389C) and HK6a/JFH1(A1590C) showed that HK6a/JFH1(T1389C, A1590C) was again genetically stable, whereas HK6a/JFH1(A1590C) acquired T1389C and HK6a/JFH1(T1389C) acquired T1581C, A1586G and A1590C as quasispecies (Table 1B).

Thus, efficient growth of HK6a/JFH1 depended on F350S in E1 in combination with E2 mutations.

Example 3

Infectivity and HCV RNA Titer Determined in HK6a/JFH1 Cultures

So far infectivity titers have been determined for cultures transfected with adapted and original HK6a/JFH1 (experiment shown in FIG. 2A). In the HK6a/JFH1(T1389C, A1590C) culture a peak titer of $10^{4.5}$ TCID$_{50}$/ml (50% tissue culture infectious dose) was determined already on day 6 post transfection (FIG. 3A, FIG. 9). In addition, a HK6a/JFH1 (T1389C, A1590C) virus stock showed an infectivity titer of $10^{4+7}$ TCID$_{50}$/ml (data not shown). HCV RNA titers were determined on the 1st passage of HK6a/JFH1 (FIG. 1B) carried out following the 1st transfection experiment (FIG. 1A) and are shown in FIG. 3B. Peak HCV RNA titers were around $10^{7.5}$ IU/ml on day 16 post infection.

Thus, peak infectivity and HCV RNA titers yielded in the HK6a/JFH1 system are comparable to the titers achieved with intergenotypic recombinants of the other major genotypes of HCV developed.

Example 4

Titrated Stocks of Intergenotypic Recombinant Viruses and Comparative Kinetic Studies The present inventors characterized supernatant virus stocks of JFH1-based intergenotypic recombinants, as well as J6/JFH (Table 4). Infectivity titers ranged from $10^{3.7}$ to $10^{5.2}$ TCID$_{50}$/mL and HCV RNA titers ranged from $10^{7.0}$ to $10^{7.6}$ IU/mL. The highest specific infectivities, defined as infectious titer relative to the HCV RNA titer were found for J6/JFH and HK6a/JFH1$_{F3SOS,N417T}$ (>1/500 TCID$_{50}$/IU). There was a good correlation between the infectivity titers determined as TCID$_{50}$/mL and FFU/mL, respectively (Table 4).

Figure 7:
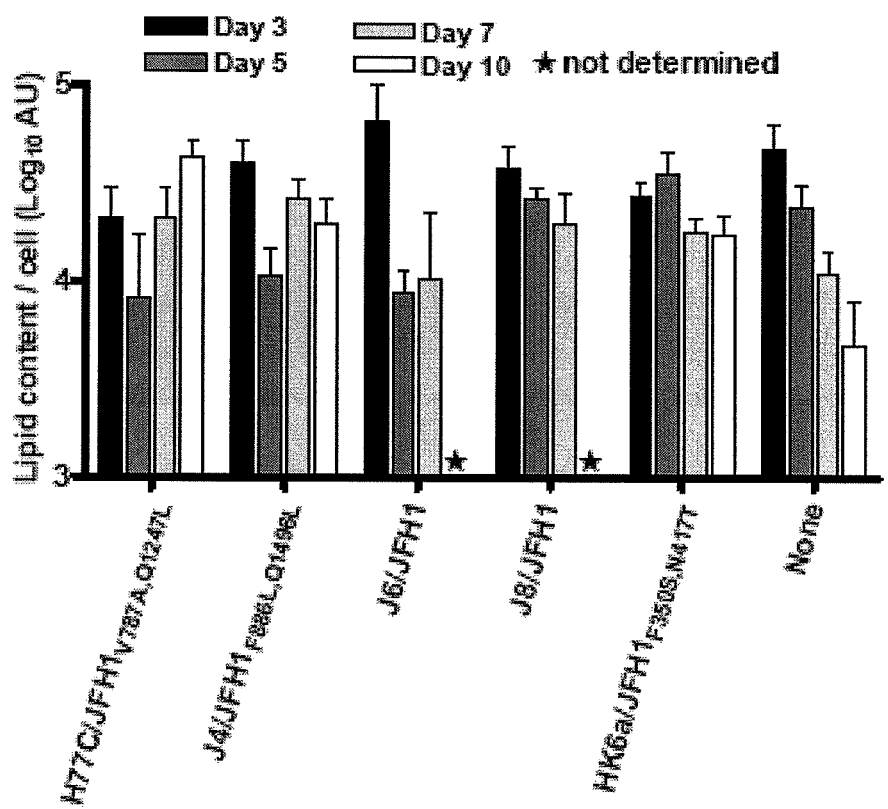

To further characterize the different genotype viruses, the present inventors performed a kinetic experiment with genotype 1a/1b, 2a/2b and 6a recombinants. After inoculation of Huh7.5 cultures with the respective stock viruses at an MOI of 0.003, efficient spread in 5-10 days was observed (FIG. 4A), paralleled by a 2-3 log increase in HCV RNA titers to peak titers of >$10^7$ IU/mL (FIG. 4B). In addition, an increase in intracellular Core and NS5A antigen by microscopy based image analyses was observed (FIGS. 4C, D). Increasing infection with genotypes 1a/1b, 2a/2b and 6 did not lead to a change in the average lipid content per cell that was greater than the range of natural variation observed for non-infected cultures (FIG. 7). At peak infection (defined as the first time point with supernatant HCV RNA titers ≥$10^7$ IU/mL), the present inventors also measured intracellular HCV RNA and intra- and extracellular infectivity titers (Table 5). Intracellular specific infectivity was at least one order of magnitude lower than extracellular specific infectivity for the respective viruses. Finally, it was found that genotype 1a/1b, 2a/2b and 6a cultures did not show significant differences in the average intracellular lipid content at the peak of infection (Table 5).

Figure 8:
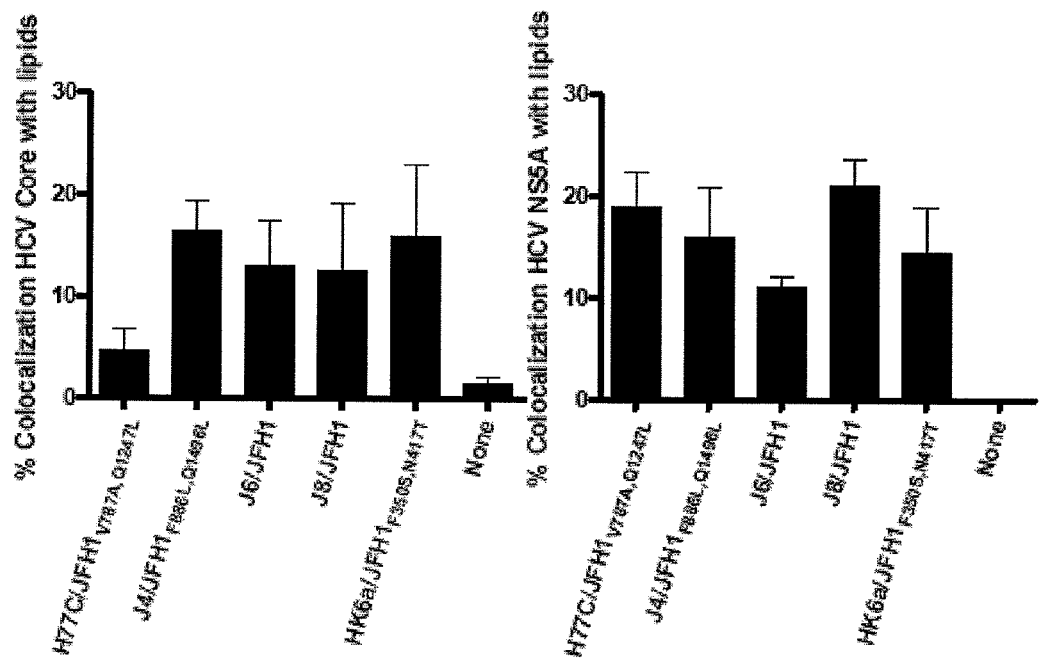

By standard confocal microscopy of genotype 1-6 infected Huh7.5 cells co-localization of lipid droplets with Core and NS5A, respectively, was observed (data not shown). Using confocal microscopy based image analyses the degree of this co-localization was determined (FIG. 8). The analysis indicated that under the set conditions (see Materials and Methods) 5-20% of HCV Core co-localized with lipid droplets with no genotype specific differences (FIG. 8). In addition, 10-40% of HCV NS5A co-localized with lipid droplets.

Example 5

Treatment with Interferon, Ribavirin and Amantadine

The present inventors investigated the therapeutic potential of drugs currently used or tested for treatment of HCV on Huh7.5 cultures infected with genotype 1a/1b, 2a/2b and 6a recombinants. Cells obtained on day 5 of the kinetic experiment (FIG. 4A) were treated with 500 IU/mL interferon-α2b (FIGS. 5A, B), 20 µM ribavirin (FIGS. 5C, D) or 50 µM amantadine (FIGS. 5E, F), respectively. No significant cytotoxic effect was observed (data not shown). After 72 hrs interferon-α2b treatment, an at least 60% decrease in the number of infected cells and a ~2 log decrease in supernatant HCV RNA titers was observed (FIGS. 5A, B). Treatment with ribavirin and amantadine did not decrease the number of infected cells or supernatant HCV RNA titers (FIGS. 5C-F). Thus, only interferon-α2b had an antiviral effect with no major differences regarding the genotype of the JFH1-based recombinants treated.

Example 6

Importance of CD81 and SR-B1 for HCV Genotype 1, 2 and 6 Infection

Infection with genotype 1a/1b, 2a/2b and 6a recombinants was blocked by anti-CD81 in a dose dependent manner (FIG.

6A); ~90% inhibition was observed at 2.5 μ/mL anti-CD81, whereas at 0.02 and/or 0.004 μg/mL anti-CD81 <50% inhibition was found. In SR-BI blocking experiments, we observed for all genotype recombinants >90% infection inhibition with a 1:10 dilution of polyclonal anti-SR-BI (FIG. 6B). This inhibition was dose dependent, and at a 1:640 dilution <50% inhibition was found for all genotype recombinants.

Example 7

Testing of Cross-Genotype Neutralization of Genotype 1-7 Recombinant Viruses with 1a, 4a and 5a Anti-Sera Chronic phase sera from patients infected with genotypes 1a (H06), 4a (AA) and 5a (SA3) with relative high neutralization titers against the homologous genotype virus was identified. The cross-genotype neutralization potential of these sera against 1a, 2a, 3a, 4a, 5a and 6a viruses were tested previously (Table 2).

These sera also showed high 50% neutralization titers against the 7a virus (Table 2). Relative high neutralization titers were found against 1b and 2b viruses with the H06 sera, whereas the AA and SA3 sera showed limited neutralization of these viruses (Table 2). It is of interest, that different subtypes as 2a and 2b show a differential susceptibility to neutralization.

FIGURE LEGENDS

FIG. 1

HK6a/JFH1 recombinants and its viability in Huh7.5 cells.

1st transfection experiment with HK6a/JFH1. $4 \times 10^5$ Huh7.5 cells were plated per well of a 6 well dish and after 24 hrs (A) transfected with 2.5 μg RNA transcripts of HK6a/JFH1, S52/JFH1(A4550C) as positive control and S52/JFH1 (GND) as negative control or (B) infected for 8 hrs with 1.9 ml of cell free supernatant derived from transfected cultures (A) on day 15. Percentages of HCV Core antigen expressing cells were determined by immunostaining and confocal microscopy.

FIG. 2

Transfection with mutated HK6a/JFH1 and 2nd transfection experiment with HK6a/JFH1.

(A) Huh7.5 cells were transfected with in vitro transcripts of mutated and original HK6a/JFH1, S52/JFH1(A4550C) and S52/JFH1(T2718G, A4550C) as positive control, and S52/JFH1(GND) as negative control. (B) Huh7.5 cells were infected for 4 hrs with 1 ml of cell free supernatant derived from transfected cultures (A): day 6 for HK6a/JFH1 (T1389C, A1590C), S52/JFH1(A4550C) and S52/JFH1 (T2718G, A4550C); day 15 for HK6a/JFH1(T1389C), HK6a/JFH1(A1590C) and HK6a/JFH1; day 10 for S52/JFH1 (GND). Percentages of HCV Core antigen expressing cells were determined by immunostaining and confocal microscopy.

FIG. 3

Infectivity and HCV RNA titers yielded by HK6a/JFH1 recombinants.

(A) Infectivity titers were determined on cell free supernatants derived on day 3 and 6 from transfection cultures shown in FIG. 2A by the 50% tissue culture infectious dose method. These data are also shown in FIG. 9. (B) HCV RNA titers were determined by 5' UTR TaqMan assay; nd=not determined.

FIG. 4

Comparative Kinetics Studies of Intergenotypic Viruses of Genotypes 1, 2 and 6

Huh7.5 cells were inoculated with the respective stock virus (Table 4) for 6 hrs (MOI 0.003); J4/JFH1$_{F886L,Q1496L}$ was from a different virus stock. (A) After immunostaining, the percentage of HCV NS5A positive cells was scored by fluorescence microscopy. (B) Supernatant HCV RNA titers were measured by Real-Time RT-PCR. (C, D) Average content of intracellular HCV Core and NS5A was determined by confocal microscopy based quantitative image analysis after immunostaining for the respective antigen. For each culture and antigen, 3 image stacks were acquired, each comprising an average of 110 cells. Average content of HCV antigen per cell was determined for each image using Imaris 6.1.0 software. Means of the 3 datasets are shown. AU, arbitrary units. None-infected negative control cells are not shown; for Core stainings, a background signal of 2.5 $Log_{10}$ AU (mean of 12 determinations) was recorded, whereas NS5A did not show a background signal.

FIG. 5

Treatment of Intergenotypic Viruses of Genotype 1, 2 and 6 with Putative Antivirals.

$4 \times 10^5$ Huh7.5 cells, derived on day 5 of the kinetic experiment (FIG. 4), were plated in 6 well dishes (−12 hrs). After 12 hrs, cell were treated at 0, 6, 12, 24, 48 and 72 hrs with 500 IU/mL interferon-α2b (A, B), 20 μM ribavirin (C, D) or 50 μM amantadine (E, F), respectively. At the indicated time points, percentage of HCV NS5A positive cells was determined using immunostaining and fluorescence microscopy (A, C, E); supernatant HCV RNA titers were measured by Real-Time RT-PCR (B, D, F).

FIG. 6

Importance of CD81 and SR-BI for Entry of Intergenotypic Viruses.

$6 \times 10^3$ Huh7.5 cells per well of a 96 well plate were treated for 1 hr with either anti-CD81 (A) or anti-SR-BI (B) at the indicated concentrations. ~150 FFU of the respective virus were added for 3 hrs. Virus stocks shown in Table 4 were used. After 48 hrs, the number of FFU was evaluated following immunostaining for HCV NS5A. % inhibition was calculated by relating the number of FFU/well to the mean number of FFU/well of 3 untreated wells. Means of triplicates and standard errors of the mean are shown. Control antibody preparations specified in Materials and Methods did not show any inhibitory effect at the equivalent concentrations. Stars, value <0. Data shown in B were generated in three different experiments (1st experiment: 1:10, 1:40 and 1:160 dilutions (1:160 not shown); 2nd experiment: 1:160 and 1:640 dilutions; 3rd experiment: all dilutions for J4/JFH1$_{F886L,Q1496L}$ viruses). The efficient blocking of infection of the different genotype recombinants with anti-SR-BI was confirmed in an independent experiment (data not shown). The apparent genotype specific differences seen at 1:160 dilution were only reproducible in 2 of 3 independent experiments.

FIG. 7

Average content of intracellular lipids during infection with genotype 1, 2 and 6 viruses.

At day 3, 5, 7, and 10 after infection (FIG. 4) with the indicated JFH1-based recombinants, $5 \times 10^4$ Huh7.5 cells of the respective cultures were plated on chamber slides. After 24 hrs, lipid droplets were stained with oil-red O, HCV antigen was stained with either anti-Core or anti-NS5A antibodies, and cell nuclei were stained with Hoechst reagent. For each culture, 6 image stacks were acquired, each of them comprised of on average 110 cells, using confocal microscopy imaging. Average content of lipids per cell was determined for each image using Imaris 6.1.0 software. Means and SEM of the 6 datasets are shown. AU, arbitrary units. Star, time points not analysed.

FIG. 8

Co-localization of HCV antigens with lipid droplets.

At day 5 after infection (FIG. 4) with the indicated JFH1-based recombinants, 5×10$^4$ Huh7.5 cells of the respective cultures were plated on chamber slides. After 24 hrs, lipid droplets were stained with oil-red O, HCV antigen was stained with either anti-Core or anti-NS5A antibodies, and cell nuclei were stained with Hoechst reagent. For each culture and antigen, 4 image stacks were acquired, each comprising >20 cells, using confocal microscopy imaging. Average % of co-localization was determined for each image stack using Imaris 6.1.0. Means and SEM of the 4 datasets are shown. Low % of co-localization of Core with lipids for the none-infected culture is due to a background signal observed in Core stainings (see also FIG. 4).

FIG. 9

Infectivity titers yielded by HK6a/JFH1 recombinants.

Infectivity titers were determined on cell free supernatants derived on day 3 and 6 from transfection cultures shown in FIG. 2A by the 50% tissue culture infectious dose method. These data are also partly shown in FIG. 3.

Tables

Direct sequence analysis was performed on viruses recovered from the first passage following the 1st transfection experiment with HK6a/JFH1 (FIG. 1B); on transfection and first viral passage viruses from the 2nd transfection experiment with HK6a/JFH1 (FIGS. 2A, and 2B); and on mutated HK6a/JFH1 after first passage (FIG. 2B). Capital letters indicate the presence of one determinate sequence peak. Two capital letters separated by a slash indicate the presence of a 50/50 quasispecies, whereas a capital letter separated by a slash from a lowercase letter indicates a quasispecies with a predominant vs a minor sequence. Criterion for listing of nt positions was the occurrence of a quasispecies in direct sequencing. Names of mutated HK6a/JFH1 recombinants engineered to contain mutations singly or in combination refer to the respective nt changes.

● nt/aa identical with pHK6a/JFH1 sequence. Numbers of nt/aa positions refer to pHK6a/JFH1. # nt/aa position in analogy to the H77 reference genome (accession number AF009606) determined as described by Kuiken et al. For aa positions the absolute (referring to H77 polyprotein) and relative (referring to the individual H77 protein) reference numbers are given. Grey shading indicates engineered nt and deduced aa changes. Data are partly shown in Table 1A.

TABLE 1A

Mutations of HK6a/JFH1 in Huh7.5 cells.

| Nucleotides | E1 | E1 | E2 | E2 | E2 | NS2 | NS2 | NS3 | NS5A | NS5A | NS5A | NS5A | NS5A | NS5A | NS5A |
|---|---|---|---|---|---|---|---|---|---|---|---|---|---|---|---|
| nucleotide position HK6a/JFH1 | 1389 | 1408 | 1499 | 1581 | 1590 | 2865 | 3319 | 4555 | 7074 | 7085 | 7134 | 7188 | 7368 | 7384 | 7434 |
| nucleotide position H77 (AF009606)# | 1387 | 1406 | 1500 | 1582 | 1591 | 2848 | 3302 | 4538 | 7056 | 7080 | 7129 | 7182 | 7363 | 7379 | 7420 |
| Sequence of pHK6a/JFH1 | | | | | | | | | | | | | | | |
| | T | A | A | T | A | A | T | G | A | G | A | T | C | A | C |
| Sequence of viruses recovered from infected Huh7.5 cells | | | | | | | | | | | | | | | |
| 1st Transfection Experiment | | | | | | | | | | | | | | | |
| HK6a/JFH1-1st passage (day 16) | C | ● | ● | ● | C | ● | ● | ● | ● | ● | ● | ● | C/t | G/a | C/t |
| 2nd Transfection Experiment | | | | | | | | | | | | | | | |
| HK6a/JFH1-Transfection (day 36) | C/T | ● | ● | C/T | ● | ● | C/T | ● | ● | G/a | ● | ● | C/t | ● | ● |
| HK6a/JFH1-1st passage (day 27) | C/T | G/A | G/A | C/T | ● | G/A | C/T | A/g | A/g | A/G | G/A | T/c | C/t | ● | C/t |
| Transfections with mutated HK6a/JFH1 | | | | | | | | | | | | | | | |
| HK6a/JFH1(T1389C)- 1st passage (day 12) | C | ● | ● | T/g | C/A | ● | ● | ● | ● | ● | ● | ● | C/t | ● | ● |
| HK6a/JFH1(A1590C)- 1st passage (day 12) | ● | ● | ● | ● | C | ● | ● | ● | ● | ● | ● | ● | C/t | ● | ● |
| HK6a/JFH1(T1389C, A1590C)- 1st passage (day 7) | C | ● | ● | ● | C | ● | ● | ● | ● | ● | ● | ● | C/t | ● | ● |

| Aminoacids | E1 | E1 | E2 | E2 | E2 | NS2 | NS2 | NS3 | NS5A | NS5A | NS5A | NS5A | NS5A | NS5A | NS5A |
|---|---|---|---|---|---|---|---|---|---|---|---|---|---|---|---|
| amino acid position HK6a/JFH1 | 350 | 356 | 387 | 414 | 417 | 842 | 993 | 1405 | 2245 | 2249 | 2265 | 2283 | 2343 | 2348 | 2365 |
| absolute amino acid position H77 (AF009606)# | 349 | 355 | 386 | 414 | 417 | 836 | 987 | 1399 | 2243 | 2247 | 2263 | 2281 | 2341 | 2346 | 2363 |
| relative amino acid position H77 (AF009606)# | 158 | 164 | 3 | 31 | 34 | 27 | 178 | 373 | 271 | 275 | 291 | 309 | 369 | 374 | 391 |
| Sequence of HK6a/JFH1 | | | | | | | | | | | | | | | |
| | F | I | T | I | N | K | G | K | Q | E | E | F | S | Q | S |
| Sequence of viruses recovered from infected Huh7.5 cells | | | | | | | | | | | | | | | |
| 1st Transfection Experiment | | | | | | | | | | | | | | | |
| HK6a/JFH1-1st passage (day 16) | S | ● | ● | ● | T | ● | ● | ● | ● | ● | ● | ● | S/I | ● | S/I |
| 2nd Transfection Experiment | | | | | | | | | | | | | | | |
| HK6a/JFH1-Transfection (day 36) | S/F | ● | ● | T/I | ● | ● | ● | ● | ● | E/k | ● | ● | S/I | ● | ● |
| HK6a/JFH1-1st passage (day 27) | S/F | M/I | A/T | T/I | ● | R/K | ● | ● | Q/r | K/E | G/E | F/s | S/I | ● | S/I |
| Transfections with mutated HK6a/JFH1 | | | | | | | | | | | | | | | |
| HK6a/JFH1(T1389C)- 1st passage (day 12) | S | ● | ● | I/s | T/N | ● | ● | ● | ● | ● | ● | ● | S/I | ● | ● |
| HK6a/JFH1(A1590C)- 1st passage (day 12) | ● | ● | ● | ● | T | ● | ● | ● | ● | ● | ● | ● | S/I | ● | ● |
| HK6a/JFH1(T1389C, A1590C)- 1st passage (day 7) | S | ● | ● | ● | T | ● | ● | ● | ● | ● | ● | ● | S/I | ● | ● |

TABLE 1B

Coding nucleotide changes of original and adapted HK6a/JFH1 recombinants in Huh7.5 cells.

| HCV gene | | E1 | E2 | E2 | E2 | NS5A |
|---|---|---|---|---|---|---|
| Nucleotide position † | | | | | | |
| HK6a/JFH1 | | 1389 | 1581 | 1586 | 1590 | 7085 |
| H77 abs ref | | 1387 | 1582 | 1587 | 1591 | 7080 |
| pHK6a/JFH1 | | T | T | A | A | G |
| Original construct | Passage (day) | | | | | |
| HK6a/JFH1, exp.1 * | 1st (16) | C | • | • | C | • |
| HK6a/JFH1, exp. 2 | transf. (36) | T/C | T/C | A/g | • | G/a |
| Mutated constructs | | | | | | |
| HK6a/JFH1$_{F350S}$, exp.1# | 1st (12) | C | T/g | • | A/C | • |
| HK6a/JFH1$_{N417T}$, exp.1 | 1st (12) | C | • | • | C | • |
| HK6a/JFH1$_{F350S,N417T}$, exp.1** | 1st (7) | C | • | • | C | • |
| HK6a/JFH1$_{F350S,N417T}$, exp.1** | 1st (10) | C | • | • | C | • |
| HK6a/JFH1$_{F350S}$, exp.2 | 1st (17) | C | T/c | A/G | A/c | • |
| HK6a/JFH1$_{N417T}$, exp.2 | 1st (20) | C | • | • | C | • |
| HK6a/JFH1$_{F350S,N417T}$, exp.2 | 1st (5) | C | • | • | C | • |
| Amino acid position † | | | | | | |
| HK6a/JFH1 | | 350 | 414 | 416 | 417 | 2249 |
| H77 abs ref | | 349 | 414 | 416 | 417 | 2247 |
| Change | | F→S | ‡ | T→A | N→T | E→K |

†Positions are numbered according to the HCV sequence of pHK6a/JFH1.
Corresponding H77 (AF009606) absolute reference positions are given. Coding mutations are shown.
Dots indicate identity with the original plasmid sequence.
Positions with mixtures are written with the dominant sequence in capital and the minor sequence in lower case letters (a 50/50 quasispecies is shown as two capital letters).

Highlighted positions are mutations engineered into HK6a/JFH1.

In addition, the following non-coding mutations were found: HK6a/JFH1 (exp. 1) 1st (16) A7384G/a; HK6a/JFH1 (exp. 2) transf. (36) T3319T/C.

*Clonal sequence analysis of nt 1243-1619 within the envelope genes showed that E1 F350S and E2 N417T amino acid changes were combined in 4/4 clones #HK6a/JFH1F350S used in this experiment had a deletion of nucleotides 9510-9530 in the 3'UTR (poly U-tract). Clonal sequence analysis of nt 1243-1619 showed that 3/6 genomes encoded the amino acid change at position 417 (N417T), while 2 other genomes encoded changes at position 414 (I414S or I414T); the last cloned genome had another mutation, encoding an amino acid change at position 413, not observed in direct sequencing (L413V).

**Data are derived from 2 different 1st passages of the same transfection experiments. HK6a/JFH1F350S,N417T (exp. 1) 1st (10) is the virus stock shown in Table 4.

‡Amino acid change I_T/S encoded by nucleotide change T_C/G.

Data are partly shown in Table 1A. In Table 1A and 1B the following names are used interchangeably:
HK6a/JFH1(T1389C, A1590C) and HK6a/JFH1(F350S, N417T)
HK6a/JFH1(T1389C) and HK6a/JFH1(F350S)
HK6a/JFH1(A1590C) and HK6a/JFH1(N417T)

TABLE 2

Cross-genotype neutralization potential of chronic phase genotype 1a, 4a and 5a serum against genotype 1-7 recombinant viruses.

| Core-NS2 | Reciprocal 50% serum neutralizing antibody titer | | |
|---|---|---|---|
| Genotype | 1a (H06) | 4a (AA) | 5a (SA3) |
| 1a | 1600 | <100* | <100 |
| 1b | 800 | <100* | <100* |
| 2a | <100* | <100** | <100 |
| 2b | 3200 | 400 | 200 |
| 3a | <100* | <100** | <100 |
| 4a | 12800 | 6400 | 200 |
| 5a | 25600 | 3200 | 6400 |
| 6a | 204800 | 25600 | 12800 |
| 7a | 25600 | 3200 | 1600 |

Neutralization of genotype 1a, 2a, 3a, 4a, 5a and 6a viruses with 1a (H06), 4a (AA) and 5a (SA3) chronic phase serum was described previously. Similarly, approximately 150 FFU of J4/JFH1$_{F886L,Q1496L}$, 80 or 150 FFU of J8/JFH1, and 30 FFU of QC69/JFH1 stock viruses were pre-incubated with 2-fold dilutions of sera in triplicates, before infection of 6×10$^3$ Huh7.5 cells for 3 hrs. After 48 hrs incubation, the number of FFUs was determined for each culture by anti-NS5A immunostaining. 50% neutralization titers indicate the serum dilution, which led to an at least 50% reduction of FFU compared to the mean of 6 non-serum treated cultures. *50% neutralization observed at 1:50 serum dilution; **less than 50% neutralization observed at 1:50 serum dilution.

TABLE 3

Primers used for HK6a/JFH1 long RT-PCR procedure to generate amplicons for direct sequencing of the ORF

| Amplification step and amplicon | Primer name | SEQ ID NO: | Primer sequence |
|---|---|---|---|
| cDNA synthesis | 9470R(24)_JFH1 | 7 | 5'-CTATGGAGTGTACCTAGTGTGTGC-3' |
| 1st round PCR | -285S_HCV-MOD | 8 | 5'-ACTGTCTTCACGCAGAAAGCGCCTAGCCAT-3' |
| | 9470R(24)_JFH1 | 7 | 5'-CTATGGAGTGTACCTAGTGTGTGC-3' |
| 2nd round PCR | | | |
| Amplicon 1 | -84S_HCV-MOD | 9 | 5'-GTAGCGTTGGGTTGCGAAAGGCCTTGTGGTACTGCCTGAT-3' |
| | 6aR1082 | 10 | 5'-CCTACGGAATCCCGTTGCAGGTGTG-3' |
| Amplicon 2 | 6aF569 | 11 | 5'-TGTGGGTGGGCAGGTTGGCTCCTGTC-3' |
| | 6aRMut1850 | 12 | 5'-GTGGTTCCTACTACGACAGGGCTGGGCGTGAAGCAG-3' |
| Amplicon 3 | 6aF1572 | 13 | 5'-CTTTGAACTGCAATGATTCCCTC-3' |
| | 6aR2680 | 14 | 5'-CATGTAGGTACACGCAGGCACAA-3' |
| Amplicon 4 | 6aF2293 | 15 | 5'-CTGGACCAGAGGCGAGCGGTGTG-3' |
| | R6a3404FusJFH1 | 16 | 5'-AGTGATGGGAGCCAAAAGCTTCCAACCCCCGC-3' |
| Amplicon 5 | 6aF3102 | 17 | 5'-GGGGTAAGTACGTGCAGGCGTG-3' |
| | 4118R_JFH1 | 18 | 5'-CGCCCGAGGCCTACCTCTTCTATATC-3' |
| Amplicon 6 | 3880S_J6 | 19 | 5'-CCCATCACGTACTCCACATATGGC-3' |
| | 4796R_JFH1 | 20 | 5'-GCGCACACCGTAGCTTGGTAGG-3' |
| Amplicon 7 | 4528S_J6 | 21 | 5'-GAGCGAGCCTCAGGAATGTTTGACA-3' |
| | 5446R_JFH1 | 22 | 5'-TGATGTTGAGAAGGATGGTGGTAC-3' |
| Amplicon 8 | 5272S_JFH1 | 23 | 5'-TGGCCCAAAGTGGAACAATTTTGG-3' |
| | 6460R_J6 | 24 | 5'-CAACGCAGAACGAGACCTCATCCC-3' |
| Amplicon 9 | 6186S_JFH1 | 25 | 5'-GACCTTTCCTATCAATTGCTACAC-3' |
| | 7234R_JFH1 | 26 | 5'-GAAGCTCTACCTGATCAGACTCCA-3' |
| Amplicon 10 | 6862S_JFH1 | 27 | 5'-TGGGCACGGCCTGACTACAA-3' |
| | 7848R_JFH1 | 28 | 5'-GGCCATTTTCTCGCAGACCCGGAC-3' |
| Amplicon 11 | 7741S_J6 | 29 | 5'-ATGGCCAAAAATGAGGTGTTCTGC-3' |
| | 8703R_JFH1 | 30 | 5'-AAGGTCCAAAGGATTCACGGAGTA-3' |
| Amplicon 12 | 8137S_JFH1 | 31 | 5'-GGTCAAACCTGCGGTTACAGACGTTG-3' |
| | 9464R(24)_JFH1 | 32 | 5'-GTGTACCTAGTGTGTGCCGCTCTA-3' |

TABLE 4

Titrated Stocks of JFH1-based Intergenotypic Recombinants of HCV Genotype 1, 2 and 6.

| Core-NS2 Genotype | Virus † | Viral Passage | HCV Infectivity titer * | | HCV RNA titer # | Specific infectivity ** |
|---|---|---|---|---|---|---|
| | | | $LOG_{10}$ $TCID_{50}$/mL | $LOG_{10}$ FFU/mL | $LOG_{10}$ IU/mL | $TCID_{50}$/IU |
| 1a | H77C/JFH1$_{V787A, Q1247L}$ | 2nd | 4.3 ± 0.0 | 4.3 ± 0.2 | 7.5 ± 0.1 | 1/1585 |
| 1b | J4/JFH1$_{F886L, Q1496L}$ | 1st | 3.7 ± 0.3 | 3.2 ± 0.1 | 7.3 ± 0.1 | 1/3981 |
| 2a | J6/JFH1 | 2nd | 5.2 ± 0.1 | 5.0 ± 0.2 | 7.6 ± 0.0 | 1/251 |
| 2b | J8/JFH1 | 1st | 4.4 ± 0.1 | 4.1 ± 0.1 | 7.4 ± 0.0 | 1/1000 |
| 6a | HK6a/JFH1$_{F350S, N417T}$ | 1st | 4.4 ± 0.2 | 4.0 ± 0.0 | 7.0 ± 0.0 | 1/398 |

† HCV recombinant with engineered adaptive mutations given as subscript. HCV ORF sequences, including the presence of specific mutations, were verified by direct sequencing of stock genomes; additionally, a 50/50 quasispecies coding mutation was revealed for H77C/JFH1 (Y361Y/H).
* Measured as $TCID_{50}$/mL (mean of four determinations, each based on serial dilution with 6 replicates per dilution; ±SEM, standard error of the mean) and FFU/mL (mean of two determinations, each based on serial dilution with 6 replicates per dilution; ±SEM).
Measured as IU/mL (mean of two determinations, ±SEM) in a Real-Time RT-PCR assay.
** Determined as HCV RNA titer (IU/mL) related to HCV infectivity titer ($TCID_{50}$/mL).

TABLE 5

Characterization of genotype 1, 2 and 6 kinetic cultures at peak of infection.

| Core-NS2 Genotype | Virus † | Day * | Infection # % | HCV RNA titer ** | | HCV Infectivity titer & | | Specific infectivity | | HCV Antigen $ | | Lipid $ |
|---|---|---|---|---|---|---|---|---|---|---|---|---|
| | | | | EC ‡ $LOG_{10}$ IU/mL | IC ## $LOG_{10}$ IU/$10^5$ cells | EC ‡ $LOG_{10}$ FFU/mL | IC ## $LOG_{10}$ FFU/$10^5$ cells | EC ‡ FFU/IU | IC ## FFU/IU | Core/cell $LOG_{10}$ AU | NS5A/cell $LOG_{10}$ | Lipid/cell $LOG_{10}$ |
| 1a | H77C/JFH1$_{V787A, Q1247L}$ | 7 | 80 | 7.4 | 7.2 | 4.0 | 2.7 | 1/2512 | 1/31623 | 4.9 | 5.5 | 4.3 |
| 1b | J4/JFH1$_{F886L, Q1496L}$ | 7 | 80 | 7.4 | 6.6 | 4.0 | 1.9 | 1/2512 | 1/50119 | 4.9 | 5.5 | 4.4 |
| 2a | J6/JFH1 | 7 | 90 | 8.0 | 7.2 | 5.1 | 2.5 | 1/794 | 1/50119 | 5.5 | 5.7 | 4.0 |
| 2b | J8/JFH1 | 7 | 90 | 7.4 | 7.3 | 4.6 | 2.7 | 1/631 | 1/39811 | 5.2 | 5.5 | 4.3 |
| 6a | HK6a/JFH1$_{F350S, N417T}$ | 7 | 80 | 7.0 | 7.0 | 4.1 | 1.9 | 1/794 | 1/125893 | 5.4 | 5.4 | 4.2 |
| None | None | 7 | 0 | nd | nd | nd | nd | na | na | 3.0 | nd | 4.0 |

† HCV recombinant with engineered adaptive mutations used in comparative kinetic study (FIG. 4).
* The first time point (day), at which HCV RNA titers in culture supernatant were ≥$10^7$ IU/mL (FIG. 4B).
% infected cells scored using fluorescence microscopy (FIG. 4A).
** IU/mL or IU/$10^5$ cells.
‡ EC, extracellular analysis was carried out on culture supernatants.
IC, for intracellular analysis pellets of $10^5$ cells were resuspended in growth medium and subjected to 4 freeze/thaw cycles. After centrifugation, supernatants were analysed. & FFU/mL or FFU/$10^5$ cells (mean of three determinations, each based on serial dilution with 1 replicate per dilution).

REFERENCES

Billaud, J. N., Selway, D., Yu, N., and Phillips, T. R. (2000). Replication rate of feline immunodeficiency virus in astrocytes is envelope dependent: implications for glutamate uptake. *Virology* 266, 180-188.

Gottwein, J. M. et al. (2007) Robust Hepatitis C Genotype 3a Cell Culture Releasing Adapted Intergenotypic 3a/2a (S52/JFH1) Viruses Gastroenterology 133, 1614-1626.

Hui, C. K., Yuen, M. F., Sablon, E., Chan, A. O., Wong, B. C., and Lai, C. L. (2003). Interferon and ribavirin therapy for chronic hepatitis C virus genotype 6: a comparison with genotype 1. *J. Infect. Dis.* 187, 1071-1074.

Kuiken C, Combet C, Bukh J, Shin I, Deleage G, Mizokami M, Richardson R, Sablon E, Yusim K, Pawlotsky J M, Simmonds P. A comprehensive system for consistent numbering of HCV sequences, proteins and epitopes. Hepatology 2006; 44:1355-1361.

Lindenbach, B. D., Evans, M. J., Syder, A. J., Wolk, B., Tellinghuisen, T. L., Liu, C. C., Maruyama, T., Hynes, R. O., Burton, D. R., McKeating, J. A., and Rice, C. M. (2005). Complete replication of hepatitis C virus in cell culture. Science. 309, 623-626.

Meunier, J. C. et al. (2005) Evidence for Cross-Genotype Neutralization of Hepatitis C Virus Pseudo-Particles and Enhancement of Infectivity by Apolipoprotein C1 *Proc Natl Acad Sci USA* 102, 4560-4565.

Simmonds P, Bukh J, Combet C, Deleage G, Enomoto N, Feinstone S, et al. Consensus proposals for a unified system of nomenclature of hepatitis C virus genotypes. Hepatology 2005; 42(4):962-973.

The invention claimed is:

1. A nucleic acid molecule comprising a nucleic acid which encodes a recombinant human hepatitis C virus of genotype 6a/JFH1 that is capable of expressing said virus when transfected into cells, wherein said molecule encodes an amino acid sequence with a sequence identity of at least 95% to that of SEQ ID NO: 2, wherein said molecule encodes an adaptive mutation F350S in the E1 protein and a T416A or N417T adaptive mutation in the E2 protein of SEQ ID NO: 2, and wherein said adaptive mutations provide an improved ability to generate infectious viral particles in cell culture compared to an HCV genotype 6a/JFH1 virus without said adaptive mutations.

2. The nucleic acid molecule according to claim 1, wherein said nucleic acid molecule is further capable of infectivity in vivo.

3. The nucleic acid molecule according to claim 1, wherein said molecule comprises the nucleic acid sequence with a sequence identity of at least 95% to that of SEQ ID NO:1.

4. The nucleic acid molecule according to claim 1, wherein the nucleic acid molecule comprises T1389C and A1590C adaptive mutations in SEQ ID NO:1.

5. The nucleic acid molecule according to claim 1, wherein said molecule encodes adaptive mutations F350S in the E1 gene and T416A in the E2 gene of SEQ ID NO:2.

6. A nucleic acid molecule comprising a nucleic acid which encodes a recombinant human hepatitis C virus of genotype 6a/JFH1 that is capable of expressing said virus when transfected into cells, wherein said molecule encodes the amino acid sequence with a sequence identity of at least 95% to that of SEQ ID NO: 2, wherein said molecule comprises a T1389C adaptive mutation in the E1 gene and a T1581C, T1581G, or A1586G adaptive mutation in the E2 gene of SEQ ID NO:1, and wherein said adaptive mutations provide an improved ability to generate infectious viral particles in cell culture compared to an HCV genotype 6a/JFH1 virus without said adaptive mutations.

7. The nucleic acid molecule according to claim 1, wherein said molecule encodes adaptive mutations an F350S in the E1 protein and a N417T in the E2 protein of SEQ ID NO:2.

8. The nucleic acid molecule according to claim 7, wherein said molecule is capable of generating a HCV RNA titer of $10^4$ IU/ml or above following transfection and/or subsequent viral passage.

9. The nucleic acid molecule according to claim 7, wherein said molecule is capable of generating a HCV infectivity titer of $10^2$ TCID$_{50}$/ml (50% tissue culture infectious doses)/ml or above following transfection and/or subsequent viral passage.

10. A method for producing a hepatitis C virus particle, comprising:
(a) culturing a cell comprising a nucleic acid molecule which encodes human hepatitis C virus of genotype 6a/JFH1 that is capable of expressing said virus when transfected into cells and wherein said nucleic acid molecule encodes an amino acid sequence with a sequence identity of at least 95% to that of SEQ ID NO:2, wherein said molecule encodes adaptive mutations F350S in the E1 protein and T416A or N417T in the E2 protein of SEQ ID NO:2, said adaptive mutations providing an improved ability to generate infectious viral particles in cell culture compared to an HCV genotype 6a/JFH1 virus without said adaptive mutations; and,
(b) allowing the cell to produce the virus.

11. A hepatitis C virus particle comprising a nucleic acid molecule which encodes human hepatitis C virus of genotype 6a/JFH1 that is capable of expressing said virus when transfected into cells and wherein said nucleic acid molecule encodes the amino acid sequence with a sequence identity of at least 95% to that of SEQ ID NO:2, wherein said molecule encodes adaptive mutations F350S in the E1 protein and a T416A or a N417T in the E2 protein of SEQ ID NO:2, and wherein said adaptive mutation provides an improved ability to generate infectious viral particles in cell culture compared to an HCV genotype 6a/JFH1 virus without said adaptive mutations.

12. The hepatitis C virus particle according to claim 11, wherein said hepatitis C virus particle is further capable of infectivity in vivo.

13. The hepatitis C virus particle according to claim 11, wherein said hepatitis C virus particle comprises the nucleic acid sequence with a sequence identity of at least 95% to that of SEQ ID NO 1.

14. The hepatitis C virus particle according to claim 11, wherein the nucleic acid molecule comprises a T1389C and an A1590C adaptive mutation in SEQ ID NO 1.

15. The hepatitis C virus particle according to claim 11, wherein the nucleic acid molecule encodes-adaptive mutations an F350S in the E1 protein and T416A in the E2 protein of SEQ ID NO:2.

16. A hepatitis C virus particle, comprising a nucleic acid which encodes a recombinant human hepatitis C virus of genotype 6a/JFH1 that is capable of expressing said virus when transfected into cells and wherein said nucleic acid encodes the amino acid sequence with a sequence identity of at least 95% to that of SEQ ID NO 2, wherein said molecule comprises a T1389C adaptive mutation in the E1 gene and a T1581C, T1581G, or A1586G adaptive mutation in the E2 gene of SEQ ID NO:1, and wherein said adaptive mutations provide an improved ability to generate infectious viral particles in cell culture compared to an HCV genotype 6a/JFH1 virus without said adaptive mutations.

17. The hepatitis C virus particle according to claim 15, wherein said nucleic acid molecule is capable of generating a HCV RNA titer of $10^4$ IU/ml or above following transfection and/or subsequent viral passage.

18. The hepatitis C virus particle according to claim 15, wherein said nucleic acid molecule is capable of generating a HCV infectivity titer of $10^2$ TCID$_{50}$/ml (50% tissue culture infectious doses)/ml or above following transfection and/or subsequent viral passage.

* * * * *

SEQUENCE LISTING

<160> NUMBER OF SEQ ID NOS: 32

<210> SEQ ID NO 1
<211> LENGTH: 9684
<212> TYPE: DNA
<213> ORGANISM: Hepatitis C virus

<400> SEQUENCE: 1

```
acctgcccct aatagggcg acactccgcc atgaatcact ccctgtgag gaactactgt      60 cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgcccggga ggtctcgtag accgtgcacc atgagcacac ttccaaaacc     360
ccaaagaaaa accaaaagaa acaccaaccg tcgcccaatg gacgtcaagt tcccgggtgg     420
cggtcagatc gttggcggag tttacttgtt gccgcgcagg ggcccccggt tgggtgtgcg     480
cgcgacgagg aagacttccg agcgatccca gcccagaggc aggcgccaac ctataccaaa     540
ggcgcgccag ccccagggca ggcactgggc tcagcccgga tatccttggc ccctttatgg     600
```

```
gaacgagggc tgtgggtggg caggttggct cctgtccccc cgcggctccc ggccacactg    660
gggccccaac gaccccggc gtcgatcccg gaatttgggt aaggtcatcg ataccctaac     720
gtgtgggttc gccgatctca tggggtacat tcccgtcgtg ggcgcgcctt tgggcggcgt    780
cgcggctgca ctcgcacatg gtgtgagggc aatcgaggac gggatcaatt atgcaacagg    840
gaatcttccc ggttgctctt tctctatctt cctcttggca ctactctcgt gcctcacaac    900
gccagcgtcg gctcttacct acggtaactc cagtgggcta taccatctta caaatgattg    960
ccccaactcc agcatcgtgc tggaggcgga tgccatgatc ttgcatttgc ctggatgctt   1020
gccttgtgtg agggtcaata caaccagtc catctgttgg catgctgtgt cccccaccct    1080
agccatacca aatgcttcca cacctgcaac gggattccgt aggcatgtgg accttcttgc   1140
gggcgccgca gtggtttgct catccctgta catcggggat ctgtgcggct ccctcttttt   1200
ggcagggcaa ctatttacct ttcagccccg ccgtcactgg actgtgcaag actgcaactg   1260
ctccatttat acaggccacg tcaccggcca caggatggct gggacatga tgatgaattg     1320 gtcacccaca accactctgg tcctatctag tatcttgagg gtacctgaga tctgtgcgag   1380
tgtgatattt ggtggccatt gggggatact actagccgtt gcctactttg gtatggctgg   1440
caactggcta aaagttctgg ctgtcctgtt cttatttgca ggggttgaag caaccaccac   1500
catcggccat caagtaggcc gcactactgg tggcttagcc agtctcttct ccatcggtcc   1560
caggcaaaat ctacaactca tcaacaccaa tggcagctgg catataaaca ggactgctct   1620
gaactgcaat gattccctcc agacggggtt cataacgtca ctcttttatg ccaagaacgt   1680
caactcctcg ggctgcccag agcggatggc tgcgtgtaag cccctcgcgg acttccggca   1740
ggggtggggc caaataacct acaaagtcaa catctcgggc ccctccgacg accgtcccta   1800
ctgttggcat tacgctccca ggccatgtga cgtggtgtcg gcccgcacgg tgtgcggccc   1860
cgtttactgc ttcacgccca gccctgtcgt agtaggaacc actgacaagc tgggcattcc   1920
cacatacaac tggggggaga atgagacgga tgtgttcatg ttggaaagcc ttcggcctcc   1980
tactggagga tggtttgggt gcacgtggat gaactctacg ggctttacca agacctgtgg   2040
tgccccgcca tgtcagatag tcccgggaga ttacaatagc tctgccaatg agcttttgtg   2100
ccccaccgac tgcttccgta acatccgga agctacatat cagcggtgtg gatcgggacc    2160
ctggatcaca cctaggtgtc tggtggatta ccctacagg ctgtggcact accctgtac     2220 tgtcaacttc accttgcata aagtcaggat gttcgtggga ggcattgagc atcggtttga   2280
cgccgcatgt aactggacca gaggcgagcg gtgtgatcta catgacagag acaggattga   2340
aatgagcccg ctgctttcct caactacgca gcttgccata cttccctgtt cattttccac   2400
catgccggcc ttgtcaaccg gcctcatcca cctgcatcag aacatagtgg acgtgcagta   2460
cctctacgga gtctcctcga gcgttacctc gtgggtggtg aagtgggagt acattgttct   2520
ggtgttcctg gttctggcag atgctcggat ttgtacatgt ctctggttaa tgctgctcat   2580
aaccaacgtt gaagcagcag tggaaaggct tgtcgtcctc aatgcggcta gcgccgccgg   2640
caccgccggc tggtggtggg cggtgctctt cctgtgctgt gcttggtacg tgaaaggccg   2700
ccttgtgcct gcgtgtacct acatggcact gggaatgtgg ccgttgctcc tgacaatctt   2760
ggccctgcct cgccgagcat acgctatgga caatgagcaa gcggcatccc tcggagctgt   2820
tggtctcttg gtgctcacca tctttaccat cacccccatg tacaagaagc tgttgacctg   2880 ctccattttgg tggaatcagt atttcctcgc ccgagctgag gccatgatac acgagtgggt   2940
gcccgaccta cgggttaggg gcggtaggga ctccatcatc ttacttacct gcttgttaca   3000
```

```
tccacagctg gggtttgagg tcaccaaaat tctactagcc atcctggccc ctctatacat    3060
cctgcagtac agtttgctca aggtgcctta ctttgtgcgc gcccacgtac tcctgcgtgc    3120
ttgcctgctt gttcgtaggc tagcaggggg taagtacgtg caggcgtgcc ttctgaggtt    3180
gggcgcttgg actggcacct tgtctatga ccatctcgcc cctctctctg actgggctag    3240
cgacggactg cgcgatttgg cagtcgcaat cgagccggtc attttctctc ccatggagaa    3300
gaaaatcatt acctggggtg cggataccgc cgcgtgtggt gacatcttga gtggcctccc    3360
ggtgtcagcg aggttgggga atttggtgct actgggaccc gcggacgata tgcagcgcgg    3420
gggttggaag cttttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gaggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840
gaaggggtcc tcggggggc cggtgctctg ccctagggc cacgtcgttg ggctcttccg    3900
agcagctgtg tgctctcggg gcgtggccaa atccatcgat ttcatccccg ttgagacact    3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aacccctcgg tagctgccac    4140
cctggggttt ggggcgtacc tatccaaggc acatggcatc aatcccaaca ttaggactgg    4200
agtcaggacc gtgatgaccg gggaggccat cacgtactcc acatatggca aatttctcgc    4260 cgatggggc tgcgctagcg gcgcctatga catcatcata tgcgatgaat gccacgctgt    4320
ggatgctacc tccattctcg gcatcggaac ggtccttgat caagcagaga cagccgggt    4380 cagactaact gtgctggcta cggccacacc ccccgggtca gtgacaaccc cccatcccga    4440
tatagaagag gtaggcctcg gcgggaggg tgagatcccc ttctatggga gggcgattcc    4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggaa    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
```

```
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtgaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accacccgcg ggggccaccg gctttgtcgt cagtggcctg gtggggctg ccgtgggcag    5880 cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggagggg cgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctccct tcatctcttg tcaaaggggg tacaagggtg tgtgggccgg    6420
cactggcatc atgaccacgc gctgcccttg cggcgccaac atctctggca atgtccgcct    6480
gggctctatg aggatcacag gcctaaaac ctgcatgaac acctggcagg ggaccttttcc    6540 tatcaattgc tacacggagg ccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggttttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctccccagg agcgggttttc cacgggcctt    7200 accggcttgg gcacggcctg actacaaccc gccgctcgtg gaatcgtgga ggaggccaga    7260
ttaccaaccg cccaccgttg ctggttgtgc tctccccccc cccaagaagg ccccgacgcc    7320 tccccccaagg agacgccgga cagtgggtct gagcgagagc accatatcag aagccctcca    7380
gcaactggcc atcaagacct ttggccagcc cccctcgagc ggtgatgcag gctcgtccac    7440
gggggcgggc gccgccgaat ccggcggtcc gacgtcccct ggtgagccgg cccccctcaga    7500 gacaggttcc gcctcctcta tgccccccct cgaggggggag cctggagatc cggacctgga    7560
gtctgatcag gtagagcttc aacctccccc ccaggggggggg ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740 caacccctttg agtaactcgc tgttgcgata ccataacaag gtgtactgta acatcaaa    7800
```

```
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca agtatggatt    7980
cggggccaag gaggtccgca gcttgtccgg gagggccgtt aaccacatca gtccgtgtg     8040 gaaggacctc ctggaagacc acaaacacc  aattcccaca accatcatgg ccaaaaatga    8100
ggtgttctgc gtggaccccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
agggcccatg ttcaacagca agggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc cccagaccg  gaatatgacc tggagctaat    8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct ctccattct  catggtccaa gacaccctgg accagaacct    9000
caactttgag atgtatggat cagtatactc cgtgaatcct ttggacctt c cagccataat    9060 tgagaggtta cacgggcttg acgccttttc tatgcacaca tactctcacc acgaactgac    9120
gcgggtggct tcagccctca gaaaacttgg gcgccaccc  ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca tttttcacag    9360
cgtgtcgcgc gcccgacccc gctcattact cttcggccta ctcctacttt tcgtaggggt    9420
aggcctcttc ctactcccg  ctcggtagag cggcacacac taggtacact ccatagctaa    9480
ctgttccttt ttttttttt  tttttttt    ttttttttt  tttttttt   cttttttttt    9540 ttttcccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                           9684
```

<210> SEQ ID NO 2
<211> LENGTH: 3035
<212> TYPE: PRT
<213> ORGANISM: Hepatitis C virus

<400> SEQUENCE: 2

Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala

```
                35                  40                  45
Thr Arg Lys Thr Ser Glu Arg Ser Gln Pro Arg Gly Arg Arg Gln Pro
 50                  55                  60
Ile Pro Lys Ala Arg Gln Pro Gln Gly Arg His Trp Ala Gln Pro Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro His Trp Gly Pro Asn Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Val Val Gly Ala Pro Leu
130                 135                 140
Gly Gly Val Ala Ala Leu Ala His Gly Val Arg Ala Ile Glu Asp
145                 150                 155                 160
Gly Ile Asn Tyr Ala Thr Gly Asn Leu Pro Gly Cys Ser Phe Ser Ile
                165                 170                 175
Phe Leu Leu Ala Leu Leu Ser Cys Leu Thr Thr Pro Ala Ser Ala Leu
                180                 185                 190
Thr Tyr Gly Asn Ser Ser Gly Leu Tyr His Leu Thr Asn Asp Cys Pro
                195                 200                 205
Asn Ser Ser Ile Val Leu Glu Ala Asp Ala Met Ile Leu His Leu Pro
210                 215                 220
Gly Cys Leu Pro Cys Val Arg Val Asn Asn Gln Ser Ile Cys Trp
225                 230                 235                 240
His Ala Val Ser Pro Thr Leu Ala Ile Pro Asn Ala Ser Thr Pro Ala
                245                 250                 255
Thr Gly Phe Arg Arg His Val Asp Leu Leu Ala Gly Ala Ala Val Val
                260                 265                 270
Cys Ser Ser Leu Tyr Ile Gly Asp Leu Cys Gly Ser Leu Phe Leu Ala
                275                 280                 285
Gly Gln Leu Phe Thr Phe Gln Pro Arg Arg His Trp Thr Val Gln Asp
290                 295                 300
Cys Asn Cys Ser Ile Tyr Thr Gly His Val Thr Gly His Arg Met Ala
305                 310                 315                 320
Trp Asp Met Met Met Asn Trp Ser Pro Thr Thr Thr Leu Val Leu Ser
                325                 330                 335
Ser Ile Leu Arg Val Pro Glu Ile Cys Ala Ser Val Ile Phe Gly Gly
                340                 345                 350
His Trp Gly Ile Leu Leu Ala Val Ala Tyr Phe Gly Met Ala Gly Asn
                355                 360                 365
Trp Leu Lys Val Leu Ala Val Leu Phe Leu Phe Ala Gly Val Glu Ala
                370                 375                 380
Thr Thr Thr Ile Gly His Gln Val Gly Arg Thr Thr Gly Gly Leu Ala
385                 390                 395                 400
Ser Leu Phe Ser Ile Gly Pro Arg Gln Asn Leu Gln Leu Ile Asn Thr
                405                 410                 415
Asn Gly Ser Trp His Ile Asn Arg Thr Ala Leu Asn Cys Asn Asp Ser
                420                 425                 430
Leu Gln Thr Gly Phe Ile Thr Ser Leu Phe Tyr Ala Lys Asn Val Asn
                435                 440                 445
Ser Ser Gly Cys Pro Glu Arg Met Ala Ala Cys Lys Pro Leu Ala Asp
450                 455                 460
```

-continued

```
Phe Arg Gln Gly Trp Gly Gln Ile Thr Tyr Lys Val Asn Ile Ser Gly
465                 470                 475                 480

Pro Ser Asp Asp Arg Pro Tyr Cys Trp His Tyr Ala Pro Arg Pro Cys
            485                 490                 495

Asp Val Val Ser Ala Arg Thr Val Cys Gly Pro Val Tyr Cys Phe Thr
        500                 505                 510

Pro Ser Pro Val Val Gly Thr Thr Asp Lys Leu Gly Ile Pro Thr
    515                 520                 525

Tyr Asn Trp Gly Glu Asn Glu Thr Asp Val Phe Met Leu Glu Ser Leu
530                 535                 540

Arg Pro Pro Thr Gly Gly Trp Phe Gly Cys Thr Trp Met Asn Ser Thr
545                 550                 555                 560

Gly Phe Thr Lys Thr Cys Gly Ala Pro Pro Cys Gln Ile Val Pro Gly
                565                 570                 575

Asp Tyr Asn Ser Ser Ala Asn Glu Leu Leu Cys Pro Thr Asp Cys Phe
            580                 585                 590

Arg Lys His Pro Glu Ala Thr Tyr Gln Arg Cys Gly Ser Gly Pro Trp
            595                 600                 605

Ile Thr Pro Arg Cys Leu Val Asp Tyr Pro Tyr Arg Leu Trp His Tyr
610                 615                 620

Pro Cys Thr Val Asn Phe Thr Leu His Lys Val Arg Met Phe Val Gly
625                 630                 635                 640

Gly Ile Glu His Arg Phe Asp Ala Ala Cys Asn Trp Thr Arg Gly Glu
                645                 650                 655

Arg Cys Asp Leu His Asp Arg Asp Arg Ile Glu Met Ser Pro Leu Leu
            660                 665                 670

Phe Ser Thr Thr Gln Leu Ala Ile Leu Pro Cys Ser Phe Ser Thr Met
            675                 680                 685

Pro Ala Leu Ser Thr Gly Leu Ile His Leu His Gln Asn Ile Val Asp
    690                 695                 700

Val Gln Tyr Leu Tyr Gly Val Ser Ser Ser Val Thr Ser Trp Val Val
705                 710                 715                 720

Lys Trp Glu Tyr Ile Val Leu Val Phe Leu Val Leu Ala Asp Ala Arg
                725                 730                 735

Ile Cys Thr Cys Leu Trp Leu Met Leu Leu Ile Thr Asn Val Glu Ala
            740                 745                 750

Ala Val Glu Arg Leu Val Val Leu Asn Ala Ala Ser Ala Ala Gly Thr
            755                 760                 765

Ala Gly Trp Trp Trp Ala Val Leu Phe Leu Cys Cys Ala Trp Tyr Val
    770                 775                 780

Lys Gly Arg Leu Val Pro Ala Cys Thr Tyr Met Ala Leu Gly Met Trp
785                 790                 795                 800

Pro Leu Leu Leu Thr Ile Leu Ala Leu Pro Arg Arg Ala Tyr Ala Met
                805                 810                 815

Asp Asn Glu Gln Ala Ala Ser Leu Gly Ala Val Gly Leu Leu Val Leu
            820                 825                 830

Thr Ile Phe Thr Ile Thr Pro Met Tyr Lys Lys Leu Leu Thr Cys Ser
    835                 840                 845

Ile Trp Trp Asn Gln Tyr Phe Leu Ala Arg Ala Glu Ala Met Ile His
    850                 855                 860

Glu Trp Val Pro Asp Leu Arg Val Arg Gly Gly Arg Asp Ser Ile Ile
865                 870                 875                 880

Leu Leu Thr Cys Leu Leu His Pro Gln Leu Gly Phe Glu Val Thr Lys
                885                 890                 895
```

```
Ile Leu Leu Ala Ile Leu Ala Pro Leu Tyr Ile Leu Gln Tyr Ser Leu
            900                 905                 910

Leu Lys Val Pro Tyr Phe Val Arg Ala His Val Leu Leu Arg Ala Cys
        915                 920                 925

Leu Leu Val Arg Arg Leu Ala Gly Gly Lys Tyr Val Gln Ala Cys Leu
        930                 935                 940

Leu Arg Leu Gly Ala Trp Thr Gly Thr Phe Val Tyr Asp His Leu Ala
945                 950                 955                 960

Pro Leu Ser Asp Trp Ala Ser Asp Gly Leu Arg Asp Leu Ala Val Ala
            965                 970                 975

Ile Glu Pro Val Ile Phe Ser Pro Met Glu Lys Lys Ile Ile Thr Trp
            980                 985                 990

Gly Ala Asp Thr Ala Ala Cys Gly Asp Ile Leu Ser Gly Leu Pro Val
            995                1000                1005

Ser Ala Arg Leu Gly Asn Leu Val Leu Leu Gly Pro Ala Asp Asp
    1010                1015                1020

Met Gln Arg Gly Gly Trp Lys Leu Leu Ala Pro Ile Thr Ala Tyr
    1025                1030                1035

Ala Gln Gln Thr Arg Gly Leu Leu Gly Ala Ile Val Val Ser Met
    1040                1045                1050

Thr Gly Arg Asp Arg Thr Glu Gln Ala Gly Glu Val Gln Ile Leu
    1055                1060                1065

Ser Thr Val Ser Gln Ser Phe Leu Gly Thr Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Gly Thr Lys Ser Leu Glu Pro
    1115                1120                1125

Cys Lys Cys Gly Ala Val Asp Leu Tyr Leu Val Thr Arg Asn Ala
    1130                1135                1140

Asp Val Ile Pro Ala Arg Arg Arg Gly Asp Lys Arg Gly Ala Leu
    1145                1150                1155

Leu Ser Pro Arg Pro Ile Ser Thr Leu Lys Gly Ser Ser Gly Gly
    1160                1165                1170

Pro Val Leu Cys Pro Arg Gly His Val Val Gly Leu Phe Arg Ala
    1175                1180                1185

Ala Val Cys Ser Arg Gly Val Ala Lys Ser Ile Asp Phe Ile Pro
    1190                1195                1200

Val Glu Thr Leu Asp Val Val Thr Arg Ser Pro Thr Phe Ser Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Lys Val Pro Val
    1235                1240                1245

Ala Tyr Ala Ala Gln Gly Tyr Lys Val Leu Val Leu Asn Pro Ser
    1250                1255                1260

Val Ala Ala Thr Leu Gly Phe Gly Ala Tyr Leu Ser Lys Ala His
    1265                1270                1275

Gly Ile Asn Pro Asn Ile Arg Thr Gly Val Arg Thr Val Met Thr
    1280                1285                1290

Gly Glu Ala Ile Thr Tyr Ser Thr Tyr Gly Lys Phe Leu Ala Asp
```

|  |  |  |
| --- | --- | --- |
| 1295 | 1300 | 1305 |

Gly Gly Cys Ala Ser Gly Ala Tyr Asp Ile Ile Ile Cys Asp Glu
    1310                1315                1320

Cys His Ala Val Asp Ala Thr Ser Ile Leu Gly Ile Gly Thr Val
    1325                1330                1335

Leu Asp Gln Ala Glu Thr Ala Gly Val Arg Leu Thr Val Leu Ala
    1340                1345                1350

Thr Ala Thr Pro Pro Gly Ser Val Thr Pro His Pro Asp Ile
    1355                1360                1365

Glu Glu Val Gly Leu Gly Arg Glu Gly Glu Ile Pro Phe Tyr Gly
    1370                1375                1380

Arg Ala Ile Pro Leu Ser Cys Ile Lys Gly Gly Arg His Leu Ile
    1385                1390                1395

Phe Cys His Ser Lys Lys Lys Cys Asp Glu Leu Ala Ala Ala Leu
    1400                1405                1410

Arg Gly Met Gly Leu Asn Ala Val Ala Tyr Tyr Arg Gly Leu Asp
    1415                1420                1425

Val Ser Ile Ile Pro Ala Gln Gly Asp Val Val Val Ala Thr
    1430                1435                1440

Asp Ala Leu Met Thr Gly Tyr Thr Gly Asp Phe Asp Ser Val Ile
    1445                1450                1455

Asp Cys Asn Val Ala Val Thr Gln Ala Val Asp Phe Ser Leu Asp
    1460                1465                1470

Pro Thr Phe Thr Ile Thr Thr Gln Thr Val Pro Gln Asp Ala Val
    1475                1480                1485

Ser Arg Ser Gln Arg Arg Gly Arg Thr Gly Arg Gly Arg Gln Gly
    1490                1495                1500

Thr Tyr Arg Tyr Val Ser Thr Gly Glu Arg Ala Ser Gly Met Phe
    1505                1510                1515

Asp Ser Val Val Leu Cys Glu Cys Tyr Asp Ala Gly Ala Ala Trp
    1520                1525                1530

Tyr Asp Leu Thr Pro Ala Glu Thr Thr Val Arg Leu Arg Ala Tyr
    1535                1540                1545

Phe Asn Thr Pro Gly Leu Pro Val Cys Gln Asp His Leu Glu Phe
    1550                1555                1560

Trp Glu Ala Val Phe Thr Gly Leu Thr His Ile Asp Ala His Phe
    1565                1570                1575

Leu Ser Gln Thr Lys Gln Ala Gly Glu Asn Phe Ala Tyr Leu Val
    1580                1585                1590

Ala Tyr Gln Ala Thr Val Cys Ala Arg Ala Lys Ala Pro Pro Pro
    1595                1600                1605

Ser Trp Asp Ala Met Trp Lys Cys Leu Ala Arg Leu Lys Pro Thr
    1610                1615                1620

Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680

Gly Cys Val Ser Ile Ile Gly Arg Leu His Val Asn Gln Arg Val
    1685                1690                1695

-continued

Val Val Ala Pro Asp Lys Glu Val Leu Tyr Glu Ala Phe Asp Glu
1700                1705                1710

Met Glu Glu Cys Ala Ser Arg Ala Ala Leu Ile Glu Glu Gly Gln
1715                1720                1725

Arg Ile Ala Glu Met Leu Lys Ser Lys Ile Gln Gly Leu Leu Gln
1730                1735                1740

Gln Ala Ser Lys Gln Ala Gln Asp Ile Gln Pro Ala Met Gln Ala
1745                1750                1755

Ser Trp Pro Lys Val Glu Gln Phe Trp Ala Arg His Met Trp Asn
1760                1765                1770

Phe Ile Ser Gly Ile Gln Tyr Leu Ala Gly Leu Ser Thr Leu Pro
1775                1780                1785

Gly Asn Pro Ala Val Ala Ser Met Met Ala Phe Ser Ala Ala Leu
1790                1795                1800

Thr Ser Pro Leu Ser Thr Ser Thr Thr Ile Leu Leu Asn Ile Met
1805                1810                1815

Gly Gly Trp Leu Ala Ser Gln Ile Ala Pro Pro Ala Gly Ala Thr
1820                1825                1830

Gly Phe Val Val Ser Gly Leu Val Gly Ala Ala Val Gly Ser Ile
1835                1840                1845

Gly Leu Gly Lys Val Leu Val Asp Ile Leu Ala Gly Tyr Gly Ala
1850                1855                1860

Gly Ile Ser Gly Ala Leu Val Ala Phe Lys Ile Met Ser Gly Glu
1865                1870                1875

Lys Pro Ser Met Glu Asp Val Ile Asn Leu Leu Pro Gly Ile Leu
1880                1885                1890

Ser Pro Gly Ala Leu Val Val Gly Val Ile Cys Ala Ala Ile Leu
1895                1900                1905

Arg Arg His Val Gly Pro Gly Glu Gly Ala Val Gln Trp Met Asn
1910                1915                1920

Arg Leu Ile Ala Phe Ala Ser Arg Gly Asn His Val Ala Pro Thr
1925                1930                1935

His Tyr Val Thr Glu Ser Asp Ala Ser Gln Arg Val Thr Gln Leu
1940                1945                1950

Leu Gly Ser Leu Thr Ile Thr Ser Leu Leu Arg Arg Leu His Asn
1955                1960                1965

Trp Ile Thr Glu Asp Cys Pro Ile Pro Cys Ser Gly Ser Trp Leu
1970                1975                1980

Arg Asp Val Trp Asp Trp Val Cys Thr Ile Leu Thr Asp Phe Lys
1985                1990                1995

Asn Trp Leu Thr Ser Lys Leu Phe Pro Lys Leu Pro Gly Leu Pro
2000                2005                2010

Phe Ile Ser Cys Gln Lys Gly Tyr Lys Gly Val Trp Ala Gly Thr
2015                2020                2025

Gly Ile Met Thr Thr Arg Cys Pro Cys Gly Ala Asn Ile Ser Gly
2030                2035                2040

Asn Val Arg Leu Gly Ser Met Arg Ile Thr Gly Pro Lys Thr Cys
2045                2050                2055

Met Asn Thr Trp Gln Gly Thr Phe Pro Ile Asn Cys Tyr Thr Glu
2060                2065                2070

Gly Gln Cys Ala Pro Lys Pro Pro Thr Asn Tyr Lys Thr Ala Ile
2075                2080                2085

Trp Arg Val Ala Ala Ser Glu Tyr Ala Glu Val Thr Gln His Gly
2090                2095                2100

| | | | | | | | | | | | |
|---|---|---|---|---|---|---|---|---|---|---|---|
| Ser | Tyr | Ser | Tyr | Val | Thr | Gly | Leu | Thr | Thr | Asp | Asn | Leu | Lys | Ile |
| | 2105 | | | | 2110 | | | | 2115 | | |

Ser Tyr Ser Tyr Val Thr Gly Leu Thr Thr Asp Asn Leu Lys Ile
  2105                2110               2115

Pro Cys Gln Leu Pro Ser Pro Glu Phe Phe Ser Trp Val Asp Gly
  2120                2125               2130

Val Gln Ile His Arg Phe Ala Pro Thr Pro Lys Pro Phe Phe Arg
  2135                2140               2145

Asp Glu Val Ser Phe Cys Val Gly Leu Asn Ser Tyr Ala Val Gly
  2150                2155               2160

Ser Gln Leu Pro Cys Glu Pro Glu Pro Asp Ala Asp Val Leu Arg
  2165                2170               2175

Ser Met Leu Thr Asp Pro Pro His Ile Thr Ala Glu Thr Ala Ala
  2180                2185               2190

Arg Arg Leu Ala Arg Gly Ser Pro Pro Ser Glu Ala Ser Ser Ser
  2195                2200               2205

Val Ser Gln Leu Ser Ala Pro Ser Leu Arg Ala Thr Cys Thr Thr
  2210                2215               2220

His Ser Asn Thr Tyr Asp Val Asp Met Val Asp Ala Asn Leu Leu
  2225                2230               2235

Met Glu Gly Gly Val Ala Gln Thr Glu Pro Glu Ser Arg Val Pro
  2240                2245               2250

Val Leu Asp Phe Leu Glu Pro Met Ala Glu Glu Ser Asp Leu
  2255                2260               2265

Glu Pro Ser Ile Pro Ser Glu Cys Met Leu Pro Arg Ser Gly Phe
  2270                2275               2280

Pro Arg Ala Leu Pro Ala Trp Ala Arg Pro Asp Tyr Asn Pro Pro
  2285                2290               2295

Leu Val Glu Ser Trp Arg Arg Pro Asp Tyr Gln Pro Pro Thr Val
  2300                2305               2310

Ala Gly Cys Ala Leu Pro Pro Pro Lys Lys Ala Pro Thr Pro Pro
  2315                2320               2325

Pro Arg Arg Arg Arg Thr Val Gly Leu Ser Glu Ser Thr Ile Ser
  2330                2335               2340

Glu Ala Leu Gln Gln Leu Ala Ile Lys Thr Phe Gly Gln Pro Pro
  2345                2350               2355

Ser Ser Gly Asp Ala Gly Ser Ser Thr Gly Ala Gly Ala Ala Glu
  2360                2365               2370

Ser Gly Gly Pro Thr Ser Pro Gly Glu Pro Ala Pro Ser Glu Thr
  2375                2380               2385

Gly Ser Ala Ser Ser Met Pro Pro Leu Glu Gly Glu Pro Gly Asp
  2390                2395               2400

Pro Asp Leu Glu Ser Asp Gln Val Glu Leu Gln Pro Pro Pro Gln
  2405                2410               2415

Gly Gly Gly Val Ala Pro Gly Ser Gly Ser Gly Ser Trp Ser Thr
  2420                2425               2430

Cys Ser Glu Glu Asp Asp Thr Thr Val Cys Cys Ser Met Ser Tyr
  2435                2440               2445

Ser Trp Thr Gly Ala Leu Ile Thr Pro Cys Ser Pro Glu Glu Glu
  2450                2455               2460

Lys Leu Pro Ile Asn Pro Leu Ser Asn Ser Leu Leu Arg Tyr His
  2465                2470               2475

Asn Lys Val Tyr Cys Thr Thr Ser Lys Ser Ala Ser Gln Arg Ala
  2480                2485               2490

Lys Lys Val Thr Phe Asp Arg Thr Gln Val Leu Asp Ala His Tyr

-continued

```
              2495                2500               2505

Asp  Ser  Val  Leu  Lys  Asp  Ile  Lys  Leu  Ala  Ala  Ser  Lys  Val  Ser
         2510                2515               2520

Ala  Arg  Leu  Leu  Thr  Leu  Glu  Glu  Ala  Cys  Gln  Leu  Thr  Pro  Pro
         2525                2530               2535

His  Ser  Ala  Arg  Ser  Lys  Tyr  Gly  Phe  Gly  Ala  Lys  Glu  Val  Arg
         2540                2545               2550

Ser  Leu  Ser  Gly  Arg  Ala  Val  Asn  His  Ile  Lys  Ser  Val  Trp  Lys
         2555                2560               2565

Asp  Leu  Leu  Glu  Asp  Pro  Gln  Thr  Pro  Ile  Pro  Thr  Thr  Ile  Met
         2570                2575               2580

Ala  Lys  Asn  Glu  Val  Phe  Cys  Val  Asp  Pro  Ala  Lys  Gly  Gly  Lys
         2585                2590               2595

Lys  Pro  Ala  Arg  Leu  Ile  Val  Tyr  Pro  Asp  Leu  Gly  Val  Arg  Val
         2600                2605               2610

Cys  Glu  Lys  Met  Ala  Leu  Tyr  Asp  Ile  Thr  Gln  Lys  Leu  Pro  Gln
         2615                2620               2625

Ala  Val  Met  Gly  Ala  Ser  Tyr  Gly  Phe  Gln  Tyr  Ser  Pro  Ala  Gln
         2630                2635               2640

Arg  Val  Glu  Tyr  Leu  Leu  Lys  Ala  Trp  Ala  Glu  Lys  Lys  Asp  Pro
         2645                2650               2655

Met  Gly  Phe  Ser  Tyr  Asp  Thr  Arg  Cys  Phe  Asp  Ser  Thr  Val  Thr
         2660                2665               2670

Glu  Arg  Asp  Ile  Arg  Thr  Glu  Glu  Ser  Ile  Tyr  Gln  Ala  Cys  Ser
         2675                2680               2685

Leu  Pro  Glu  Glu  Ala  Arg  Thr  Ala  Ile  His  Ser  Leu  Thr  Glu  Arg
         2690                2695               2700

Leu  Tyr  Val  Gly  Gly  Pro  Met  Phe  Asn  Ser  Lys  Gly  Gln  Thr  Cys
         2705                2710               2715

Gly  Tyr  Arg  Arg  Cys  Arg  Ala  Ser  Gly  Val  Leu  Thr  Thr  Ser  Met
         2720                2725               2730

Gly  Asn  Thr  Ile  Thr  Cys  Tyr  Val  Lys  Ala  Leu  Ala  Ala  Cys  Lys
         2735                2740               2745

Ala  Ala  Gly  Ile  Val  Ala  Pro  Thr  Met  Leu  Val  Cys  Gly  Asp  Asp
         2750                2755               2760

Leu  Val  Val  Ile  Ser  Glu  Ser  Gln  Gly  Thr  Glu  Glu  Asp  Glu  Arg
         2765                2770               2775

Asn  Leu  Arg  Ala  Phe  Thr  Glu  Ala  Met  Thr  Arg  Tyr  Ser  Ala  Pro
         2780                2785               2790

Pro  Gly  Asp  Pro  Pro  Arg  Pro  Glu  Tyr  Asp  Leu  Glu  Leu  Ile  Thr
         2795                2800               2805

Ser  Cys  Ser  Ser  Asn  Val  Ser  Val  Ala  Leu  Gly  Pro  Arg  Gly  Arg
         2810                2815               2820

Arg  Arg  Tyr  Tyr  Leu  Thr  Arg  Asp  Pro  Thr  Thr  Pro  Leu  Ala  Arg
         2825                2830               2835

Ala  Ala  Trp  Glu  Thr  Val  Arg  His  Ser  Pro  Ile  Asn  Ser  Trp  Leu
         2840                2845               2850

Gly  Asn  Ile  Ile  Gln  Tyr  Ala  Pro  Thr  Ile  Trp  Val  Arg  Met  Val
         2855                2860               2865

Leu  Met  Thr  His  Phe  Phe  Ser  Ile  Leu  Met  Val  Gln  Asp  Thr  Leu
         2870                2875               2880

Asp  Gln  Asn  Leu  Asn  Phe  Glu  Met  Tyr  Gly  Ser  Val  Tyr  Ser  Val
         2885                2890               2895
```

```
Asn Pro  Leu Asp Leu Pro  Ala Ile Ile Glu Arg  Leu His Gly Leu
    2900         2905                 2910

Asp Ala  Phe Ser Met His  Thr Tyr Ser His His  Glu Leu Thr Arg
    2915         2920                 2925

Val Ala  Ser Ala Leu Arg  Lys Leu Gly Ala Pro  Pro Leu Arg Val
    2930         2935                 2940

Trp Lys  Ser Arg Ala Arg  Ala Val Arg Ala Ser  Leu Ile Ser Arg
    2945         2950                 2955

Gly Gly  Lys Ala Ala Val  Cys Gly Arg Tyr Leu  Phe Asn Trp Ala
    2960         2965                 2970

Val Lys  Thr Lys Leu Lys  Leu Thr Pro Leu Pro  Glu Ala Arg Leu
    2975         2980                 2985

Leu Asp  Leu Ser Ser Trp  Phe Thr Val Gly Ala  Gly Gly Gly Asp
    2990         2995                 3000

Ile Phe  His Ser Val Ser  Arg Ala Arg Pro Arg  Ser Leu Leu Phe
    3005         3010                 3015

Gly Leu  Leu Leu Leu Phe  Val Gly Val Gly Leu  Phe Leu Leu Pro
    3020         3025                 3030

Ala Arg
    3035

<210> SEQ ID NO 3
<211> LENGTH: 9684
<212> TYPE: DNA
<213> ORGANISM: Hepatitis C virus

<400> SEQUENCE: 3
acctgcccct aatagggcg  acactccgcc atgaatcact  cccctgtgag gaactactgt     60
cttcacgcag aaagcgccta gccatggcgt  tagtatgagt gtcgtacagc  ctccaggccc    120 cccccctcccg ggagagccat agtggtctgc ggaaccggtg agtacaccgg aattgccggg    180
aagactgggt cctttcttgg ataaacccac tctatgcccg ccatttgggt cgtgccccccg    240 caagactgct agccgagtag cgttgggttg cgaaaggcct tgtggtactg cctgataggg    300
tgcttgcgag tgccccggga ggtctcgtag accgtgcacc atgagcacac ttccaaaacc    360
ccaaagaaaa accaaaagaa acaccaaccg tcgcccaatg acgtcaagt tcccgggtgg    420 cggtcagatc gttggcggag tttacttgtt gccgcgcagg ggccccggt tgggtgtgcg    480 cgcgacgagg aagacttccg agcgatccca gcccagaggc aggcgccaac ctataccaaa    540
ggcgcgccag cccagggca ggcactgggc tcagcccgga tatccttggc ccctttatgg    600
gaacgagggc tgtgggtggg caggttggct cctgtccccc gcggctcccc ggccacactg    660
gggccccaac gaccccggc gtcgatcccg gaatttgggt aaggtcatcg atacccctaac    720 gtgtgggttc gccgatctca tggggtacat tcccgtcgtg ggcgcgcctt tgggcggcgt    780
cgcggctgca ctcgcacatg gtgtgagggc aatcgaggac gggatcaatt atgcaacagg    840
gaatcttccc ggttgctctt tctctatctt cctcttggca ctactctcgt gcctcacaac    900
gccagcgtcg gctcttacct acggtaactc cagtgggcta ccatcttaca aaatgattg    960 ccccaactcc agcatcgtgc tggaggcgga tgccatgatc ttgcattttgc ctggatgctt    1020 gccttgtgtg agggtcaata acaaccagtc catctgttgg catgctgtgt ccccacccct    1080
agccatacca aatgcttcca cacctgcaac gggattccgt aggcatgtgg accttcttgc    1140
gggcgccgca gtggtttgct catccctgta catcggggat ctgtgcggct ccctctttttt    1200 ggcagggcaa ctatttacct ttcagccccg ccgtcactgg actgtgcaag actgcaactg    1260
```

```
ctccatttat acaggccacg tcaccggcca caggatggct tgggacatga tgatgaattg    1320
gtcacccaca accactctgg tcctatctag tatcttgagg gtacctgaga tctgtgcgag    1380
tgtgatatct ggtggccatt gggggatact actagccgtt gcctactttg gtatggctgg    1440
caactggcta aaagttctgg ctgtcctgtt cttatttgca ggggttgaag caaccaccac    1500
catcggccat caagtaggcc gcactactgg tggcttagcc agtctcttct ccatcggtcc    1560
caggcaaaat ctacaactca tcaacaccaa tggcagctgg catataaaca ggactgctct    1620
gaactgcaat gattccctcc agacggggtt cataacgtca ctcttttatg ccaagaacgt    1680
caactcctcg ggctgcccag agcggatggc tgcgtgtaag cccctcgcgg acttccggca    1740
ggggtggggc caaataacct acaaagtcaa catctcgggc ccctccgacg accgtcccta    1800
ctgttggcat tacgctccca ggccatgtga cgtggtgtcg gcccgcacgg tgtgcggccc    1860
cgtttactgc ttcacgccca gccctgtcgt agtaggaacc actgacaagc tgggcattcc    1920
cacatacaac tgggggagaga atgagacgga tgtgttcatg ttggaaagcc ttcggcctcc    1980
tactggagga tggtttgggt gcacgtggat gaactctacg ggctttacca agacctgtgg    2040
tgccccgcca tgtcagatag tcccgggaga ttacaatagc tctgccaatg agcttttgtg    2100
ccccaccgac tgcttccgta acatccggaa gctacatat cagcggtgtg gatcgggacc    2160
ctggatcaca cctaggtgtc tggtggatta cccctacagg ctgtggcact accctgtac    2220
tgtcaacttc accttgcata agtcaggat gttcgtggga ggcattgagc atcggtttga    2280
cgccgcatgt aactggacca gaggcgagcg gtgtgatcta catgacagag acaggattga    2340
aatgagcccg ctgcttttct caactacgca gcttgccata cttccctgtt cattttccac    2400
catgccggcc ttgtcaaccg gcctcatcca cctgcatcag aacatagtgg acgtgcagta    2460
cctctacgga gtcctcga gcgttacctc gtgggtggtg aagtgggagt acattgttct    2520
ggtgttcctg gttctggcag atgctcggat ttgtacatgt ctctggttaa tgctgctcat    2580
aaccaacgtt gaagcagcag tggaaaggct tgtcgtcctc aatgcggcta cgccgccgg    2640
caccgccggc tggtggtggg cggtgctctt cctgtgctgt gcttggtacg tgaaaggccg    2700
ccttgtgcct gcgtgtacct acatggcact gggaatgtgg ccgttgctcc tgacaatctt    2760
ggccctgcct cgccgagcat acgctatgga caatgagcaa gcggcatccc tcggagctgt    2820
tggtctcttg gtgctcacca tctttaccat caccccatg tacaagaagc tgttgacctg    2880
ctccatttgg tggaatcagt atttcctcgc ccgagctgag gccatgatac acgagtgggt    2940
gcccgaccta cgggttaggg gcggtaggga ctccatcatc ttacttacct gcttgttaca    3000
tccacagctg gggtttgagg tcaccaaaat tctactagcc atcctggccc ctctatacat    3060
cctgcagtac agtttgctca aggtgcctta ctttgtgcgc gccacgtac tcctgcgtgc    3120
ttgcctgctt gttcgtaggc tagcaggggg taagtacgtg caggcgtgcc ttctgaggtt    3180
gggcgcttgg actggcacct ttgtctatga ccatctcgcc cctctctctg actgggctag    3240
cgacggactg cgcgatttgg cagtcgcaat cgagccggtc attttctctc ccatggagaa    3300
gaaaatcatt acctgggtg cggataccgc gcgtgtggt gacatcttga gtggcctccc    3360
ggtgtcagcg aggttgggga atttggtgct actgggaccc gcggacgata tgcagcgcgg    3420
gggttggaag cttttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
```

-continued

```
ctcgagtgct gaggggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840
gaagggtcc tcgggggggc cggtgctctg ccctaggggc cacgtcgttg ggctcttccg     3900
agcagctgtg tgctctcggg gcgtggccaa atccatcgat ttcatcccccg ttgagacact   3960
cgacgttgtt acaaggtctc ccactttcag tgacaacagc acgccaccgg ctgtgcccca   4020
gacctatcag gtcgggtact tgcatgctcc aactggcagt ggaaagagca ccaaggtccc   4080
tgtcgcgtat gccgcccagg ggtacaaagt actagtgctt aaccccctcgg tagctgccac  4140
cctggggttt ggggcgtacc tatccaaggc acatggcatc aatcccaaca ttaggactgg   4200
agtcaggacc gtgatgaccg gggaggccat cacgtactcc acatatggca aatttctcgc   4260
cgatgggggc tgcgctagcg gcgcctatga catcatcata tgcgatgaat gccacgctgt   4320
ggatgctacc tccattctcg gcatcggaac ggtccttgat caagcagaga cagccggggt   4380
cagactaact gtgctggcta cggccacacc ccccgggtca gtgacaaccc ccatcccga    4440
tatagaagag gtaggcctcg gcgggaggg tgagatcccc ttctatggga gggcgattcc    4500
cctatcctgc atcaagggag ggagacacct gattttctgc cactcaaaga aaaagtgtga   4560
cgagctcgcg gcgcccttc ggggcatggg cttgaatgcc gtggcatact atagagggtt    4620
ggacgtctcc ataataccag ctcagggaga tgtggtggtc gtcgccaccg acgccctcat   4680
gacggggtac actggagact ttgactccgt gatcgactgc aatgtagcgg tcacccaagc   4740
tgtcgacttc agcctggacc ccaccttcac tataaccaca cagactgtcc cacaagacgc   4800
tgtctcacgc agtcagcgcc gcgggcgcac aggtagagga agacagggca cttataggta   4860
tgtttccact ggtgaacgag cctcaggaat gtttgacagt gtagtgcttt gtgagtgcta   4920
cgacgcaggg gctgcgtggt acgatctcac accagcggag accaccgtca ggcttagagc   4980
gtatttcaac acgcccggcc tacccgtgtg tcaagaccat cttgaatttt gggaggcagt   5040
tttcaccggc ctcacacaca tagacgccca cttcctctcc caaacaaagc aagcggggga   5100
gaacttcgcg tacctagtag cctaccaagc tacggtgtgc gccagagcca aggcccctcc   5160
cccgtcctgg gacgccatgt ggaagtgcct ggcccgactc aagcctacgc ttgcgggccc   5220
cacacctctc ctgtaccgtt tgggccctat taccaatgag gtcacccctca cacacctgg   5280
gacgaagtac atcgccacat gcatgcaagc tgaccttgag gtcatgacca gcacgtgggt   5340
cctagctgga ggagtcctgg cagccgtcgc cgcatattgc ctggcgactg gatgcgtttc   5400
catcatcggc cgcttgcacg tcaaccagcg agtcgtcgtt gcgccggata aggaggtcct   5460
gtatgaggct tttgatgaga tggaggaatg cgcctctagg gcggctctca tcgaagaggg   5520
gcagcggata gccgagatgt tgaagtccaa gatccaaggc ttgctgcagc aggcctctaa   5580
gcaggcccag gacatacaac ccgctatgca ggcttcatgg cccaaagtgg aacaattttg   5640
ggccagacac atgtggaact tcattagcgg catccaatac ctcgcaggat tgtcaacact   5700
gccagggaac cccgcggtgg cttccatgat ggcattcagt gccgccctca ccagtccgtt   5760
gtcgaccagt accaccatcc ttctcaacat catgggaggc tggttagcgt cccagatcgc   5820
accacccgcg ggggccaccg gctttgtcgt cagtggcctg gtgggggctg ccgtgggcag   5880
cataggcctg ggtaaggtgc tggtggacat cctggcagga tatggtgcgg gcatttcggg   5940
ggccctcgtc gcattcaaga tcatgtctgg cgagaagccc tctatggaag atgtcatcaa   6000
tctactgcct gggatcctgt ctccgggagc cctggtggtg ggggtcatct gcgcggccat   6060
```

-continued

```
tctgcgccgc cacgtgggac cggggagggg cgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaagggg tacaagggtg tgtgggccgg     6420
cactggcatc atgaccacgc gctgcccttg cggcgccaac atctctggca atgtccgcct    6480
gggctctatg aggatcacag ggcctaaaac ctgcatgaac acctggcagg gacctttcc     6540 tatcaattgc tacacggagg ccagtgcgc gccgaaaccc cccacgaact acaagaccgc     6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtgacggtg tgcagatcca taggtttgca cccacaccaa agccgttttt     6780
ccgggatgag gtctcgttct cgttgggct taattcctat gctgtcgggt cccagcttcc     6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt ctccgagcca atggccgagg aagagagcga    7140
ccttgagccc tcaataccat cggagtgcat gctccccagg agcgggtttc cacgggcctt    7200
accggcttgg gcacgccctg actacaaccc gccgctcgtg aatcgtgga ggaggccaga     7260 ttaccaaccg cccaccgttg ctggttgtgc tctccccccc cccaagaagg ccccgacgcc    7320
tcccccaagg agacgccgga cagtgggtct gagcgagagc accatatcag aagccctcca    7380
gcaactggcc atcaagacct ttggccagcc ccctcgagc ggtgatgcag gctcgtccac     7440
gggggcgggc gccgccgaat ccggcggtcc gacgtcccct ggtgagccgg cccctcaga    7500 gacaggttcc gcctcctcta tgccccccct cgaggggag cctggagatc cggacctgga    7560
gtctgatcag gtagagcttc aacctcccccc ccaggggggg ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740
caaccctttg agtaactcgc tgttgcgata ccataacaag gtgtactgta acatcaaa     7800 gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca gtatggatt    7980 cggggccaag gaggtccgca gcttgtccgg gagggccgtt aaccacatca gtccgtgtg     8040 gaaggacctc ctggaagacc cacaaacacc aattcccaca accatcatgg ccaaaaatga    8100
ggtgttctgc gtgacccccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
```

```
agggcccatg ttcaacagca agggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc cccagaccg aatatgacc tggagctaat    8760 aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct tctccattct catggtccaa gacaccctgg accagaacct    9000
caactttgag atgtatggat cagtatactc cgtgaatcct ttggaccttc agccataat    9060 tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttttcacag    9360 cgtgtcgcgc gcccgacccc gctcattact cttcggccta ctcctacttt tcgtaggggt    9420
aggcctcttc ctactccccg ctcggtagag cggcacacac taggtacact ccatagctaa    9480
ctgttccttt tttttttttt tttttttttt tttttttttt tttttttttt ctttttttt    9540 ttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt    9684
```

<210> SEQ ID NO 4
<211> LENGTH: 3035
<212> TYPE: PRT
<213> ORGANISM: Hepatitis C virus

<400> SEQUENCE: 4

```
Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Gly Gly Val Ala Ala Ala Leu Ala His Gly Val Arg Ala Ile Glu Asp
145                 150                 155                 160
```

-continued

```
Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
        195                 200                 205

Asn Ser Ser Ile Val Leu Glu Ala Asp Ala Met Ile Leu His Leu Pro
    210                 215                 220

Gly Cys Leu Pro Cys Val Arg Val Asn Asn Gln Ser Ile Cys Trp
225                 230                 235                 240

His Ala Val Ser Pro Thr Leu Ala Ile Pro Asn Ala Ser Thr Pro Ala
                245                 250                 255

Thr Gly Phe Arg Arg His Val Asp Leu Leu Ala Gly Ala Ala Val Val
            260                 265                 270

Cys Ser Ser Leu Tyr Ile Gly Asp Leu Cys Gly Ser Leu Phe Leu Ala
        275                 280                 285

Gly Gln Leu Phe Thr Phe Gln Pro Arg Arg His Trp Thr Val Gln Asp
    290                 295                 300

Cys Asn Cys Ser Ile Tyr Thr Gly His Val Thr Gly His Arg Met Ala
305                 310                 315                 320

Trp Asp Met Met Met Asn Trp Ser Pro Thr Thr Thr Leu Val Leu Ser
                325                 330                 335

Ser Ile Leu Arg Val Pro Glu Ile Cys Ala Ser Val Ile Ser Gly Gly
            340                 345                 350

His Trp Gly Ile Leu Leu Ala Val Ala Tyr Phe Gly Met Ala Gly Asn
        355                 360                 365

Trp Leu Lys Val Leu Ala Val Leu Phe Leu Phe Ala Gly Val Glu Ala
    370                 375                 380

Thr Thr Thr Ile Gly His Gln Val Gly Arg Thr Thr Gly Gly Leu Ala
385                 390                 395                 400

Ser Leu Phe Ser Ile Gly Pro Arg Gln Asn Leu Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Thr Ser Leu Phe Tyr Ala Lys Asn Val Asn
        435                 440                 445

Ser Ser Gly Cys Pro Glu Arg Met Ala Ala Cys Lys Pro Leu Ala Asp
    450                 455                 460

Phe Arg Gln Gly Trp Gly Gln Ile Thr Tyr Lys Val Asn Ile Ser Gly
465                 470                 475                 480

Pro Ser Asp Asp Arg Pro Tyr Cys Trp His Tyr Ala Pro Arg Pro Cys
                485                 490                 495

Asp Val Val Ser Ala Arg Thr Val Cys Gly Pro Val Tyr Cys Phe Thr
            500                 505                 510

Pro Ser Pro Val Val Gly Thr Thr Asp Lys Leu Gly Ile Pro Thr
        515                 520                 525

Tyr Asn Trp Gly Glu Asn Glu Thr Asp Val Phe Met Leu Glu Ser Leu
    530                 535                 540

Arg Pro Pro Thr Gly Gly Trp Phe Gly Cys Thr Trp Met Asn Ser Thr
545                 550                 555                 560

Gly Phe Thr Lys Thr Cys Gly Ala Pro Pro Cys Gln Ile Val Pro Gly
                565                 570                 575

Asp Tyr Asn Ser Ser Ala Asn Glu Leu Leu Cys Pro Thr Asp Cys Phe
            580                 585                 590
```

-continued

```
Arg Lys His Pro Glu Ala Thr Tyr Gln Arg Cys Gly Ser Gly Pro Trp
        595                 600                 605
Ile Thr Pro Arg Cys Leu Val Asp Tyr Pro Tyr Arg Leu Trp His Tyr
610                 615                 620
Pro Cys Thr Val Asn Phe Thr Leu His Lys Arg Met Phe Val Gly
625                 630                 635                 640
Gly Ile Glu His Arg Phe Asp Ala Ala Cys Asn Trp Thr Arg Gly Glu
                645                 650                 655
Arg Cys Asp Leu His Asp Arg Asp Arg Ile Glu Met Ser Pro Leu Leu
                660                 665                 670
Phe Ser Thr Thr Gln Leu Ala Ile Leu Pro Cys Ser Phe Ser Thr Met
            675                 680                 685
Pro Ala Leu Ser Thr Gly Leu Ile His Leu His Gln Asn Ile Val Asp
690                 695                 700
Val Gln Tyr Leu Tyr Gly Val Ser Ser Val Thr Ser Trp Val Val
705                 710                 715                 720
Lys Trp Glu Tyr Ile Val Leu Phe Leu Val Leu Ala Asp Ala Arg
                725                 730                 735
Ile Cys Thr Cys Leu Trp Leu Met Leu Leu Ile Thr Asn Val Glu Ala
                740                 745                 750
Ala Val Glu Arg Leu Val Val Leu Asn Ala Ala Ser Ala Ala Gly Thr
            755                 760                 765
Ala Gly Trp Trp Trp Ala Val Leu Phe Leu Cys Cys Ala Trp Tyr Val
    770                 775                 780
Lys Gly Arg Leu Val Pro Ala Cys Thr Tyr Met Ala Leu Gly Met Trp
785                 790                 795                 800
Pro Leu Leu Leu Thr Ile Leu Ala Leu Pro Arg Arg Ala Tyr Ala Met
                805                 810                 815
Asp Asn Glu Gln Ala Ala Ser Leu Gly Ala Val Gly Leu Leu Val Leu
                820                 825                 830
Thr Ile Phe Thr Ile Thr Pro Met Tyr Lys Lys Leu Leu Thr Cys Ser
            835                 840                 845
Ile Trp Trp Asn Gln Tyr Phe Leu Ala Arg Ala Glu Ala Met Ile His
    850                 855                 860
Glu Trp Val Pro Asp Leu Arg Val Arg Gly Gly Arg Asp Ser Ile Ile
865                 870                 875                 880
Leu Leu Thr Cys Leu Leu His Pro Gln Leu Gly Phe Glu Val Thr Lys
                885                 890                 895
Ile Leu Leu Ala Ile Leu Ala Pro Leu Tyr Ile Leu Gln Tyr Ser Leu
            900                 905                 910
Leu Lys Val Pro Tyr Phe Val Arg Ala His Val Leu Leu Arg Ala Cys
    915                 920                 925
Leu Leu Val Arg Arg Leu Ala Gly Gly Lys Tyr Val Gln Ala Cys Leu
    930                 935                 940
Leu Arg Leu Gly Ala Trp Thr Gly Thr Phe Val Tyr Asp His Leu Ala
945                 950                 955                 960
Pro Leu Ser Asp Trp Ala Ser Asp Gly Leu Arg Asp Leu Ala Val Ala
                965                 970                 975
Ile Glu Pro Val Ile Phe Ser Pro Met Glu Lys Lys Ile Ile Thr Trp
            980                 985                 990
Gly Ala Asp Thr Ala Ala Cys Gly  Asp Ile Leu Ser Gly  Leu Pro Val
        995                 1000                 1005
Ser Ala  Arg Leu Gly Asn Leu  Val Leu Leu Gly Pro  Ala Asp Asp
```

-continued

```
             1010                1015                1020
Met Gln Arg Gly Gly Trp Lys Leu Leu Ala Pro Ile Thr Ala Tyr
     1025                1030                1035
Ala Gln Gln Thr Arg Gly Leu Leu Gly Ala Ile Val Val Ser Met
     1040                1045                1050
Thr Gly Arg Asp Arg Thr Glu Gln Ala Gly Glu Val Gln Ile Leu
     1055                1060                1065
Ser Thr Val Ser Gln Ser Phe Leu Gly Thr Ile Ser Gly Val
     1070                1075                1080
Leu Trp Thr Val Tyr His Gly Ala Gly Asn Lys Thr Leu Ala Gly
     1085                1090                1095
Leu Arg Gly Pro Val Thr Gln Met Tyr Ser Ser Ala Glu Gly Asp
     1100                1105                1110
Leu Val Gly Trp Pro Ser Pro Pro Gly Thr Lys Ser Leu Glu Pro
     1115                1120                1125
Cys Lys Cys Gly Ala Val Asp Leu Tyr Leu Val Thr Arg Asn Ala
     1130                1135                1140
Asp Val Ile Pro Ala Arg Arg Gly Asp Lys Arg Gly Ala Leu
     1145                1150                1155
Leu Ser Pro Arg Pro Ile Ser Thr Leu Lys Gly Ser Ser Gly Gly
     1160                1165                1170
Pro Val Leu Cys Pro Arg Gly His Val Val Gly Leu Phe Arg Ala
     1175                1180                1185
Ala Val Cys Ser Arg Gly Val Ala Lys Ser Ile Asp Phe Ile Pro
     1190                1195                1200
Val Glu Thr Leu Asp Val Val Thr Arg Ser Pro Thr Phe Ser Asp
     1205                1210                1215
Asn Ser Thr Pro Pro Ala Val Pro Gln Thr Tyr Gln Val Gly Tyr
     1220                1225                1230
Leu His Ala Pro Thr Gly Ser Gly Lys Ser Thr Lys Val Pro Val
     1235                1240                1245
Ala Tyr Ala Ala Gln Gly Tyr Lys Val Leu Val Leu Asn Pro Ser
     1250                1255                1260
Val Ala Ala Thr Leu Gly Phe Gly Ala Tyr Leu Ser Lys Ala His
     1265                1270                1275
Gly Ile Asn Pro Asn Ile Arg Thr Gly Val Arg Thr Val Met Thr
     1280                1285                1290
Gly Glu Ala Ile Thr Tyr Ser Thr Tyr Gly Lys Phe Leu Ala Asp
     1295                1300                1305
Gly Gly Cys Ala Ser Gly Ala Tyr Asp Ile Ile Ile Cys Asp Glu
     1310                1315                1320
Cys His Ala Val Asp Ala Thr Ser Ile Leu Gly Ile Gly Thr Val
     1325                1330                1335
Leu Asp Gln Ala Glu Thr Ala Gly Val Arg Leu Thr Val Leu Ala
     1340                1345                1350
Thr Ala Thr Pro Pro Gly Ser Val Thr Thr Pro His Pro Asp Ile
     1355                1360                1365
Glu Glu Val Gly Leu Gly Arg Glu Gly Glu Ile Pro Phe Tyr Gly
     1370                1375                1380
Arg Ala Ile Pro Leu Ser Cys Ile Lys Gly Gly Arg His Leu Ile
     1385                1390                1395
Phe Cys His Ser Lys Lys Lys Cys Asp Glu Leu Ala Ala Ala Leu
     1400                1405                1410
```

-continued

Arg Gly Met Gly Leu Asn Ala Val Ala Tyr Tyr Arg Gly Leu Asp
1415                1420                1425

Val Ser Ile Ile Pro Ala Gln Gly Asp Val Val Val Ala Thr
1430                1435                1440

Asp Ala Leu Met Thr Gly Tyr Thr Gly Asp Phe Asp Ser Val Ile
1445                1450                1455

Asp Cys Asn Val Ala Val Thr Gln Ala Val Asp Phe Ser Leu Asp
1460                1465                1470

Pro Thr Phe Thr Ile Thr Thr Gln Thr Val Pro Gln Asp Ala Val
1475                1480                1485

Ser Arg Ser Gln Arg Arg Gly Arg Thr Gly Arg Gly Arg Gln Gly
1490                1495                1500

Thr Tyr Arg Tyr Val Ser Thr Gly Glu Arg Ala Ser Gly Met Phe
1505                1510                1515

Asp Ser Val Val Leu Cys Glu Cys Tyr Asp Ala Gly Ala Ala Trp
1520                1525                1530

Tyr Asp Leu Thr Pro Ala Glu Thr Thr Val Arg Leu Arg Ala Tyr
1535                1540                1545

Phe Asn Thr Pro Gly Leu Pro Val Cys Gln Asp His Leu Glu Phe
1550                1555                1560

Trp Glu Ala Val Phe Thr Gly Leu Thr His Ile Asp Ala His Phe
1565                1570                1575

Leu Ser Gln Thr Lys Gln Ala Gly Glu Asn Phe Ala Tyr Leu Val
1580                1585                1590

Ala Tyr Gln Ala Thr Val Cys Ala Arg Ala Lys Ala Pro Pro Pro
1595                1600                1605

Ser Trp Asp Ala Met Trp Lys Cys Leu Ala Arg Leu Lys Pro Thr
1610                1615                1620

Leu Ala Gly Pro Thr Pro Leu Leu Tyr Arg Leu Gly Pro Ile Thr
1625                1630                1635

Asn Glu Val Thr Leu Thr His Pro Gly Thr Lys Tyr Ile Ala Thr
1640                1645                1650

Cys Met Gln Ala Asp Leu Glu Val Met Thr Ser Thr Trp Val Leu
1655                1660                1665

Ala Gly Gly Val Leu Ala Ala Val Ala Ala Tyr Cys Leu Ala Thr
1670                1675                1680

Gly Cys Val Ser Ile Ile Gly Arg Leu His Val Asn Gln Arg Val
1685                1690                1695

Val Val Ala Pro Asp Lys Glu Val Leu Tyr Glu Ala Phe Asp Glu
1700                1705                1710

Met Glu Glu Cys Ala Ser Arg Ala Ala Leu Ile Glu Glu Gly Gln
1715                1720                1725

Arg Ile Ala Glu Met Leu Lys Ser Lys Ile Gln Gly Leu Leu Gln
1730                1735                1740

Gln Ala Ser Lys Gln Ala Gln Asp Ile Gln Pro Ala Met Gln Ala
1745                1750                1755

Ser Trp Pro Lys Val Glu Gln Phe Trp Ala Arg His Met Trp Asn
1760                1765                1770

Phe Ile Ser Gly Ile Gln Tyr Leu Ala Gly Leu Ser Thr Leu Pro
1775                1780                1785

Gly Asn Pro Ala Val Ala Ser Met Met Ala Phe Ser Ala Ala Leu
1790                1795                1800

Thr Ser Pro Leu Ser Thr Ser Thr Thr Ile Leu Leu Asn Ile Met
1805                1810                1815

-continued

```
Gly Gly Trp Leu Ala Ser Gln Ile Ala Pro Pro Ala Gly Ala Thr
    1820            1825            1830

Gly Phe Val Val Ser Gly Leu Val Gly Ala Ala Val Gly Ser Ile
    1835            1840            1845

Gly Leu Gly Lys Val Leu Val Asp Ile Leu Ala Gly Tyr Gly Ala
    1850            1855            1860

Gly Ile Ser Gly Ala Leu Val Ala Phe Lys Ile Met Ser Gly Glu
    1865            1870            1875

Lys Pro Ser Met Glu Asp Val Ile Asn Leu Leu Pro Gly Ile Leu
    1880            1885            1890

Ser Pro Gly Ala Leu Val Val Gly Val Ile Cys Ala Ala Ile Leu
    1895            1900            1905

Arg Arg His Val Gly Pro Gly Glu Gly Ala Val Gln Trp Met Asn
    1910            1915            1920

Arg Leu Ile Ala Phe Ala Ser Arg Gly Asn His Val Ala Pro Thr
    1925            1930            1935

His Tyr Val Thr Glu Ser Asp Ala Ser Gln Arg Val Thr Gln Leu
    1940            1945            1950

Leu Gly Ser Leu Thr Ile Thr Ser Leu Leu Arg Arg Leu His Asn
    1955            1960            1965

Trp Ile Thr Glu Asp Cys Pro Ile Pro Cys Ser Gly Ser Trp Leu
    1970            1975            1980

Arg Asp Val Trp Asp Trp Val Cys Thr Ile Leu Thr Asp Phe Lys
    1985            1990            1995

Asn Trp Leu Thr Ser Lys Leu Phe Pro Lys Leu Pro Gly Leu Pro
    2000            2005            2010

Phe Ile Ser Cys Gln Lys Gly Tyr Lys Gly Val Trp Ala Gly Thr
    2015            2020            2025

Gly Ile Met Thr Thr Arg Cys Pro Cys Gly Ala Asn Ile Ser Gly
    2030            2035            2040

Asn Val Arg Leu Gly Ser Met Arg Ile Thr Gly Pro Lys Thr Cys
    2045            2050            2055

Met Asn Thr Trp Gln Gly Thr Phe Pro Ile Asn Cys Tyr Thr Glu
    2060            2065            2070

Gly Gln Cys Ala Pro Lys Pro Pro Thr Asn Tyr Lys Thr Ala Ile
    2075            2080            2085

Trp Arg Val Ala Ala Ser Glu Tyr Ala Glu Val Thr Gln His Gly
    2090            2095            2100

Ser Tyr Ser Tyr Val Thr Gly Leu Thr Thr Asp Asn Leu Lys Ile
    2105            2110            2115

Pro Cys Gln Leu Pro Ser Pro Glu Phe Phe Ser Trp Val Asp Gly
    2120            2125            2130

Val Gln Ile His Arg Phe Ala Pro Thr Pro Lys Pro Phe Phe Arg
    2135            2140            2145

Asp Glu Val Ser Phe Cys Val Gly Leu Asn Ser Tyr Ala Val Gly
    2150            2155            2160

Ser Gln Leu Pro Cys Glu Pro Glu Pro Asp Ala Asp Val Leu Arg
    2165            2170            2175

Ser Met Leu Thr Asp Pro Pro His Ile Thr Ala Glu Thr Ala Ala
    2180            2185            2190

Arg Arg Leu Ala Arg Gly Ser Pro Pro Ser Glu Ala Ser Ser Ser
    2195            2200            2205

Val Ser Gln Leu Ser Ala Pro Ser Leu Arg Ala Thr Cys Thr Thr
```

-continued

```
                    2210                2215                2220

His Ser Asn Thr Tyr Asp Val Asp Met Val Asp Ala Asn Leu Leu
    2225                2230                2235

Met Glu Gly Gly Val Ala Gln Thr Glu Pro Glu Ser Arg Val Pro
    2240                2245                2250

Val Leu Asp Phe Leu Glu Pro Met Ala Glu Glu Glu Ser Asp Leu
    2255                2260                2265

Glu Pro Ser Ile Pro Ser Glu Cys Met Leu Pro Arg Ser Gly Phe
    2270                2275                2280

Pro Arg Ala Leu Pro Ala Trp Ala Arg Pro Asp Tyr Asn Pro Pro
    2285                2290                2295

Leu Val Glu Ser Trp Arg Arg Pro Asp Tyr Gln Pro Pro Thr Val
    2300                2305                2310

Ala Gly Cys Ala Leu Pro Pro Lys Lys Ala Pro Thr Pro Pro
    2315                2320                2325

Pro Arg Arg Arg Arg Thr Val Gly Leu Ser Glu Ser Thr Ile Ser
    2330                2335                2340

Glu Ala Leu Gln Gln Leu Ala Ile Lys Thr Phe Gly Gln Pro Pro
    2345                2350                2355

Ser Ser Gly Asp Ala Gly Ser Ser Thr Gly Ala Gly Ala Ala Glu
    2360                2365                2370

Ser Gly Gly Pro Thr Ser Pro Gly Glu Pro Ala Pro Ser Glu Thr
    2375                2380                2385

Gly Ser Ala Ser Ser Met Pro Pro Leu Glu Gly Glu Pro Gly Asp
    2390                2395                2400

Pro Asp Leu Glu Ser Asp Gln Val Glu Leu Gln Pro Pro Pro Gln
    2405                2410                2415

Gly Gly Gly Val Ala Pro Gly Ser Gly Ser Gly Ser Trp Ser Thr
    2420                2425                2430

Cys Ser Glu Glu Asp Asp Thr Thr Val Cys Cys Ser Met Ser Tyr
    2435                2440                2445

Ser Trp Thr Gly Ala Leu Ile Thr Pro Cys Ser Pro Glu Glu Glu
    2450                2455                2460

Lys Leu Pro Ile Asn Pro Leu Ser Asn Ser Leu Leu Arg Tyr His
    2465                2470                2475

Asn Lys Val Tyr Cys Thr Thr Ser Lys Ser Ala Ser Gln Arg Ala
    2480                2485                2490

Lys Lys Val Thr Phe Asp Arg Thr Gln Val Leu Asp Ala His Tyr
    2495                2500                2505

Asp Ser Val Leu Lys Asp Ile Lys Leu Ala Ala Ser Lys Val Ser
    2510                2515                2520

Ala Arg Leu Leu Thr Leu Glu Glu Ala Cys Gln Leu Thr Pro Pro
    2525                2530                2535

His Ser Ala Arg Ser Lys Tyr Gly Phe Gly Ala Lys Glu Val Arg
    2540                2545                2550

Ser Leu Ser Gly Arg Ala Val Asn His Ile Lys Ser Val Trp Lys
    2555                2560                2565

Asp Leu Leu Glu Asp Pro Gln Thr Pro Ile Pro Thr Thr Ile Met
    2570                2575                2580

Ala Lys Asn Glu Val Phe Cys Val Asp Pro Ala Lys Gly Gly Lys
    2585                2590                2595

Lys Pro Ala Arg Leu Ile Val Tyr Pro Asp Leu Gly Val Arg Val
    2600                2605                2610
```

```
Cys Glu Lys Met Ala Leu Tyr Asp Ile Thr Gln Lys Leu Pro Gln
2615                2620                2625

Ala Val Met Gly Ala Ser Tyr Gly Phe Gln Tyr Ser Pro Ala Gln
2630                2635                2640

Arg Val Glu Tyr Leu Leu Lys Ala Trp Ala Glu Lys Lys Asp Pro
2645                2650                2655

Met Gly Phe Ser Tyr Asp Thr Arg Cys Phe Asp Ser Thr Val Thr
2660                2665                2670

Glu Arg Asp Ile Arg Thr Glu Glu Ser Ile Tyr Gln Ala Cys Ser
2675                2680                2685

Leu Pro Glu Glu Ala Arg Thr Ala Ile His Ser Leu Thr Glu Arg
2690                2695                2700

Leu Tyr Val Gly Gly Pro Met Phe Asn Ser Lys Gly Gln Thr Cys
2705                2710                2715

Gly Tyr Arg Arg Cys Arg Ala Ser Gly Val Leu Thr Thr Ser Met
2720                2725                2730

Gly Asn Thr Ile Thr Cys Tyr Val Lys Ala Leu Ala Ala Cys Lys
2735                2740                2745

Ala Ala Gly Ile Val Ala Pro Thr Met Leu Val Cys Gly Asp Asp
2750                2755                2760

Leu Val Val Ile Ser Glu Ser Gln Gly Thr Glu Glu Asp Glu Arg
2765                2770                2775

Asn Leu Arg Ala Phe Thr Glu Ala Met Thr Arg Tyr Ser Ala Pro
2780                2785                2790

Pro Gly Asp Pro Pro Arg Pro Glu Tyr Asp Leu Glu Leu Ile Thr
2795                2800                2805

Ser Cys Ser Ser Asn Val Ser Val Ala Leu Gly Pro Arg Gly Arg
2810                2815                2820

Arg Arg Tyr Tyr Leu Thr Arg Asp Pro Thr Thr Pro Leu Ala Arg
2825                2830                2835

Ala Ala Trp Glu Thr Val Arg His Ser Pro Ile Asn Ser Trp Leu
2840                2845                2850

Gly Asn Ile Ile Gln Tyr Ala Pro Thr Ile Trp Val Arg Met Val
2855                2860                2865

Leu Met Thr His Phe Phe Ser Ile Leu Met Val Gln Asp Thr Leu
2870                2875                2880

Asp Gln Asn Leu Asn Phe Glu Met Tyr Gly Ser Val Tyr Ser Val
2885                2890                2895

Asn Pro Leu Asp Leu Pro Ala Ile Ile Glu Arg Leu His Gly Leu
2900                2905                2910

Asp Ala Phe Ser Met His Thr Tyr Ser His His Glu Leu Thr Arg
2915                2920                2925

Val Ala Ser Ala Leu Arg Lys Leu Gly Ala Pro Pro Leu Arg Val
2930                2935                2940

Trp Lys Ser Arg Ala Arg Ala Val Arg Ala Ser Leu Ile Ser Arg
2945                2950                2955

Gly Gly Lys Ala Ala Val Cys Gly Arg Tyr Leu Phe Asn Trp Ala
2960                2965                2970

Val Lys Thr Lys Leu Lys Leu Thr Pro Leu Pro Glu Ala Arg Leu
2975                2980                2985

Leu Asp Leu Ser Ser Trp Phe Thr Val Gly Ala Gly Gly Gly Asp
2990                2995                3000

Ile Phe His Ser Val Ser Arg Ala Arg Pro Arg Ser Leu Leu Phe
3005                3010                3015
```

```
Gly Leu  Leu Leu Leu Phe Val  Gly Val Gly Leu Phe  Leu Leu Pro
    3020             3025                 3030

Ala Arg
    3035

<210> SEQ ID NO 5
<211> LENGTH: 9684
<212> TYPE: DNA
<213> ORGANISM: Hepatitis C virus

<400> SEQUENCE: 5
acctgcccct aatagggcg acactccgcc atgaatcact cccctgtgag gaactactgt      60
cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgccccg      240 caagactgct agccgagtag cgttggggttg cgaaaggcct tgtggtactg cctgataggg     300
tgcttgcgag tgccccggga ggtctcgtag accgtgcacc atgagcacac ttccaaaacc     360
ccaaagaaaa accaaagaa acaccaaccg tcgcccaatg acgtcaagt tcccgggtgg      420 cggtcagatc gttggcggag tttacttgtt gccgcgcagg ggccccccggt tgggtgtgcg     480 cgcgacgagg aagacttccg agcgatccca gcccagaggc aggcgccaac ctataccaaa     540
ggcgcgccag ccccagggca ggcactgggc tcagcccgga tatccttggc cctttatgg      600 gaacgagggc tgtgggtggg caggttggct cctgtccccc cgcggctccc ggccacactg     660 ggccccaac gaccccggc gtcgatccg gaatttgggt aaggtcatcg atcccctaac      720
gtgtgggttc gccgatctca tggggtacat tccgtcgtg ggcgcgcctt ggcggcgt      780 cgcggctgca ctcgcacatg gtgtgagggc aatcgaggac gggatcaatt atgcaacagg     840
gaatcttccc ggttgctctt tctctatctt cctcttggca ctactctcgt gcctcacaac     900
gccagcgtcg gctcttacct acggtaactc cagtgggcta taccatctta caatgattg      960 ccccaactcc agcatcgtgc tggaggcgga tgccatgatc ttgcatttgc ctggatgctt    1020
gccttgtgtg agggtcaata caaccagtc catctgttgg catgctgtgt cccccaccct    1080
agccatacca aatgcttcca cacctgcaac gggattccgt aggcatgtgg accttcttgc    1140
gggcgccgca gtggtttgct catccctgta catcgggat ctgtgcggct ccctcttttt    1200
ggcagggcaa ctatttacct ttcagccccg ccgtcactgg actgtgcaag actgcaactg    1260
ctccatttat acaggccacg tcaccggcca caggatggct tgggacatga tgatgaattg    1320
gtcacccaca accactctgg tcctatctag tatcttgagg gtacctgaga tctgtgcgag    1380
tgtgatattt ggtggccatt ggggatact actagccgtt gcctactttg gtatggctgg    1440
caactggcta aaagtctggg ctgtcctgtt cttatttgca gggttgaag caaccaccac    1500 catcggccat caagtaggcc gcactactgg tggcttagcc agtctcttct ccatcggtcc    1560
caggcaaaat ctacaactca tcaacaccac tggcagctgg catataaaca ggactgctct    1620
gaactgcaat gattccctcc agacgggtt cataacgtca ctctttttatg ccaagaacgt    1680 caactcctcg ggctgcccag agcggatggc tgcgtgtaag cccctcgcgg acttccggca    1740
ggggtggggc caaataaccct acaaagtcaa catctcgggc cctccgacg accgtccta    1800 ctgttggcat tacgctccca ggccatgtga cgtggtgtcg gccgcacgg tgtgcggccc    1860 cgtttactgc ttcacgccca gccctgtcgt agtaggaacc actgacaagc tgggcattcc    1920
cacatacaac tggggggaga atgagacgga tgtgttcatg ttggaaagcc tcggcctcc    1980
```

```
tactggagga tggtttgggt gcacgtggat gaactctacg ggctttacca agacctgtgg    2040
tgccccgcca tgtcagatag tcccgggaga ttacaatagc tctgccaatg agcttttgtg    2100
ccccaccgac tgcttccgta aacatccgga agctacatat cagcggtgtg gatcgggacc    2160
ctggatcaca cctaggtgtc tggtggatta cccctacagg ctgtggcact accoctgtac    2220 tgtcaacttc accttgcata aagtcaggat gttcgtggga ggcattgagc atcggtttga    2280
cgccgcatgt aactggacca gaggcgagcg gtgtgatcta catgacagag acaggattga    2340
aatgagcccg ctgcttttct caactacgca gcttgccata cttccctgtt cattttccac    2400
catgccggcc ttgtcaaccg gcctcatcca cctgcatcag aacatagtgg acgtgcagta    2460
cctctacgga gtctcctcga gcgttacctc gtgggtggtg aagtgggagt acattgttct    2520
ggtgttcctg gttctggcag atgctcggat ttgtacatgt ctctggttaa tgctgctcat    2580
aaccaacgtt gaagcagcag tggaaaggct tgtcgtcctc aatgcggcta gcgccgccgg    2640
caccgccggc tggtggtggg cggtgctctt cctgtgctgt gcttggtacg tgaaaggccg    2700
ccttgtgcct gcgtgtacct acatggcact gggaatgtgg ccgttgctcc tgacaatctt    2760
ggccctgcct cgccgagcat acgctatgga caatgagcaa gcggcatccc tcggagctgt    2820
tggtctcttg gtgctcacca tctttaccat cacccccatg tacaagaagc tgttgacctg    2880
ctccatttgg tggaatcagt atttcctcgc ccgagctgag gccatgatac acgagtgggt    2940
gcccgaccta cgggttaggg gcggtaggga ctccatcatc ttacttacct gcttgttaca    3000
tccacagctg gggtttgagg tcaccaaaat tctactagcc atcctggccc ctctatacat    3060
cctgcagtac agtttgctca aggtgcctta cttttgtgcgc gcccacgtac tcctgcgtgc    3120
ttgcctgctt gttcgtaggc tagcaggggg taagtacgtg caggcgtgcc ttctgaggtt    3180
gggcgcttgg actggcacct ttgtctatga ccatctcgcc cctctctctg actgggctag    3240
cgacggactg cgcgatttgg cagtcgcaat cgagccggtc atttctctc ccatggagaa    3300 gaaaatcatt acctggggtg cggataccgc cgcgtgtggt gacatcttga gtggcctccc    3360
ggtgtcagcg aggttgggga atttggtgct actgggaccc gcggacgata tgcagcgcgg    3420
gggttggaag ctttttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gaggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840 gaagggtgtcc tcggggggc cggtgctctg ccctagggc cacgtcgttg gctcttccg    3900 agcagctgtg tgctctcggg gcgtggccaa atccatcgat ttcatcccg ttgagacact    3960 cgacgttgtt acaaggtctc ccactttcag tgacaacagc acgccaccgg ctgtgccca    4020 gacctatcag gtcgggtact tgcatgctcc aactggcagt ggaaagagca caaggtcc    4080 tgtcgcgtat gccgcccagg ggtacaaagt actagtgctt aaccctcgg tagctgccac    4140 cctggggttt ggggcgtacc tatccaaggc acatggcatc aatcccaaca ttaggactgg    4200
agtcaggacc gtgatgaccg gggaggccat cacgtactcc acatatggca aatttctcgc    4260 cgatggggc tgcgctagcg gcgcctatga catcatcata tgcgatgaat gccacgctgt    4320
ggatgctacc tccattctcg gcatcggaac ggtccttgat caagcagaga cagccgggt    4380
```

```
cagactaact gtgctggcta cggccacacc ccccgggtca gtgacaaccc cccatcccga   4440
tatagaagag gtaggcctcg ggcgggaggg tgagatcccc ttctatggga gggcgattcc   4500
cctatcctgc atcaagggag ggagacacct gattttctgc cactcaaaga aaaagtgtga   4560
cgagctcgcg gcggcccttc ggggcatggg cttgaatgcc gtggcatact atagagggtt   4620
ggacgtctcc ataataccag ctcagggaga tgtggtggtc gtcgccaccg acgccctcat   4680
gacggggtac actggagact tgactccgt gatcgactgc aatgtagcgg tcacccaagc    4740
tgtcgacttc agcctggacc ccaccttcac tataaccaca cagactgtcc cacaagacgc   4800
tgtctcacgc agtcagcgcc gcgggcgcac aggtagagga agacagggca cttataggta   4860
tgtttccact ggtgaacgag cctcaggaat gtttgacagt gtagtgcttt gtgagtgcta   4920
cgacgcaggg gctgcgtggt acgatctcac accagcggag accaccgtca ggcttagagc   4980
gtatttcaac acgccggcc tacccgtgtg tcaagaccat cttgaatttt gggaggcagt     5040
tttcaccggc ctcacacaca tagacgccca cttcctctcc caaacaaagc aagcggggga   5100
gaacttcgcg tacctagtag cctaccaagc tacggtgtgc gccagagcca aggcccctcc   5160
cccgtcctgg gacgccatgt ggaagtgcct ggcccgactc aagcctacgc ttgcgggccc   5220
cacacctctc ctgtaccgtt tgggccctat taccaatgag gtcaccctca cacaccctgg   5280
gacgaagtac atcgccacat gcatgcaagc tgaccttgag gtcatgacca gcacgtgggt   5340
cctagctgga ggagtcctgg cagccgtcgc cgcatattgc ctggcgactg gatgcgtttc   5400
catcatcggc cgcttgcacg tcaaccagcg agtcgtcgtt gcgccggata aggaggtcct   5460
gtatgaggct tttgatgaga tggaggaatg cgcctctagg gcggctctca tcgaagaggg   5520
gcagcggata gccgagatgt tgaagtccaa gatccaaggc ttgctgcagc aggcctctaa   5580
gcaggcccag gacatacaac ccgctatgca ggcttcatgg cccaaagtgg aacaattttg   5640
ggccagacac atgtggaact tcattagcgg catccaatac ctcgcaggat tgtcaacact   5700
gccagggaac cccgcggtgg cttccatgat ggcattcagt gccgccctca ccagtccgtt   5760
gtcgaccagt accaccatcc ttctcaacat catgggaggc tggttagcgt cccagatcgc   5820 accaccgcg ggggccaccg gctttgtcgt cagtggcctg gtggggggctg ccgtgggcag    5880 cataggcctg ggtaaggtgc tggtggacat cctggcagga tatggtgcgg gcatttcggg   5940
ggccctcgtc gcattcaaga tcatgtctgg cgagaagccc tctatggaag atgtcatcaa   6000
tctactgcct gggatcctgt ctccgggagc cctggtggtg ggggtcatct gcgcggccat   6060
tctgcgccgc cacgtgggac cggggagg cgcggtccaa tggatgaaca ggcttattgc     6120
ctttgcttcc agaggaaacc acgtcgcccc tactcactac gtgacggagt cggatgcgtc   6180
gcagcgtgtg acccaactac ttggctctct tactataacc agcctactca gaagactcca   6240
caattggata actgaggact gccccatccc atgctccgga tcctggctcc gcgacgtgtg   6300
ggactgggtt tgcaccatct tgacagactt caaaaattgg ctgacctcta aattgttccc   6360
caagctgccc ggcctccct tcatctcttg tcaaagggg tacaagggtg tgtgggccgg    6420
cactggcatc atgaccacgc gctgcccttg cggcgccaac atctctggca atgtccgcct   6480
gggctctatg aggatcacag ggcctaaaac ctgcatgaac acctggcagg gacctttcc    6540 tatcaattgc tacacggagg gccagtgcgc gccgaaaccc cccacgaact acaagaccgc   6600
catctggagg gtggcggcct cggagtacgc ggaggtgacg cagcatgggt cgtactccta   6660
tgtaacagga ctgaccactg acaatctgaa aattccttgc caactacctt ctccagagtt   6720
tttctcctgg gtggacggtg tgcagatcca taggtttgca cccacaccaa agccgttttt   6780
```

```
ccgggatgag gtctcgttct gcgttgggct taattcctat gctgtcgggt cccagcttcc   6840
ctgtgaacct gagcccgacg cagacgtatt gaggtccatg ctaacagatc cgccccacat   6900
cacggcggag actgcggcgc ggcgcttggc acggggatca cctccatctg aggcgagctc   6960
ctcagtgagc cagctatcag caccgtcgct gcgggccacc tgcaccaccc acagcaacac   7020
ctatgacgtg gacatggtcg atgccaacct gctcatggag ggcggtgtgg ctcagacaga   7080
gcctgagtcc agggtgcccg ttctggactt tctcgagcca atggccgagg aagagagcga   7140
ccttgagccc tcaataccat cggagtgcat gctccccagg agcgggtttc cacgggcctt   7200
accggcttgg gcacggcctg actacaaccc gccgctcgtg gaatcgtgga ggaggccaga   7260
ttaccaaccg cccaccgttg ctggttgtgc tctccccccc cccaagaagg ccccgacgcc   7320
tcccccaagg agacgccgga cagtgggtct gagcgagagc accatatcag aagccctcca   7380
gcaactggcc atcaagacct ttggccagcc ccctcgagc ggtgatgcag gctcgtccac   7440
gggggcgggc gccgccgaat ccggcggtcc gacgtcccct ggtgagccgg ccccctcaga   7500
gacaggttcc gcctcctcta tgcccccct cgaggggag cctggagatc cggacctgga   7560
gtctgatcag gtagagcttc aacctccccc caggggggg ggggtagctc ccggttcggg   7620
ctcggggtct tggtctactt gctccgagga ggacgatacc accgtgtgct gctccatgtc   7680
atactcctgg accggggctc taataactcc ctgtagcccc gaagaggaaa agttgccaat   7740
caaccctttg agtaactcgc tgttgcgata ccataacaag gtgtactgta caacatcaaa   7800
gagcgcctca cagagggcta aaaaggtaac ttttgacagg acgcaagtgc tcgacgccca   7860
ttatgactca gtcttaaagg acatcaagct agcggcttcc aaggtcagcg caaggctcct   7920 cacccttggag gaggcgtgcc agttgactcc accccattct gcaagatcca agtatggatt   7980
cggggccaag gaggtccgca gcttgtccgg gagggccgtt aaccacatca gtccgtgtg   8040 gaaggacctc ctggaagacc cacaaacacc aattcccaca accatcatgg ccaaaaatga   8100
ggtgttctgc gtggaccccg ccaagggggg taagaaacca gctcgcctca tcgtttaccc   8160
tgacctcggc gtccgggtct gcgagaaaat ggccctctat gacattacac aaaagcttcc   8220
tcaggcggta atgggagctt cctatggctt ccagtactcc cctgcccaac gggtggagta   8280
tctcttgaaa gcatgggcgg aaaagaagga ccccatgggt ttttcgtatg atacccgatg   8340
cttcgactca accgtcactg agagagacat caggaccgag gagtccatat accaggcctg   8400
ctccctgccc gaggaggccc gcactgccat acactcgctg actgagagac tttacgtagg   8460
agggcccatg ttcaacagca agggtcaaac ctgcggttac agacgttgcc gcgccagcgg   8520
ggtgctaacc actagcatgg gtaacaccat cacatgctat gtgaaagccc tagcggcctg   8580
caaggctgcg gggatagttg cgcccacaat gctggtatgc ggcgatgacc tagtagtcat   8640
ctcagaaagc cagggggactg aggaggacga gcggaacctg agagccttca cggaggccat   8700
gaccaggtac tctgcccctc ctggtgatcc ccccagaccg gaatatgacc tggagctaat   8760
aacatcctgt tcctcaaatg tgtctgtggc gttgggcccg cggggccgcc gcagatacta   8820
cctgaccaga gacccaacca ctccactcgc ccgggctgcc tgggaaacag ttagacactc   8880
ccctatcaat tcatggctgg aaacatcat ccagtatgct ccaaccatat gggttcgcat   8940
ggtcctaatg acacacttct tctccattct catggtccaa gacaccctgg accagaacct   9000
caactttgag atgtatggat cagtatactc cgtgaatcct ttggaccttc agccataat   9060 tgagaggtta cacgggcttg acgccttttc tatgcacaca tactctcacc acgaactgac   9120
gcgggtggct tcagccctca gaaaacttgg ggcgccaccc ctcagggtgt ggaagagtcg   9180
```

-continued

```
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttcacag     9360 cgtgtcgcgc gcccgacccc gctcattact cttcggccta ctcctacttt tcgtaggggt    9420
aggcctcttc ctactcccg ctcggtagag cggcacacac taggtacact ccatagctaa     9480
ctgttccttt tttttttttt tttttttttt tttttttttt tttttttttt ctttttttt     9540 ttttccctc tttcttccct tctcatctta ttctactttc tttcttggtg gctccatctt     9600
agccctagtc acggctagct gtgaaaggtc cgtgagccgc atgactgcag agagtgccgt    9660
aactggtctc tctgcagatc atgt                                           9684
```

<210> SEQ ID NO 6
<211> LENGTH: 3035
<212> TYPE: PRT
<213> ORGANISM: Hepatitis C virus

<400> SEQUENCE: 6

```
Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
        195                 200                 205

Asn Ser Ser Ile Val Leu Glu Ala Asp Ala Met Ile Leu His Leu Pro
    210                 215                 220

Gly Cys Leu Pro Cys Val Arg Val Asn Asn Gln Ser Ile Cys Trp
225                 230                 235                 240

His Ala Val Ser Pro Thr Leu Ala Ile Pro Asn Ala Ser Thr Pro Ala
                245                 250                 255

Thr Gly Phe Arg Arg His Val Asp Leu Leu Ala Gly Ala Ala Val Val
            260                 265                 270

Cys Ser Ser Leu Tyr Ile Gly Asp Leu Cys Gly Ser Leu Phe Leu Ala
        275                 280                 285
```

-continued

```
Gly Gln Leu Phe Thr Phe Gln Pro Arg Arg His Trp Thr Val Gln Asp
        290                 295                 300
Cys Asn Cys Ser Ile Tyr Thr Gly His Val Thr Gly His Arg Met Ala
305                 310                 315                 320
Trp Asp Met Met Met Asn Trp Ser Pro Thr Thr Thr Leu Val Leu Ser
                    325                 330                 335
Ser Ile Leu Arg Val Pro Glu Ile Cys Ala Ser Val Ile Phe Gly Gly
            340                 345                 350
His Trp Gly Ile Leu Leu Ala Val Ala Tyr Phe Gly Met Ala Gly Asn
        355                 360                 365
Trp Leu Lys Val Leu Ala Val Leu Phe Leu Phe Ala Gly Val Glu Ala
        370                 375                 380
Thr Thr Thr Ile Gly His Gln Val Gly Arg Thr Thr Gly Gly Leu Ala
385                 390                 395                 400
Ser Leu Phe Ser Ile Gly Pro Arg Gln Asn Leu Gln Leu Ile Asn Thr
            405                 410                 415
Thr Gly Ser Trp His Ile Asn Arg Thr Ala Leu Asn Cys Asn Asp Ser
        420                 425                 430
Leu Gln Thr Gly Phe Ile Thr Ser Leu Phe Tyr Ala Lys Asn Val Asn
        435                 440                 445
Ser Ser Gly Cys Pro Glu Arg Met Ala Ala Cys Lys Pro Leu Ala Asp
450                 455                 460
Phe Arg Gln Gly Trp Gly Gln Ile Thr Tyr Lys Val Asn Ile Ser Gly
465                 470                 475                 480
Pro Ser Asp Asp Arg Pro Tyr Cys Trp His Tyr Ala Pro Arg Pro Cys
                    485                 490                 495
Asp Val Val Ser Ala Arg Thr Val Cys Gly Pro Val Tyr Cys Phe Thr
                500                 505                 510
Pro Ser Pro Val Val Val Gly Thr Thr Asp Lys Leu Gly Ile Pro Thr
            515                 520                 525
Tyr Asn Trp Gly Glu Asn Glu Thr Asp Val Phe Met Leu Glu Ser Leu
        530                 535                 540
Arg Pro Pro Thr Gly Gly Trp Phe Gly Cys Thr Trp Met Asn Ser Thr
545                 550                 555                 560
Gly Phe Thr Lys Thr Cys Gly Ala Pro Pro Cys Gln Ile Val Pro Gly
                565                 570                 575
Asp Tyr Asn Ser Ser Ala Asn Glu Leu Leu Cys Pro Thr Asp Cys Phe
                580                 585                 590
Arg Lys His Pro Glu Ala Thr Tyr Gln Arg Cys Gly Ser Gly Pro Trp
            595                 600                 605
Ile Thr Pro Arg Cys Leu Val Asp Tyr Pro Tyr Arg Leu Trp His Tyr
        610                 615                 620
Pro Cys Thr Val Asn Phe Thr Leu His Lys Val Arg Met Phe Val Gly
625                 630                 635                 640
Gly Ile Glu His Arg Phe Asp Ala Ala Cys Asn Trp Thr Arg Gly Glu
                645                 650                 655
Arg Cys Asp Leu His Asp Arg Asp Arg Ile Glu Met Ser Pro Leu Leu
                660                 665                 670
Phe Ser Thr Thr Gln Leu Ala Ile Leu Pro Cys Ser Phe Ser Thr Met
            675                 680                 685
Pro Ala Leu Ser Thr Gly Leu Ile His Leu His Gln Asn Ile Val Asp
        690                 695                 700
Val Gln Tyr Leu Tyr Gly Val Ser Ser Ser Val Thr Ser Trp Val Val
```

-continued

```
            705                 710                 715                 720
Lys Trp Glu Tyr Ile Val Leu Val Phe Leu Val Leu Ala Asp Ala Arg
                    725                 730                 735
Ile Cys Thr Cys Leu Trp Leu Met Leu Leu Ile Thr Asn Val Glu Ala
                740                 745                 750
Ala Val Glu Arg Leu Val Val Leu Asn Ala Ala Ser Ala Ala Gly Thr
            755                 760                 765
Ala Gly Trp Trp Trp Ala Val Leu Phe Leu Cys Cys Ala Trp Tyr Val
        770                 775                 780
Lys Gly Arg Leu Val Pro Ala Cys Thr Tyr Met Ala Leu Gly Met Trp
785                 790                 795                 800
Pro Leu Leu Leu Thr Ile Leu Ala Leu Pro Arg Arg Ala Tyr Ala Met
                    805                 810                 815
Asp Asn Glu Gln Ala Ala Ser Leu Gly Ala Val Gly Leu Leu Val Leu
                820                 825                 830
Thr Ile Phe Thr Ile Thr Pro Met Tyr Lys Lys Leu Leu Thr Cys Ser
            835                 840                 845
Ile Trp Trp Asn Gln Tyr Phe Leu Ala Arg Ala Glu Ala Met Ile His
        850                 855                 860
Glu Trp Val Pro Asp Leu Arg Val Arg Gly Gly Arg Asp Ser Ile Ile
865                 870                 875                 880
Leu Leu Thr Cys Leu Leu His Pro Gln Leu Gly Phe Glu Val Thr Lys
                    885                 890                 895
Ile Leu Leu Ala Ile Leu Ala Pro Leu Tyr Ile Leu Gln Tyr Ser Leu
                900                 905                 910
Leu Lys Val Pro Tyr Phe Val Arg Ala His Val Leu Leu Arg Ala Cys
            915                 920                 925
Leu Leu Val Arg Arg Leu Ala Gly Gly Lys Tyr Val Gln Ala Cys Leu
        930                 935                 940
Leu Arg Leu Gly Ala Trp Thr Gly Thr Phe Val Tyr Asp His Leu Ala
945                 950                 955                 960
Pro Leu Ser Asp Trp Ala Ser Asp Gly Leu Arg Asp Leu Ala Val Ala
                    965                 970                 975
Ile Glu Pro Val Ile Phe Ser Pro Met Glu Lys Lys Ile Ile Thr Trp
                980                 985                 990
Gly Ala Asp Thr Ala Ala Cys Gly Asp Ile Leu Ser Gly Leu Pro Val
            995                 1000                1005
Ser Ala Arg Leu Gly Asn Leu Val Leu Leu Gly Pro Ala Asp Asp
        1010                1015                1020
Met Gln Arg Gly Gly Trp Lys Leu Leu Ala Pro Ile Thr Ala Tyr
        1025                1030                1035
Ala Gln Gln Thr Arg Gly Leu Leu Gly Ala Ile Val Val Ser Met
        1040                1045                1050
Thr Gly Arg Asp Arg Thr Glu Gln Ala Gly Glu Val Gln Ile Leu
        1055                1060                1065
Ser Thr Val Ser Gln Ser Phe Leu Gly Thr Thr Ile Ser Gly Val
        1070                1075                1080
Leu Trp Thr Val Tyr His Gly Ala Gly Asn Lys Thr Leu Ala Gly
        1085                1090                1095
Leu Arg Gly Pro Val Thr Gln Met Tyr Ser Ser Ala Glu Gly Asp
        1100                1105                1110
Leu Val Gly Trp Pro Ser Pro Pro Gly Thr Lys Ser Leu Glu Pro
        1115                1120                1125
```

-continued

Cys Lys Cys Gly Ala Val Asp Leu Tyr Leu Val Thr Arg Asn Ala
1130                    1135                1140

Asp Val Ile Pro Ala Arg Arg Gly Asp Lys Arg Gly Ala Leu
1145                1150                1155

Leu Ser Pro Arg Pro Ile Ser Thr Leu Lys Gly Ser Ser Gly Gly
1160                    1165                1170

Pro Val Leu Cys Pro Arg Gly His Val Gly Leu Phe Arg Ala
1175                1180                1185

Ala Val Cys Ser Arg Gly Val Ala Lys Ser Ile Asp Phe Ile Pro
1190                    1195                1200

Val Glu Thr Leu Asp Val Val Thr Arg Ser Pro Thr Phe Ser Asp
1205                    1210                1215

Asn Ser Thr Pro Pro Ala Val Pro Gln Thr Tyr Gln Val Gly Tyr
1220                    1225                1230

Leu His Ala Pro Thr Gly Ser Gly Lys Ser Thr Lys Val Pro Val
1235                    1240                1245

Ala Tyr Ala Ala Gln Gly Tyr Lys Val Leu Val Leu Asn Pro Ser
1250                    1255                1260

Val Ala Ala Thr Leu Gly Phe Gly Ala Tyr Leu Ser Lys Ala His
1265                    1270                1275

Gly Ile Asn Pro Asn Ile Arg Thr Gly Val Arg Thr Val Met Thr
1280                    1285                1290

Gly Glu Ala Ile Thr Tyr Ser Thr Tyr Gly Lys Phe Leu Ala Asp
1295                    1300                1305

Gly Gly Cys Ala Ser Gly Ala Tyr Asp Ile Ile Ile Cys Asp Glu
1310                    1315                1320

Cys His Ala Val Asp Ala Thr Ser Ile Leu Gly Ile Gly Thr Val
1325                    1330                1335

Leu Asp Gln Ala Glu Thr Ala Gly Val Arg Leu Thr Val Leu Ala
1340                    1345                1350

Thr Ala Thr Pro Pro Gly Ser Val Thr Thr Pro His Pro Asp Ile
1355                    1360                1365

Glu Glu Val Gly Leu Gly Arg Glu Gly Glu Ile Pro Phe Tyr Gly
1370                    1375                1380

Arg Ala Ile Pro Leu Ser Cys Ile Lys Gly Gly Arg His Leu Ile
1385                    1390                1395

Phe Cys His Ser Lys Lys Lys Cys Asp Glu Leu Ala Ala Ala Leu
1400                    1405                1410

Arg Gly Met Gly Leu Asn Ala Val Ala Tyr Tyr Arg Gly Leu Asp
1415                    1420                1425

Val Ser Ile Ile Pro Ala Gln Gly Asp Val Val Val Ala Thr
1430                    1435                1440

Asp Ala Leu Met Thr Gly Tyr Thr Gly Asp Phe Asp Ser Val Ile
1445                    1450                1455

Asp Cys Asn Val Ala Val Thr Gln Ala Val Asp Phe Ser Leu Asp
1460                    1465                1470

Pro Thr Phe Thr Ile Thr Thr Gln Thr Val Pro Gln Asp Ala Val
1475                    1480                1485

Ser Arg Ser Gln Arg Arg Gly Arg Thr Gly Arg Gly Arg Gln Gly
1490                    1495                1500

Thr Tyr Arg Tyr Val Ser Thr Gly Glu Arg Ala Ser Gly Met Phe
1505                    1510                1515

Asp Ser Val Val Leu Cys Glu Cys Tyr Asp Ala Gly Ala Ala Trp
1520                    1525                1530

```
Tyr Asp Leu Thr Pro Ala Glu Thr Thr Val Arg Leu Arg Ala Tyr
    1535                1540                1545

Phe Asn Thr Pro Gly Leu Pro Val Cys Gln Asp His Leu Glu Phe
    1550                1555                1560

Trp Glu Ala Val Phe Thr Gly Leu Thr His Ile Asp Ala His Phe
    1565                1570                1575

Leu Ser Gln Thr Lys Gln Ala Gly Glu Asn Phe Ala Tyr Leu Val
    1580                1585                1590

Ala Tyr Gln Ala Thr Val Cys Ala Arg Ala Lys Ala Pro Pro Pro
    1595                1600                1605

Ser Trp Asp Ala Met Trp Lys Cys Leu Ala Arg Leu Lys Pro Thr
    1610                1615                1620

Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680

Gly Cys Val Ser Ile Ile Gly Arg Leu His Val Asn Gln Arg Val
    1685                1690                1695

Val Val Ala Pro Asp Lys Glu Val Leu Tyr Glu Ala Phe Asp Glu
    1700                1705                1710

Met Glu Glu Cys Ala Ser Arg Ala Ala Leu Ile Glu Glu Gly Gln
    1715                1720                1725

Arg Ile Ala Glu Met Leu Lys Ser Lys Ile Gln Gly Leu Leu Gln
    1730                1735                1740

Gln Ala Ser Lys Gln Ala Gln Asp Ile Gln Pro Ala Met Gln Ala
    1745                1750                1755

Ser Trp Pro Lys Val Glu Gln Phe Trp Ala Arg His Met Trp Asn
    1760                1765                1770

Phe Ile Ser Gly Ile Gln Tyr Leu Ala Gly Leu Ser Thr Leu Pro
    1775                1780                1785

Gly Asn Pro Ala Val Ala Ser Met Met Ala Phe Ser Ala Ala Leu
    1790                1795                1800

Thr Ser Pro Leu Ser Thr Ser Thr Thr Ile Leu Leu Asn Ile Met
    1805                1810                1815

Gly Gly Trp Leu Ala Ser Gln Ile Ala Pro Pro Ala Gly Ala Thr
    1820                1825                1830

Gly Phe Val Val Ser Gly Leu Val Gly Ala Ala Val Gly Ser Ile
    1835                1840                1845

Gly Leu Gly Lys Val Leu Val Asp Ile Leu Ala Gly Tyr Gly Ala
    1850                1855                1860

Gly Ile Ser Gly Ala Leu Val Ala Phe Lys Ile Met Ser Gly Glu
    1865                1870                1875

Lys Pro Ser Met Glu Asp Val Ile Asn Leu Leu Pro Gly Ile Leu
    1880                1885                1890

Ser Pro Gly Ala Leu Val Val Gly Val Ile Cys Ala Ala Ile Leu
    1895                1900                1905

Arg Arg His Val Gly Pro Gly Glu Gly Ala Val Gln Trp Met Asn
    1910                1915                1920

Arg Leu Ile Ala Phe Ala Ser Arg Gly Asn His Val Ala Pro Thr
```

-continued

```
            1925                1930                1935

His Tyr Val Thr Glu Ser Asp Ala Ser Gln Arg Val Thr Gln Leu
    1940                1945                1950

Leu Gly Ser Leu Thr Ile Thr Ser Leu Leu Arg Arg Leu His Asn
    1955                1960                1965

Trp Ile Thr Glu Asp Cys Pro Ile Pro Cys Ser Gly Ser Trp Leu
    1970                1975                1980

Arg Asp Val Trp Asp Trp Val Cys Thr Ile Leu Thr Asp Phe Lys
    1985                1990                1995

Asn Trp Leu Thr Ser Lys Leu Phe Pro Lys Leu Pro Gly Leu Pro
    2000                2005                2010

Phe Ile Ser Cys Gln Lys Gly Tyr Lys Gly Val Trp Ala Gly Thr
    2015                2020                2025

Gly Ile Met Thr Thr Arg Cys Pro Cys Gly Ala Asn Ile Ser Gly
    2030                2035                2040

Asn Val Arg Leu Gly Ser Met Arg Ile Thr Gly Pro Lys Thr Cys
    2045                2050                2055

Met Asn Thr Trp Gln Gly Thr Phe Pro Ile Asn Cys Tyr Thr Glu
    2060                2065                2070

Gly Gln Cys Ala Pro Lys Pro Pro Thr Asn Tyr Lys Thr Ala Ile
    2075                2080                2085

Trp Arg Val Ala Ala Ser Glu Tyr Ala Glu Val Thr Gln His Gly
    2090                2095                2100

Ser Tyr Ser Tyr Val Thr Gly Leu Thr Thr Asp Asn Leu Lys Ile
    2105                2110                2115

Pro Cys Gln Leu Pro Ser Pro Glu Phe Phe Ser Trp Val Asp Gly
    2120                2125                2130

Val Gln Ile His Arg Phe Ala Pro Thr Pro Lys Pro Phe Phe Arg
    2135                2140                2145

Asp Glu Val Ser Phe Cys Val Gly Leu Asn Ser Tyr Ala Val Gly
    2150                2155                2160

Ser Gln Leu Pro Cys Glu Pro Glu Pro Asp Ala Asp Val Leu Arg
    2165                2170                2175

Ser Met Leu Thr Asp Pro Pro His Ile Thr Ala Glu Thr Ala Ala
    2180                2185                2190

Arg Arg Leu Ala Arg Gly Ser Pro Pro Ser Glu Ala Ser Ser Ser
    2195                2200                2205

Val Ser Gln Leu Ser Ala Pro Ser Leu Arg Ala Thr Cys Thr Thr
    2210                2215                2220

His Ser Asn Thr Tyr Asp Val Asp Met Val Asp Ala Asn Leu Leu
    2225                2230                2235

Met Glu Gly Gly Val Ala Gln Thr Glu Pro Glu Ser Arg Val Pro
    2240                2245                2250

Val Leu Asp Phe Leu Glu Pro Met Ala Glu Glu Ser Asp Leu
    2255                2260                2265

Glu Pro Ser Ile Pro Ser Glu Cys Met Leu Pro Arg Ser Gly Phe
    2270                2275                2280

Pro Arg Ala Leu Pro Ala Trp Ala Arg Pro Asp Tyr Asn Pro Pro
    2285                2290                2295

Leu Val Glu Ser Trp Arg Arg Pro Asp Tyr Gln Pro Pro Thr Val
    2300                2305                2310

Ala Gly Cys Ala Leu Pro Pro Pro Lys Lys Ala Pro Thr Pro Pro
    2315                2320                2325
```

-continued

Pro Arg Arg Arg Arg Thr Val Gly Leu Ser Glu Ser Thr Ile Ser
2330                    2335                2340

Glu Ala Leu Gln Gln Leu Ala Ile Lys Thr Phe Gly Gln Pro Pro
2345                    2350                2355

Ser Ser Gly Asp Ala Gly Ser Ser Thr Gly Ala Gly Ala Ala Glu
2360                    2365                2370

Ser Gly Gly Pro Thr Ser Pro Gly Glu Pro Ala Pro Ser Glu Thr
2375                    2380                2385

Gly Ser Ala Ser Ser Met Pro Pro Leu Glu Gly Glu Pro Gly Asp
2390                    2395                2400

Pro Asp Leu Glu Ser Asp Gln Val Glu Leu Gln Pro Pro Pro Gln
2405                    2410                2415

Gly Gly Gly Val Ala Pro Gly Ser Gly Ser Gly Ser Trp Ser Thr
2420                    2425                2430

Cys Ser Glu Glu Asp Asp Thr Thr Val Cys Cys Ser Met Ser Tyr
2435                    2440                2445

Ser Trp Thr Gly Ala Leu Ile Thr Pro Cys Ser Pro Glu Glu Glu
2450                    2455                2460

Lys Leu Pro Ile Asn Pro Leu Ser Asn Ser Leu Leu Arg Tyr His
2465                    2470                2475

Asn Lys Val Tyr Cys Thr Thr Ser Lys Ser Ala Ser Gln Arg Ala
2480                    2485                2490

Lys Lys Val Thr Phe Asp Arg Thr Gln Val Leu Asp Ala His Tyr
2495                    2500                2505

Asp Ser Val Leu Lys Asp Ile Lys Leu Ala Ala Ser Lys Val Ser
2510                    2515                2520

Ala Arg Leu Leu Thr Leu Glu Glu Ala Cys Gln Leu Thr Pro Pro
2525                    2530                2535

His Ser Ala Arg Ser Lys Tyr Gly Phe Gly Ala Lys Glu Val Arg
2540                    2545                2550

Ser Leu Ser Gly Arg Ala Val Asn His Ile Lys Ser Val Trp Lys
2555                    2560                2565

Asp Leu Leu Glu Asp Pro Gln Thr Pro Ile Pro Thr Thr Ile Met
2570                    2575                2580

Ala Lys Asn Glu Val Phe Cys Val Asp Pro Ala Lys Gly Gly Lys
2585                    2590                2595

Lys Pro Ala Arg Leu Ile Val Tyr Pro Asp Leu Gly Val Arg Val
2600                    2605                2610

Cys Glu Lys Met Ala Leu Tyr Asp Ile Thr Gln Lys Leu Pro Gln
2615                    2620                2625

Ala Val Met Gly Ala Ser Tyr Gly Phe Gln Tyr Ser Pro Ala Gln
2630                    2635                2640

Arg Val Glu Tyr Leu Leu Lys Ala Trp Ala Glu Lys Lys Asp Pro
2645                    2650                2655

Met Gly Phe Ser Tyr Asp Thr Arg Cys Phe Asp Ser Thr Val Thr
2660                    2665                2670

Glu Arg Asp Ile Arg Thr Glu Glu Ser Ile Tyr Gln Ala Cys Ser
2675                    2680                2685

Leu Pro Glu Glu Ala Arg Thr Ala Ile His Ser Leu Thr Glu Arg
2690                    2695                2700

Leu Tyr Val Gly Gly Pro Met Phe Asn Ser Lys Gly Gln Thr Cys
2705                    2710                2715

Gly Tyr Arg Arg Cys Arg Ala Ser Gly Val Leu Thr Thr Ser Met
2720                    2725                2730

```
Gly Asn Thr Ile Thr Cys Tyr Val Lys Ala Leu Ala Ala Cys Lys
    2735                2740                2745

Ala Ala Gly Ile Val Ala Pro Thr Met Leu Val Cys Gly Asp Asp
    2750                2755                2760

Leu Val Val Ile Ser Glu Ser Gln Gly Thr Glu Glu Asp Glu Arg
    2765                2770                2775

Asn Leu Arg Ala Phe Thr Glu Ala Met Thr Arg Tyr Ser Ala Pro
    2780                2785                2790

Pro Gly Asp Pro Pro Arg Pro Glu Tyr Asp Leu Glu Leu Ile Thr
    2795                2800                2805

Ser Cys Ser Ser Asn Val Ser Val Ala Leu Gly Pro Arg Gly Arg
    2810                2815                2820

Arg Arg Tyr Tyr Leu Thr Arg Asp Pro Thr Thr Pro Leu Ala Arg
    2825                2830                2835

Ala Ala Trp Glu Thr Val Arg His Ser Pro Ile Asn Ser Trp Leu
    2840                2845                2850

Gly Asn Ile Ile Gln Tyr Ala Pro Thr Ile Trp Val Arg Met Val
    2855                2860                2865

Leu Met Thr His Phe Phe Ser Ile Leu Met Val Gln Asp Thr Leu
    2870                2875                2880

Asp Gln Asn Leu Asn Phe Glu Met Tyr Gly Ser Val Tyr Ser Val
    2885                2890                2895

Asn Pro Leu Asp Leu Pro Ala Ile Ile Glu Arg Leu His Gly Leu
    2900                2905                2910

Asp Ala Phe Ser Met His Thr Tyr Ser His His Glu Leu Thr Arg
    2915                2920                2925

Val Ala Ser Ala Leu Arg Lys Leu Gly Ala Pro Pro Leu Arg Val
    2930                2935                2940

Trp Lys Ser Arg Ala Arg Ala Val Arg Ala Ser Leu Ile Ser Arg
    2945                2950                2955

Gly Gly Lys Ala Ala Val Cys Gly Arg Tyr Leu Phe Asn Trp Ala
    2960                2965                2970

Val Lys Thr Lys Leu Lys Leu Thr Pro Leu Pro Glu Ala Arg Leu
    2975                2980                2985

Leu Asp Leu Ser Ser Trp Phe Thr Val Gly Ala Gly Gly Gly Asp
    2990                2995                3000

Ile Phe His Ser Val Ser Arg Ala Arg Pro Arg Ser Leu Leu Phe
    3005                3010                3015

Gly Leu Leu Leu Leu Phe Val Gly Val Gly Leu Phe Leu Leu Pro
    3020                3025                3030

Ala Arg
    3035

<210> SEQ ID NO 7
<211> LENGTH: 24
<212> TYPE: DNA
<213> ORGANISM: Artificial Sequence
<220> FEATURE:
<223> OTHER INFORMATION: oligoDNA primer

<400> SEQUENCE: 7
ctatggagtg tacctagtgt gtgc                                            24

<210> SEQ ID NO 8
<211> LENGTH: 30
<212> TYPE: DNA
```

```
<213> ORGANISM: Artificial Sequence
<220> FEATURE:
<223> OTHER INFORMATION: oligoDNA orimer

<400> SEQUENCE: 8
actgtcttca cgcagaaagc gcctagccat                                      30

<210> SEQ ID NO 9
<211> LENGTH: 40
<212> TYPE: DNA
<213> ORGANISM: Artificial Sequence
<220> FEATURE:
<223> OTHER INFORMATION: oligoDNA primer

<400> SEQUENCE: 9
gtagcgttgg gttgcgaaag gccttgtggt actgcctgat                           40

<210> SEQ ID NO 10
<211> LENGTH: 25
<212> TYPE: DNA
<213> ORGANISM: Artificial Sequence
<220> FEATURE:
<223> OTHER INFORMATION: oligoDNA primer

<400> SEQUENCE: 10
cctacggaat cccgttgcag gtgtg                                           25

<210> SEQ ID NO 11
<211> LENGTH: 26
<212> TYPE: DNA
<213> ORGANISM: Artificial Sequence
<220> FEATURE:
<223> OTHER INFORMATION: oligoDNA primer

<400> SEQUENCE: 11
tgtgggtggg caggttggct cctgtc                                          26

<210> SEQ ID NO 12
<211> LENGTH: 36
<212> TYPE: DNA
<213> ORGANISM: Artificial Sequence
<220> FEATURE:
<223> OTHER INFORMATION: oligoDNA primer

<400> SEQUENCE: 12
gtggttccta ctacgacagg gctgggcgtg aagcag                               36

<210> SEQ ID NO 13
<211> LENGTH: 23
<212> TYPE: DNA
<213> ORGANISM: Artificial Sequence
<220> FEATURE:
<223> OTHER INFORMATION: oligoDNA primer

<400> SEQUENCE: 13
ctttgaactg caatgattcc ctc                                             23

<210> SEQ ID NO 14
<211> LENGTH: 23
<212> TYPE: DNA
<213> ORGANISM: Artificial Sequence
<220> FEATURE:
<223> OTHER INFORMATION: oligoDNA sequence

<400> SEQUENCE: 14
catgtaggta cacgcaggca caa                                             23
```

```
<210> SEQ ID NO 15
<211> LENGTH: 23
<212> TYPE: DNA
<213> ORGANISM: Artificial Sequence
<220> FEATURE:
<223> OTHER INFORMATION: oligoDNA primer

<400> SEQUENCE: 15
ctggaccaga ggcgagcggt gtg                                          23

<210> SEQ ID NO 16
<211> LENGTH: 32
<212> TYPE: DNA
<213> ORGANISM: Artificial Sequence
<220> FEATURE:
<223> OTHER INFORMATION: oligoDNA primer

<400> SEQUENCE: 16
agtgatggga gccaaaagct tccaaccccc gc                                32

<210> SEQ ID NO 17
<211> LENGTH: 22
<212> TYPE: DNA
<213> ORGANISM: Artificial Sequence
<220> FEATURE:
<223> OTHER INFORMATION: oligoDNA primer

<400> SEQUENCE: 17
ggggtaagta cgtgcaggcg tg                                           22

<210> SEQ ID NO 18
<211> LENGTH: 26
<212> TYPE: DNA
<213> ORGANISM: Artificial Sequence
<220> FEATURE:
<223> OTHER INFORMATION: oligoDNA primer

<400> SEQUENCE: 18
cgcccgaggc ctacctcttc tatatc                                       26

<210> SEQ ID NO 19
<211> LENGTH: 24
<212> TYPE: DNA
<213> ORGANISM: Artificial Sequence
<220> FEATURE:
<223> OTHER INFORMATION: oligoDNA primer

<400> SEQUENCE: 19
cccatcacgt actccacata tggc                                         24

<210> SEQ ID NO 20
<211> LENGTH: 22
<212> TYPE: DNA
<213> ORGANISM: Artificial Sequence
<220> FEATURE:
<223> OTHER INFORMATION: oligoDNA primer

<400> SEQUENCE: 20
gcgcacaccg tagcttggta gg                                           22

<210> SEQ ID NO 21
<211> LENGTH: 25
<212> TYPE: DNA
<213> ORGANISM: Artificial Sequence
<220> FEATURE:
<223> OTHER INFORMATION: oligoDNA primer
```

-continued

```
<400> SEQUENCE: 21
gagcgagcct caggaatgtt tgaca                                         25

<210> SEQ ID NO 22
<211> LENGTH: 24
<212> TYPE: DNA
<213> ORGANISM: Artificial Sequence
<220> FEATURE:
<223> OTHER INFORMATION: oligoDNA primer

<400> SEQUENCE: 22
tgatgttgag aaggatggtg gtac                                          24

<210> SEQ ID NO 23
<211> LENGTH: 24
<212> TYPE: DNA
<213> ORGANISM: Artificial Sequence
<220> FEATURE:
<223> OTHER INFORMATION: oligoDNA primer

<400> SEQUENCE: 23
tggcccaaag tggaacaatt ttgg                                          24

<210> SEQ ID NO 24
<211> LENGTH: 24
<212> TYPE: DNA
<213> ORGANISM: Artificial Sequence
<220> FEATURE:
<223> OTHER INFORMATION: oligoDNA primer

<400> SEQUENCE: 24
caacgcagaa cgagacctca tccc                                          24

<210> SEQ ID NO 25
<211> LENGTH: 24
<212> TYPE: DNA
<213> ORGANISM: Artificial Sequence
<220> FEATURE:
<223> OTHER INFORMATION: oligoDNA primer

<400> SEQUENCE: 25
gacctttcct atcaattgct acac                                          24

<210> SEQ ID NO 26
<211> LENGTH: 24
<212> TYPE: DNA
<213> ORGANISM: Artificial Sequence
<220> FEATURE:
<223> OTHER INFORMATION: oligoDNA primer

<400> SEQUENCE: 26
gaagctctac ctgatcagac tcca                                          24

<210> SEQ ID NO 27
<211> LENGTH: 20
<212> TYPE: DNA
<213> ORGANISM: Artificial Sequence
<220> FEATURE:
<223> OTHER INFORMATION: oligoDNA primer

<400> SEQUENCE: 27
tgggcacggc ctgactacaa                                               20

<210> SEQ ID NO 28
<211> LENGTH: 24
<212> TYPE: DNA
```

```
<213> ORGANISM: Artificial Sequence
<220> FEATURE:
<223> OTHER INFORMATION: oligoDNA primer

<400> SEQUENCE: 28
ggccattttc tcgcagaccc ggac                                              24

<210> SEQ ID NO 29
<211> LENGTH: 24
<212> TYPE: DNA
<213> ORGANISM: Artificial Sequence
<220> FEATURE:
<223> OTHER INFORMATION: oligoDNA primer

<400> SEQUENCE: 29
atggccaaaa atgaggtgtt ctgc                                              24

<210> SEQ ID NO 30
<211> LENGTH: 24
<212> TYPE: DNA
<213> ORGANISM: Artificial Sequence
<220> FEATURE:
<223> OTHER INFORMATION: oligoDNA primer

<400> SEQUENCE: 30
aaggtccaaa ggattcacgg agta                                              24

<210> SEQ ID NO 31
<211> LENGTH: 26
<212> TYPE: DNA
<213> ORGANISM: Artificial Sequence
<220> FEATURE:
<223> OTHER INFORMATION: oligoDNA primer

<400> SEQUENCE: 31
ggtcaaacct gcggttacag acgttg                                            26

<210> SEQ ID NO 32
<211> LENGTH: 24
<212> TYPE: DNA
<213> ORGANISM: Artificial Sequence
<220> FEATURE:
<223> OTHER INFORMATION: oligoDNA primer

<400> SEQUENCE: 32
gtgtacctag tgtgtgccgc tcta                                              24
```